US010377780B2

(12) United States Patent
Gunning et al.

(10) Patent No.: US 10,377,780 B2
(45) Date of Patent: *Aug. 13, 2019

(54) SALICYLIC ACID DERIVATIVES, PHARMACEUTICALLY ACCEPTABLE SALT THEREOF, COMPOSITION THEREOF AND METHOD OF USE THEREOF

(71) Applicants: The Governing Council of the University of Toronto, Toronto (CA); UTI Limited Partnership, Calgary (CA); Indiana University Research and Technology Corporation, Indianapolis, IN (US)

(72) Inventors: Patrick Thomas Gunning, Streetsville (CA); Sina Haftchenary, Thornhill (CA); Brent David George Page, Hamilton (CA); Samuel Weiss, Calgary (CA); Hema Artee Luchman, Calgary (CA); Melissa L. Fishel, Indianapolis, IN (US)

(73) Assignees: The Governing Council of the University of Toronto, Toronto (CA); UTI Limited Partnership, Calgary (CA); Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/475,108

(22) Filed: Mar. 30, 2017

(65) Prior Publication Data
US 2017/0267704 A1   Sep. 21, 2017

Related U.S. Application Data

(63) Continuation of application No. 14/550,293, filed as application No. PCT/US2013/042689 on May 24, 2013, now Pat. No. 9,650,399.

(60) Provisional application No. 61/651,757, filed on May 25, 2012.

(51) Int. Cl.
| | | |
|---|---|---|
| C07F 9/40 | (2006.01) | |
| C07D 215/36 | (2006.01) | |
| C07D 233/84 | (2006.01) | |
| C07C 311/19 | (2006.01) | |
| C07C 311/21 | (2006.01) | |
| C07F 9/38 | (2006.01) | |

(52) U.S. Cl.
CPC .............. *C07F 9/40* (2013.01); *C07C 311/19* (2013.01); *C07C 311/21* (2013.01); *C07D 215/36* (2013.01); *C07D 233/84* (2013.01); *C07F 9/3882* (2013.01); *C07C 2601/14* (2017.05)

(58) Field of Classification Search
None
See application file for complete search history.

(56) References Cited

U.S. PATENT DOCUMENTS

| 2009/0069420 A1 | 3/2009 | Turkson et al. |
| 2012/0130079 A1 | 5/2012 | Turkson et al. |
| 2016/0068478 A1 | 3/2016 | Turkson et al. |

FOREIGN PATENT DOCUMENTS

| WO | WO2010/117438 | 10/2010 |
| WO | WO2012/018868 | 2/2012 |

OTHER PUBLICATIONS

Bowman, T. et al. (2000) STATs in oncogenesis. Oncogene, 19:2474-88.
Page, B. et al. (2011) Identification of a non-phosphorylated, cell permeable, small molecule ligand for the Stat3 SH2 domain. Bioorganic & Medicinal Chemistry Letters, 21:5605-5609.
Page, B. et al. (2012) Small Molecule STAT5-SH2 Domain Inhibitors Exhibit Potent Antileukemia Activity. Journal of Medicinal Chemistry, 55:1047-1055.
Buettner, R., et al. (Apr. 2002) Activated STAT Signaling in Human Tumors Provides Novel Molecular Targets for Therapeutic Intervention. Clinical Cancer Research, 8:945-954.
Carro, M.S., et al. (2010) The transcriptional network for mesenchymal transformation of brain tumours. Nature vol. 463, No. 7279, pp. 318-325.
Darnell, J.E. (2005) Validating Stat3 in cancer therapy. Nature Medicine, vol. 11, No. 6, pp. 595-596.
Fotini Debonera, B.S., et al. (2001) Activation of Interleukin-6/STAT3 and Liver Regeneration Following Transplantation. Journal of Surgical Research, vol. 96, No. 2, pp. 289-295.
Gouilleux-Gruart, V., et al. (1996) STAT-Related Transcription Factors Are Constitutively Activated in Peripheral Blood Cells From Acute Leukemia Patients, Blood, vol. 87, No. 5, pp. 1692-1697.
Gouilleux-Gruart, V., et al. (2009) Activated Stat Related Transcription Factors in Acute Leukemia. Leukemia and Lymphoma, 28:83-88.

(Continued)

*Primary Examiner* — Samantha L Shterengarts
(74) *Attorney, Agent, or Firm* — Meunier Carlin & Curfman LLC

(57) ABSTRACT

The present invention relates to novel compounds, compositions containing same and methods for inhibiting STAT3 and/or STAT5 activity or for the treatment of a STAT3 or STAT5-dependent cancer using said compounds;

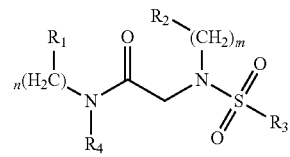

or a pharmaceutically acceptable salt, solvate or prodrug thereof.

15 Claims, 20 Drawing Sheets

(56) References Cited

OTHER PUBLICATIONS

Harris, T. J., et al. (2007) Cutting Edge: An In Vivo Requirement for STAT3 Signaling in TH17 Development and TH17-Dependent Autoimmunity. Journal of Immunology, vol. 179, No. 5, pp. 4313-4317.

Haura, E.B., et al. (2005) Mechanisms of Disease: insights into the emerging role of signal transducers and activators of transcription in cancer. Nature Clinical Practice: Oncology, vol. 2, No. 6, pp. 315-324.

Kelly, J.P., et al. (2009) Proliferation of Human Glioblastoma Stem Cells Occurs Independently of Exogenous Mitogens. Stem Cells, 27:1722-1733.

Mashili, F. et al. (2013) Constitutive STAT3 Phosphorylation Contributes to Skeletal Muscle Insulin Resistance in Type 2 Diabetes. Diabetes, 62:457-465.

Miyamoto. T, et al (2012) STAT3 is critical to promote inflammatory cytokines and RANKL expression in inflammatory arthritis. Arthritis Research & Therapy, vol. 14, Suppl 1, p. 43.

Muller, J. et al. (2008) Discovery of Chromone-Based Inhibitors of the Transcription Factor STAT5. ChemBioChem, 9:723-727.

Pardanani, A., et al. (2011) JAK inhibitor therapy for myelofibrosis: critical assessment of value and limitations. Leukemia, 25:218-225.

Quintas-Cardama, et al. (2011) Janus kinase inhibitors for the treatment of myeloproliferative neoplasias and beyond. Nature Reviews: Drug Discovery, 10:127-140.

Schust, J., et al. (2004) A high-throughput fluorescence polarization assay for signal transducer and activator of transcription 3. Analytical Biochemistry, 330:114-118.

Siddiquee, K. et al. (2007) Selective chemical probe inhibitor of Stat3, identified through structure-based virtual screening, induces antitumor activity. Proceedings of the National Academy of Science U.S.A., vol. 104, No. 18, pp. 7391-7396.

Fletcher, S. et al. (2009) Disruption of Transcriptionally Active Stat3 Dimers with Non-phosphorylated, Salicylic Acid-Based Small Molecules: Potent in vitro and Tumor Cell Activities. ChemBioChem, 3:1159-1168.

Fletcher, S. et al. (2008) Molecular approaches towards the inhibition of the signal transducer and activator of transcription 3 (Stat3) Protein. ChemBioChem, 10:1959-1964.

Fletcher, S., et al. (2008) Mild, efficient and rapid O-debenzylation of ortho-substituted phenols with trifluoroacetic acid. Tetrahedron Letters, 49: 4817-4819.

Turkson, J. (2004) STAT proteins as novel targets for cancer drug discovery. Expert Opinion Therapeutic Targets, 8(5):409-422.

Turkson, J., et al. (Nov. 30, 2001) Phosphotyrosyl Peptides Block Stat3-mediated DNA Binding Activity, Gene Regulation, and Cell Transformation. The Journal of Biological Chemistry, vol. 276, No. 48, pp. 45443-45455.

Turkson, J., et al. (Mar. 2004) Novel peptidomimetic inhibitors of signal transducer and activator of transcription 3 dimenzation and biological activity. Molecular Cancer Therapeutics, 3(3):261-269.

Turkson, J., et al. (2005) A Novel Platinum Compound Inhibits Constitutive Stat3 Signaling and Induces Cell Cycle Arrest and Apoptosis of Malignant Cells. Journal of Biological Chemistry, vol. 280, No. 38, pp. 32979-3298.

Turkson, J., et al. (2004) Inhibition of constitutive signal transducer and activator of transcription 3 activation by novel platinum complexes with potent antitumor activity. Molecular Cancer Therapeutics, 3(12):1533-1542.

Weber-Nordt, R. M., et al. (1996) Constitutive Activation of STAT Proteins in Primary Lymphoid and Myeloid Leukemia Cells and in Epstein-Barr Virus (EBV)-Related Lymphoma Cell Lines. Blood, vol. 88, No. 3, pp. 809-816.

Weimbs, T., et al. (2013) Regulation of STATs by polycystin-1 and their role in polycystic kidney disease. JAK-STAT, 2:2, e23650.

Sugimoto, K. (2008) Role of STAT3 in inflammatory bowel disease. World Journal of Gastroenterology, vol. 14, No. 33, pp. 5110-5114.

Wu, P. et al. (1997) A High-Throughput STAT Binding Assay Using Fluorescence Polarization. Analytical Biochemistry, 249:29-36.

Yu, H. and Jove. R. (2004) The stats of cancer—New molecular targets come of age. Nature Reviews: Cancer 4:97-105.

Zhang, X., et al. (2010) A novel small-molecule disrupts Stat3 SH2 domain-phosphotyrosine interactions and Stat3-dependent tumor processes. Biochemical Pharmacology, 79:1398-1409.

Darnell, J.E. (1996) The JAK-STAT pathway: summary of initial studies and recent advances. Recent Progress in Hormone Research, 51: 391-403.

Urlam, M.K., et al. (2013) Development of new N-Arylbenzamides as STAT3 Dimerization Inhibitors, Med. Chem. Commun. 2013, 4, 932-941.

Fletcher, S. et al. (2011) Antagonism of the Stat3-Stat3 Protein Dimer with Salicylic Acid Based Small Molecules. ChemMedChem, vol. 6, No. 8, 1459-1470.

International Search Report and Written Opinion issued by the ISA/US Commissioner for Patents, dated Nov. 12, 2013, for International Application PCT/US2013/042689, 15 pages.

| Compound | R4 | IC50 25EF (nM) | IC50 67EF (nM) | IC50 73EF (nM) | IC50 84EF (nM) | IC50 127EF (nM) |
|---|---|---|---|---|---|---|
| 32 | | 1120.5±301.9 | 214.5±36.1 | 863.5±443.4 | 285±35.4 | 195.5±20.5 |
| 22 | | 1145±162.6 | 435.5±176.1 | 1075±247.5 | 332±16.9 | 272.5±24.8 |
| 33 | | 592±195.5 | 214±93.4 | 438±107.5 | 202.5±17.7 | 90±14.2 |
| 31 | | 234±73.4 | 106±19.8 | 162±59.4 | 102±2.8 | 66±33.9 |

| Target | SH-04-54 | Target | SH-04-54 |
|---|---|---|---|
| Gene Symbol | %Ctrl@500nM | Gene Symbol | %Ctrl@500nM |
| ABL1(E255K)-phosphorylated | 100 | MAPKAPK2 | 72 |
| ABL1(T315I)-phosphorylated | 100 | MARK3 | 100 |
| ABL1-nonphosphorylated | 100 | MEK1 | 98 |
| ABL1-phosphorylated | 100 | MEK2 | 99 |
| ACVR1B | 100 | MET | 78 |
| ADCK3 | 100 | MKNK1 | 58 |
| AKT1 | 100 | MKNK2 | 100 |
| AKT2 | 81 | MLK1 | 73 |
| ALK | 100 | p38-alpha | 100 |
| AURKA | 98 | p38-Beta | 75 |
| AURKB | 100 | PAK1 | 97 |
| AXL | 93 | PAK2 | 100 |
| BMPR2 | 100 | PAK4 | 100 |
| BRAF | 63 | PCTK1 | 84 |
| BRAF(V600E) | 63 | PDGFRA | 100 |
| BTK | 100 | PDGFRB | 55 |
| CDK11 | 100 | PDPK1 | 100 |

Fig-8

| Target Gene Symbol | SH-04-54 %Ctrl@500nM | Target Gene Symbol | SH-04-54 %Ctrl@500nM |
|---|---|---|---|
| CDK2 | 100 | PIK3C2B | 100 |
| CDK3 | 100 | PIK3CA | 100 |
| CDK7 | 92 | PIK3CG | 100 |
| CDK9 | 100 | PIM1 | 100 |
| CHEK1 | 100 | PIM2 | 100 |
| CSF1R | 100 | PIM3 | 100 |
| CSNK1D | 100 | PKAC-alpha | 100 |
| CSNK1G2 | 100 | PLK1 | 45 |
| DCAMKL1 | 100 | PLK3 | 100 |
| DYRK1B | 98 | PLK4 | 81 |
| EGFR | 100 | PRKCE | 98 |
| EGFR(L858R) | 100 | RAF1 | 78 |
| EPHA2 | 100 | RET | 96 |
| ERBB2 | 100 | RIOK2 | 100 |
| ERBB4 | 75 | ROCK2 | 100 |
| ERK1 | 91 | RSK2(Kin.DOM.1-N-TERMINAL) | 100 |
| FAK | 94 | SNARK | 100 |

Fig. 6 (Cont.)

| Target Gene Symbol | SH-04-54 %Ctrl@500nM | Target Gene Symbol | SH-04-54 %Ctrl@500nM |
|---|---|---|---|
| FER | 100 | SRC | 100 |
| FES | 93 | SRPK3 | 92 |
| FGFR2 | 100 | TGFBR1 | 71 |
| FGFR3 | 100 | TIE2 | 71 |
| FGR | 99 | TRKA | 100 |
| FLT3 | 85 | TSSK1B | 70 |
| FYN | 100 | TYK2 (JH1 domain-catalytic) | 100 |
| GSK3B | 100 | ULK2 | 100 |
| IGF1R | 100 | VEGFR2 | 100 |
| IKK-alpha | 77 | YANK3 | 80 |
| IKK-beta | 83 | ZAP70 | 100 |
| INSR | 94 | KIT(D816V) | 88 |
| JAK2(JH1 domain-catalytic) | 64 | KIT(V559D,T670I) | 100 |
| JAK3(JH1 domain-catalytic) | 87 | LKB1 | 100 |
| JNK1 | 100 | MAP3K4 | 100 |
| JNK2 | 100 | KIT | 68 |
| JNK3 | 100 | | |

Fig. 6 (Cont.)

A. Control | B. Inhibitor 31 (10mg/kg)

A. Control | B. Inhibitor 31 (10mg/kg)

A. Control | B. Inhibitor 31 (10mg/kg)

SALICYLIC ACID DERIVATIVES, PHARMACEUTICALLY ACCEPTABLE SALT THEREOF, COMPOSITION THEREOF AND METHOD OF USE THEREOF

CROSS-REFERENCE TO RELATED APPLICATIONS

This application is a continuation of U.S. patent application Ser. No. 14/550,293, filed Nov. 21, 2014, which is a U.S. National Stage Entry of International Application No. PCT/US2013/042689, filed May 24, 2013, which claims priority from U.S. Provisional Application Ser. No. 61/651,757, filed May 25, 2012, each of which is expressly incorporated herein by reference in its entirety.

STATEMENT OF GOVERNMENT INTEREST

This invention was made with government support under CA167291 awarded by the National Institutes of Health. The Government has certain rights in the invention.

FIELD OF THE DISCLOSURE

The present invention relates to novel salicylic acid derivative compound, compositions containing same and methods inhibiting STAT3 activity or for treating cancer where STAT3/5 are involved, such as in brain, breast, colon, hematologic, lung, ovarian and prostate cancers using said compounds.

BACKGROUND OF THE DISCLOSURE

STAT3 is persistently activated in over a dozen types of human cancers, including all the major carcinomas, including breast, brain, colon, pancreas, ovarian, and squamous cell carcinomas of head and neck (SCCHN) cancers, and melanomas as well as some hematologic tumors (Bowman T, et al (2000) Oncogene 19, 2474-88, and Darnell, J. E. (2005) Nat. Med. 1 1, 595-596). As such, there is increasing interest in developing anticancer therapies through the inhibition of persistently active STAT3, especially as a strategy to deal with cancers where physicians are looking to improve the outcome and/or where even establishing a satisfactory standard of care has been challenging in terms of patient care, quality of life and outcome.

Glioblastoma (GBM) is considered the most aggressive and lethal of brain cancers, with a median survival after treatment of approximately 15 months. Shockingly, these modest results can only be achieved in the relatively young (i.e., <age 70) and otherwise healthy patients. Older patients with GBM, of which there are many, and those with poor performance status at diagnosis have much shorter survivals following identical therapy. In addition, GBM is occurring with increasing frequency in an aging population. Moreover, unlike the more common cancers, such as those of the lung, breast and colon, GBM is neither preventable, nor detectable at a stage when early treatment might be expected to be substantially more effective. Furthermore, despite decades of intensive research, major improvements in overall survival have remained elusive. As such, the development of therapeutic approaches to meet this unmet need is critical.

Brain tumours have been demonstrated to contain rare subpopulations of brain tumour stem cells (BTSCs), which possess the cardinal stem cell properties of clonogenic self-renewal, multipotency and tumourigenicity. The extensive self-renewal and proliferative capacity of BTSCs coupled with their insensitivity to conventional radio- and chemotherapies suggest that they are integral to the growth and post-treatment recurrence of GBM. As such, BTSCs represent a "reservoir of disease" that require novel therapeutic approaches to effectively eliminate in order to improve the outcome of GBM.

STAT proteins were originally discovered as latent cytoplasmic transcription factors that mediate cytokine and growth factor responses (Darnell, J. E., Jr. (1996) Recent Prog. Norm. Res. 51, 391-403; Darnell, J. E. (2005) Nat. Med. 1 1, 595-596). Seven members of the family, STAT1, STAT2, STAT3, STAT4, STAT5a and STAT5b, and STAT6, mediate several physiological effects including growth and differentiation, survival, development and inflammation. STATs are SH2 domain-containing proteins. Upon ligand binding to cytokine or growth factor receptors, STATs become phosphorylated on critical Tyr residue (Tyr705 for STAT3) by growth factor receptors, cytoplasmic Janus kinases (Jaks) or Src family kinases. Two phosphorylated and activated STAT monomers dimerize through reciprocal pTyr-SH2 domain interactions, translocate to the nucleus, and bind to specific DNA-response elements of target genes, thereby inducing gene transcription (Darnell, J. E., Jr. (1996) Recent Prog. Norm. Res. 51, 391-403; Darnell, J. E. (2005) Nat. Med. 1 1, 595-596). In contrast to normal STAT signaling, many human solid and hematological tumors harbor aberrant STAT3 activity (Turkson, J. Expert Opin. Ther. Targets 2004, 8, 409-422; Darnell, J. E., Jr. (1996) Recent Prog. Norm. Res. 51, 391-403; Darnell, J. E. (2005) Nat. Med. 11(6), 595-596; Bowman, T. et al. (2000) Oncogene 19(21), 2474-2488; Buettner, et al. (2002) Clin. Cancer Res. 8(4), 945-954; Yu, H. and Jove. R. (2004) Nat. Rev. Cancer 4(2), 97-105; Haura, E. B., et al. (2005) Nat. Clin. Pract. Oncol. 2(6), 315-324).

Of note, STAT3 protein is one of seven family members of the STAT family of transcription factor proteins. STAT3 is activated through phosphorylation of a tyrosine 705 (Y705) that initiates complexation of two phosphorylated STAT3 monomers (pSTAT3). pSTAT3 homodimers are mediated through reciprocal STAT3 Src Homology 2 (SH2) domain-pY705 STAT3 interactions. pSTAT3:pSTAT3 homodimers translocate to the nucleus and bind DNA, promoting STAT3 target gene transcription. Targeting STAT3 has been previously achieved with dominant negative constructs, oligonucleotides or, most commonly, phosphopeptidic agents that mimic the native pY705 containing binding sequence. Unfortunately, these inhibitors are rapidly degraded in vivo, which limits their use in the clinic. To circumvent these problems, small molecule STAT3 inhibitors were designed for treatment of cancers harboring hyperactivated STAT3 protein. Acid-based inhibitors have been identified in WO2012/018868 that potently and selectively block STAT3 dimerization and DNA-binding activity, namely, compound 450, also referred to as BP-1-102 (sometimes referred to as compound 1 herein). Compound 450 in WO2012018868 potently suppresses multiple oncogenic properties in diverse cultured cancer cells (breast, lung, pancreatic, prostate, lung), including: cell proliferation, anchorage-independent cell growth, migration, invasion and motility. It is selective for STAT3, with over 10-fold less binding to 93% homologous STAT protein, STAT1. It showed little or no effect on phosphorylation of Shc, Src, Jak-1/2, Erk1/2 or Akt and had no effect on non-transformed cells (NIH 3T3 cells, STAT3 null mouse embryo fibroblasts, or mouse thymus stromal cells, nor does it affect transformed cells that do not harbor activated STAT3). Moreover, BP-1-102 exhibited striking anti-tumor effects in vivo in murine xenograft models of lung or breast cancer resulting in dramatic regression in tumor volumes. Western blots of residual tumors from treated mice showed repression in pSTAT3, cMyc, Cyclin D1, Bcl-xL, Survivin, and VEGF in a dose-dependent manner.

Moreover, genetic and other molecular evidence reveals persistent Tyr phosphorylation of STAT3 is mediated by aberrant upstream Tyr kinases and shows cancer cell requirement for constitutively-active and dimerized STAT3 for tumor maintenance and progression. Thus, in numerous proof-of-concept studies (Turkson, J., et al. Mol. Cancer Ther. 2004, 3(3), 261-269; Turkson, J., et al. J. Biol. Chem. 2001, 276(48), 45443-45455; Siddiquee, K.; et al. Proc. Natl. Acad. Sci. U.S.A. 2007, 104, 7391-7396; Turkson, J.; et al. Mol. Cancer Ther. 2004, 3, 1533-1542; and Turkson, J.; et al. J. Biol. Chem. 2005, 280(38), 32979-32988), inhibition of STAT3 activation or disruption of dimerization induces cancer cell death and tumor regression. Small-molecule STAT3 inhibitors thus provide tools for probing the molecular dynamics of the cellular processing of STAT3 to understand STAT3's role as a signaling intermediate and a molecular mediator of the events leading to carcinogenesis and malignant progression. Moreover, since the STAT3 pathway is a key oncogenic driver in over a dozen types of human cancers, including all the major carcinomas, including breast, brain, colon, pancreas, ovarian, and squamous cell carcinomas of head and neck (SCCHN) cancers, and melanomas as well as some hematologic tumors (Bowman T, et al (2000) Oncogene 19, 2474-88, and Darnell, J. E. (2005) Nat. Med. 1 1, 595-596) the direct inhibition of STAT3 would provide a molecularly targeted route for effectively managing these cancers and especially aggressive forms such as GBM.

In a seminal paper, Carro et al. (*Nature*, 463(7279): 318-325, 2010) demonstrated that the Signal transducer and activator of transcription 3 (STAT3) gene abnormally active in GBM, is a critically important mediator of tumour growth and therapeutic resistance in GBM. Poorly treated brain cancers such as gliomas, astrocytomas and glioblastomas harbor constitutively activated STAT3. In addition, a growing body of recent evidence gathered using a variety of different small molecules that indirectly inhibit STAT3 by targeting upstream molecules such as the JAK family members, strongly suggest that STAT3 signaling is crucial for the survival and proliferation of BTSCs and GBM both in vitro and in vivo. However, due to their broad targeting nature existing drugs for treating GBM have limited translational potential due to numerous side effects. Hence, drugs with the ability to more specifically block STAT3 activity may provide effective treatment for GBM patients.

STAT5 signaling, like STAT3 signaling, is transiently activated in normal cells and is deactivated by a number of different cytosolic and nuclear regulators, including phosphatases, SOCS, PIAS, and proteasomal degradation. Like STAT3, STAT5 has gained notoriety for its aberrant role in human cancers and tumorigenesis, having been found to be constitutively activated in many cancers, including those of the breast, liver, prostate, blood, skin, head and neck. (Muller, J., et al. ChemBioChem 2008, 9, 723-727). In cancer cells, STAT5 is routinely constitutively phosphorylated which leads to the aberrant expression of STAT5 target genes resulting in malignant transformation. Cancer cells harbouring persistently activated STAT5 over express anti-apoptotic proteins, such as Bcl-xL, Myc and MCL-1, conferring significant resistance to natural apoptotic cues and administered chemotherapeutic agents. Of particular interest, STAT5 has been identified as a key regulator in the development and progression of acute myelogenic (AML) and acute lymphoblastic leukemias (ALL; Gouilleux-Gruart, V., et al. Leukemia and Lymphoma 1997, 28, 83-88; Gouilleux-Gruart, V., et al. Blood 1996, 87, 1692-1697; Weber-Nordt, R. M., et al. Blood 1996, 88, 809-816). Moreover, inhibitors of upstream STAT5 activators (such as JA and FLT3) have been shown to exhibit promising anti-cancer properties (Pardanani, A., et al. Leukemia 2011, 25, 218-225; Quintas-Cardama, A., et al. Nature Reviews Drug Discovery 2011, 10, 127-140).

It should be noted that, medical benefits through the inhibition of STAT3/5 are not limited to the various forms of cancer described herein where these targets are constitutively activated, but would also be applicable to treating other conditions where these pathways are know to play a key role, such as, but not limited to autoimmune disorders (Harris, T. J.; et al Immunol. (2007) 179(7): 4313-4317), inflammation associated with arthritis (Miyamoto. T, et al, Arthritis Research & Therapy (2012), 14(Suppl 1):P43), inflammatory bowel disease (IBD) (World J Gastroenterol. (2008) 14(33): 5110-5114), diabetes (Mashili, F.; et al (2013) Diabetes 62(2), 457-465), irritable bowel syndrome (IBS); kidney disease (Weimbs, T., (2013) JAK-STAT, 2(2), 0-1) and organ transplant (Debonera, F.; et al (2001) J. Surg. Res. 96(2), 289-295).

Despite advances in drug discovery directed to identifying inhibitors of STAT protein activity, there is still a scarcity of compounds that are both potent, efficacious, and selective activators of STAT3 and STAT5 and also effective in the treatment of cancer and other diseases associated with dysfunction in STAT3, STAT5 or both proteins, and diseases in which one or both of STAT3 and STAT5 is involved. Moreover, there is still a need for optimization of potency and reduced pharmacokinetic liabilities of existing compounds. These needs and other needs are satisfied by the present invention.

SUMMARY

In accordance with the purpose(s) of the invention, as embodied and broadly described herein, the invention, in one aspect, relates to compounds useful as inhibitors of STAT3.

In a further aspect, the disclosed compounds and products of disclosed methods of making, or a pharmaceutically acceptable salt, hydrate, solvate, or polymorph thereof, are modulators of STAT3 and/or STAT5 activity, methods of making same, pharmaceutical compositions comprising same, and methods of treating disorders associated with a STAT3 activity dysfunction using same.

In a still further aspect, the present invention relates to compounds that bind to STAT3 protein and negatively modulate STAT3 activity.

In a further aspect, the present invention relates to compounds that bind to STAT5 protein and negatively modulate STAT5 activity.

Also disclosed are pharmaceutical compositions comprising a therapeutically effective amount of a disclosed compound and a pharmaceutically acceptable carrier.

Disclosed are methods for the treatment of a disorder associated with STAT3/STAT5 activity dysfunction, preferably hyperactivity or over-expression, in a mammal comprising the step of administering to the mammal a therapeutically effective amount of a disclosed compound, or a pharmaceutically acceptable salt, hydrate, solvate, or polymorph thereof.

Also disclosed are methods for inhibition of STAT3 and/or STAT5 activity in a mammal comprising the step of administering to the mammal a therapeutically effective amount of least one disclosed compound, or a pharmaceutically acceptable salt, hydrate, solvate, or polymorph thereof.

Also disclosed are methods for inhibiting STAT3 and/or STAT5 activity in at least one cell, comprising the step of contacting the at least one cell with an effective amount of least one disclosed compound, or a pharmaceutically acceptable salt, hydrate, solvate, or polymorph thereof.

Also disclosed are uses of at least one disclosed compound, or a pharmaceutically acceptable salt, hydrate, solvate, or polymorph thereof.

In one aspect, there is provided a compound of formula I as defined herein.

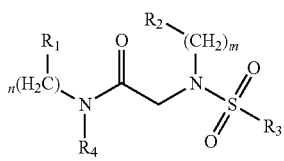

Formula 1 or a pharmaceutically acceptable salt, solvate or prodrug thereof, wherein
wherein each of m and n are independently an integer from 0-3;
wherein $R^1$ is selected from $A^1$, $A^2$, $-(A^1)-(A^2)$, $-(A^2)-(A^3)$, $-(A^3)-(A^2)$, $-(A^3)-(A^4)$, $-(A^5)-(A^1)-(A^7)$, $-(A^5)-(A^2)-(A^8)$, $-(A^5)-(A^3)-(A^7)$, and $-(A^5)-(A^6)-L-(A^7)$; wherein $A^1$ is $C_{3-6}$ cycloalkyl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-4}$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R^5$, $(C=O)OR^5$, and $(C=O)NHR^5$; wherein $A^2$ is $C_{3-6}$ cycloalkyl or heterocloalkyl, substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R6$, $(C=O)OR6$, and $(C=O)NHR6$; wherein $A^3$ is aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R7$, $(C=O)OR7$, and $(C=O)NHR7$; wherein $A^4$ is aryl, and substituted with 1-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_1$-$6)$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R8$, $(C=O)OR8$, and $(C=O)NHR8$; wherein $A^5$ is selected from $C_{3-6}$ cycloalkyl, $C_{3-6}$ heterocycloalkyl, and aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R9$, $(C=O)OR9$, and $(C=O)NHR9$; wherein $A^6$ is selected from $C_{3-6}$ cycloalkyl, $C_{3-6}$ heterocycloalkyl, and aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R10$, $(C=O)OR10$, and $(C=O)NHR10$; wherein $A^7$ is selected from $C_{3-6}$ cycloalkyl, $C_{3-6}$ heterocycloalkyl, and aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R11$, $(C=O)OR11$, and $(C=O)NHR11$; wherein $A^8$ is selected from $C_{3-6}$ cycloalkyl, $C_{3-6}$ heterocycloalkyl, and aryl, and substituted with 0-3 groups selected from halo, hydroxyl, amino, nitro, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_1$-$6)$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R12$, $(C=O)OR12$, and $(C=O)NHR12$;
wherein L is selected from $-(C=O)-$ and $-SO_2-$;
wherein $R^2$ is selected from $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, $C_{1-6}$ polyhaloalkyl, $C_{2-6}$ polyhaloalkenyl, $C_{2-6}$ polyhaloalkynyl; or wherein $R^2$ is aryl, and substituted with 0-5 groups independently selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)OR12$, and $(C=O)NHR12$; wherein $R^3$ is aryl substituted with 0-5 groups independently selected from halo, hydroxyl, amino, nitro, cyano, $C_{1-6}$ alkyl, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, and $(C_{1-6})$-alk-$(C_{1-6})$-polyhaloalkoxy;
wherein each of R5, R6, R7, R8, R9, R10, R11, and $R^{11}$ is independently selected from hydrogen, $C_{1-6}$ alkyl, $C_{1-6}$ haloalkyl, and $C_{1-6}$ polyhaloalkyl; or a pharmaceutically acceptable salt, hydrate, solvate, or polymorph thereof, wherein $R^2$ is selected from the group consisting of:
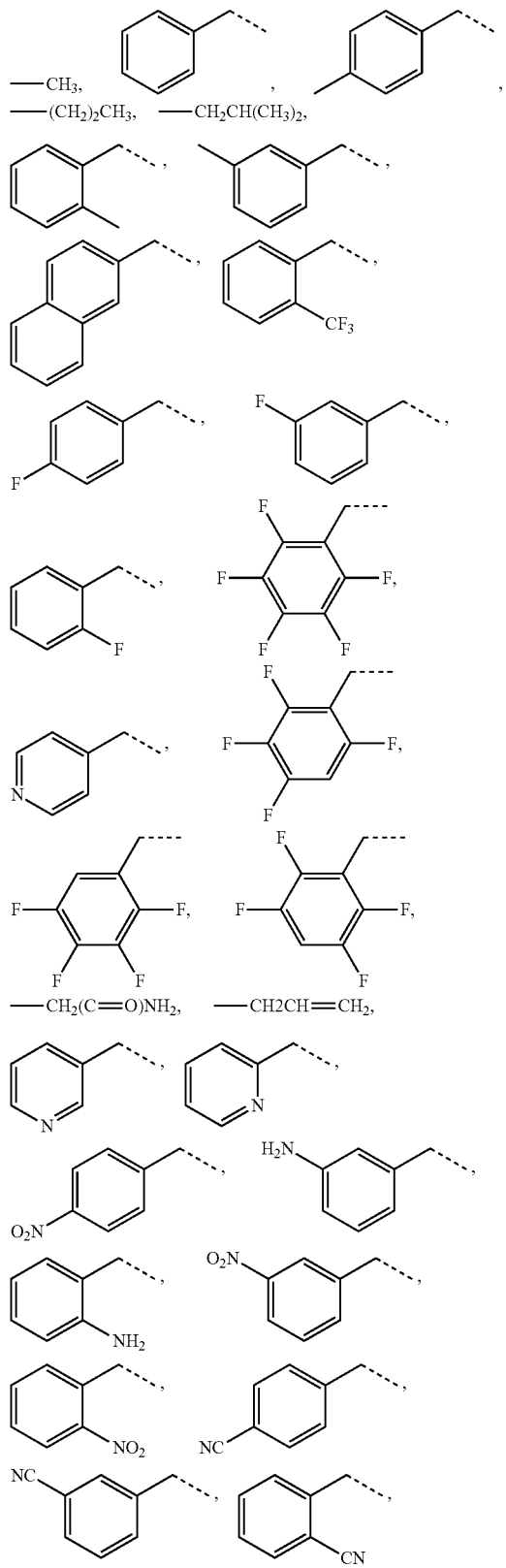
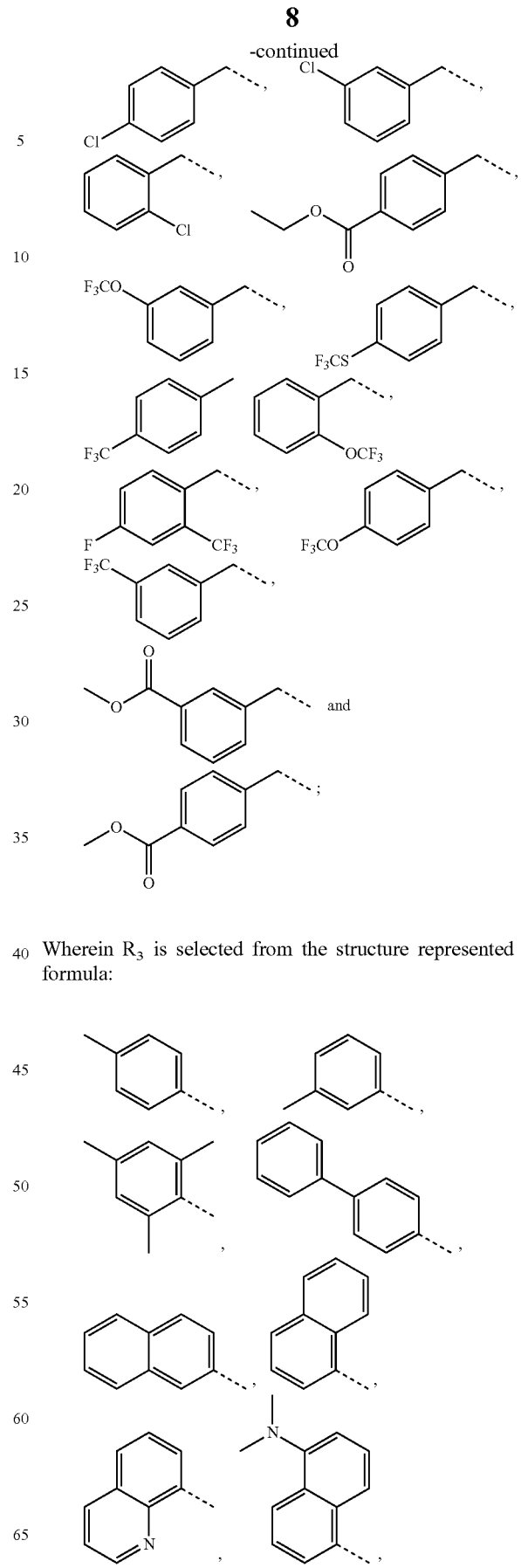
Wherein $R_3$ is selected from the structure represented by formula:

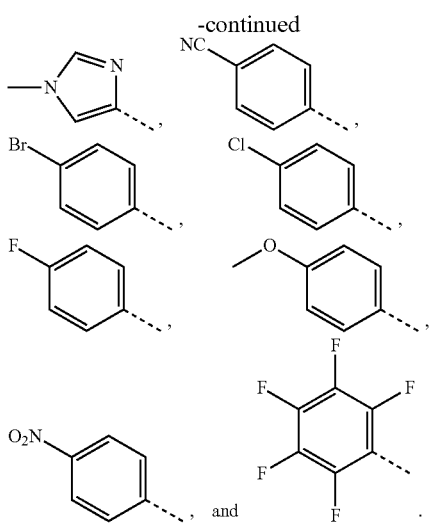

Wherein R⁴ is a structure represented by formula:

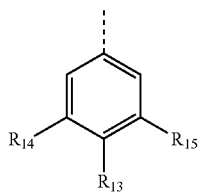

wherein $R^{13}$ is selected from the group consisting of —OH, —COR¹⁶, —CN, —CH₂PO(OH)₂, —CH₂P(O)₃(CH₂CH₃)₂, —NO₂, —NHR¹⁷, and 1H-tetrazole;
$R^{16}$ is selected from the group consisting of: —OH, —O—C$_{(1-2)}$alkyl, —OCH₂OC(O)CH₃, —OCH₂OC(O)t-Butyl, and —NHOH,
$R^{17}$ is selected from the group consisting of: —H, —C(O)C(O)CH₂CH₃, —C(O)C(O)OH, and —C(O)CH₂-1H-tetrazole
$R^{14}$ is —H or when $R^{13}$ is —COR¹⁶ and $R^{16}$ is OH, $R^{14}$ is —F, —OC(O)CH₃; and
$R^{15}$ is H or when $R^{13}$ is —COR¹⁶, $R^{16}$ is OH, and $R^{14}$ is H, $R^{15}$ is —F, —OC(O)CH₃
$R^{13}$ is —H when $R^{14}$ is —OH or both $R^{14}$ and $R^{15}$ are —COOH.

In a further aspect, the invention relates to pharmaceutical compositions comprising a pharmaceutically acceptable carrier and an effective amount of a disclosed compound, or a pharmaceutically acceptable salt, hydrate, solvate, or polymorph thereof.

In another aspect of the disclosure, there is provided a pharmaceutical composition comprising a compound as defined herein or a pharmaceutically acceptable salt, solvate or prodrug thereof, and an acceptable excipient.

In another aspect of the disclosure, there is provided a method for inhibiting STAT3 and/or STAT5 activity, comprising administering a therapeutically effective amount of a compound as defined herein or a pharmaceutically acceptable salt, solvate or prodrug thereof, to a patient.

In yet another aspect of the disclosure, there is provided a method for treating or preventing cancer associated with STAT3/STAT5 activity dysfunction (preferably hyperactivity thereof or over-expression of same) comprising administering a therapeutically effective amount of a compound as defined herein, or a pharmaceutically acceptable salt, solvate or prodrug thereof, to a patient. In alternative aspect, the cancer is from solid or hematological tumors. Still in other aspect, the cancer is one harbouring activated STAT3 and/or STAT5. Such cancer can be for example breast, liver, prostate, blood, skin, head, neck cancer, glioblastoma or acute myelogenic (AML) and acute lymphoblastic leukemias.

In another aspect of the disclosure, there is provided the use of a compound as defined herein or a pharmaceutically acceptable salt, solvate or prodrug thereof, in the manufacture of a medicament for inhibiting STAT3 and/or STAT5 activity.

In another aspect of the disclosure, there is provided the use of a compound as defined herein or a pharmaceutically acceptable salt, solvate or prodrug thereof, in the manufacture of a medicament for treating or preventing cancer harbouring activated STAT3 and/or STAT5, such as cancer from solid or hematological tumors, breast cancer, liver cancer, prostate cancer, blood cancer, skin cancer, head cancer, neck cancer, glioblastoma or acute myelogenic (AML) and acute lymphoblastic leukemias.

In yet another aspect of the disclosure, there is provided the use of a compound as defined herein or a pharmaceutically acceptable salt, solvate or prodrug thereof, for inhibiting STAT3 and/or STAT5 activity.

In another aspect of the disclosure, there is provided the use of a compound as defined herein or a pharmaceutically acceptable salt, solvate or prodrug thereof, for treating or preventing cancer harbouring activated STAT3 and/or STAT5, such as the cancer is from solid or hematological tumors, breast cancer, liver cancer, prostate cancer, blood cancer, skin cancer, head cancer, neck cancer, glioblastoma or acute myelogenic (AML) and acute lymphoblastic leukemias associated with STAT3/STAT5 activity dysfunction, such as breast, prostate or brain cancer.

In another aspect of the disclosure, there is provided a pharmaceutical composition as defined herein for use in inhibiting STAT3 and/or STAT5 activity.

In yet another aspect of the disclosure there is provided a pharmaceutical composition as defined herein for use in treating or preventing cancer harbouring activated STAT3 and/or STAT5, such as the cancer is from solid or hematological tumors, breast cancer, liver cancer, prostate cancer, blood cancer, skin cancer, head cancer, neck cancer, glioblastoma or acute myelogenic (AML) and acute lymphoblastic leukemias.

Also disclosed are methods for manufacturing a medicament, comprising combining at least one disclosed compound or at least one disclosed product with a pharmaceutically acceptable carrier or diluent. In a further aspect, the invention relates to the use of a disclosed compound in the manufacture of a medicament for the treatment of a disorder associated with STAT3/STAT5 activity dysfunction (such as hyperactivity or over-expression). In a still further aspect, the invention relates to the use of the disclosed compound in the manufacture of a medicament for the treatment of a cancer harbouring activated STAT3 and/or STAT5, such as the cancer is from solid or hematological tumors, breast cancer, liver cancer, prostate cancer, blood cancer, skin cancer, head cancer, neck cancer, glioblastoma or acute myelogenic (AML) and acute lymphoblastic leukemias.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The present invention can be understood more readily by reference to the following detailed description of the invention and the Examples included therein.

BRIEF DESCRIPTION OF THE DRAWINGS

FIG. 6 is a table illustrating the measurements of kinase concentration in eluates by qPCR;

DESCRIPTION OF THE EMBODIMENTS

Figure 1A:
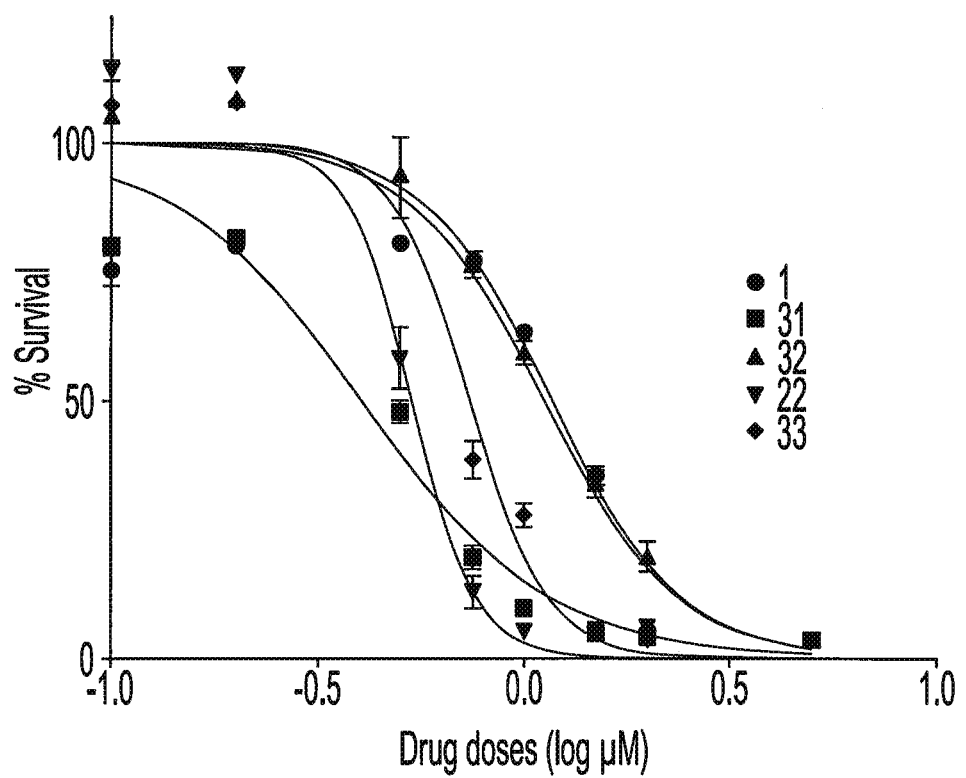
FIG. 1A is a graph illustrating a comparison of compound 1 against compounds 22, 31, 32, and 33 from library BTSC30M.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, EIZ specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the terms "STAT3," "signal transducer and activator of transcription 3 (acute-phase response)," and "signal transducer and activator of transcription 3" can be used interchangeably and refer to a a transcription factor encoded by a gene designated in human as the STAT3 gene, which has a human gene map locus of 17q21 and described by Entrez Gene cytogenetic band: 17q21.31; Ensembl cytogenetic band: 17q21.2; and, HGNC cytogenetic band: 17q21. The term STAT3 refers to a human protein that has 770 amino acids and has a molecular weight of about 88,068 Da. The term is inclusive of splice isoforms or variants, and also inclusive of that protein referred to by such alternative designations as: APRF, MGC 16063, Acute-phase response factor, DNA-binding protein APRF, HIES as used by those skilled in the art to that protein encoded by human gene STAT3. The term is also inclusive of the non-human ortholog or homolog thereof.

As used herein, "STAT5," refers to STAT5A and/or STAT5B. If specific reference to either STAT5A or STAT5B is required, the specific term will be used herein.

As used herein, "STAT5A" and "signal transducer and activator of transcription 5A" can be used interchangeably and refer to a transcription factor encoded by a gene designated in human as the STAT5A gene, which has a human gene map locus described by Entrez Gene cytogenetic band: 17q1 1.2; Ensembl cytogenetic band: 17q21.2; and, HGNC cytogenetic band: 17q 1 1.2. The term STAT5A refers to a human protein that has 794 amino acids and has a molecular weight of about 90,647 Da. The term is inclusive of splice isoforms or variants, and also inclusive of that protein referred to by such alternative designations as MGF and STAT5 as used by those skilled in the art to that protein encoded by human gene STAT5A. The term is also inclusive of the non-human ortholog or homolog thereof As used herein, "STAT5B" and "signal transducer and activator of transcription 5B" can be used interchangeably and refer to a a transcription factor encoded by a gene designated in human as the STAT5B gene, which has a human gene map locus described by Entrez Gene cytogenetic band: 17q1 1.2; Ensembl cytogenetic band: 17q21.2; and, HGNC cytogenetic band: 17q1 1.2. The term STAT5A refers to a human protein that has 787 amino acids and has a molecular weight of about 89,866 Da. The term is inclusive of splice isoforms or variants, and also inclusive of that protein referred to by such alternative designations as transcription factor STAT5B as used by those skilled in the art to that protein encoded by human gene STAT5A. The term is also inclusive of the non-human ortholog or homolog thereof.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. In one aspect, the subject is a mammal. A patient refers herein to a subject afflicted with cancer, preferably glioblastoma. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by STAT3 inhibition" means having been subjected to a physical examination by a person of skill, for example, a physician, and found to have a condition that can be diagnosed or treated by a compound or composition that can inhibit or negatively modulate STAT3. As a further example, "diagnosed with a need for inhibition of STAT3" refers to having been subjected to a physical examination by a person of skill, for example, a physician, and found to have a condition characterized by a dysfunction in STAT3 activity. Such a diagnosis can be in reference to a disorder, such as an oncological disorder or disease, cancer and/or disorder of uncontrolled cellular proliferation and the like, as discussed herein. For example, the term "diagnosed with a need for inhibition of STAT3 activity" refers to having been subjected to a physical examination by a person of skill, for example, a physician, and found to have a condition that can be diagnosed or treated by inhibition of STAT3 activity. For example, "diagnosed with a need for modulation of STAT3 activity" means having been subjected to a physical examination by a person of skill, for example, a physician, and found to have a condition that can be diagnosed or treated by modulation of STAT3 activity, e.g. negative modulation. For example, "diagnosed with a need for treatment of one or more disorder of uncontrolled cellular proliferation associated with STAT3 dysfunction" means having been subjected to a physical examination by a person of skill, for example, a physician, and found to have one or disorders of uncontrolled cellular proliferation, e.g. a cancer, associated with STAT3 dysfunction.

As used herein, the expression "STAT3 or STAT5-dependent cancer" refers to a cancer harboring constitutively activated STAT3 or STAT5.

As used herein, the phrase "identified to be in need of treatment for a disorder," or the like, refers to selection of a subject based upon need for treatment of the disorder. For example, a subject can be identified as having a need for treatment of a disorder (e.g., a disorder related to STAT3 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target STAT3 protein, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In some contexts, an $IC_{50}$ can refer to the plasma concentration of a substance that is required for 50% inhibition in vivo, as further defined elsewhere herein. More commonly, $IC_{50}$ refers to the half maximal (50%) inhibitory concentration (IC) of a substance required to inhibit a process or activity in vitro.

As used herein, "STAT3 $IC_{50}$" refers to the concentration of a substance (e.g., a compound or a drug) that is required for 50% inhibition of a STAT3 activity. In some contexts, an $IC_{50}$ can refer to the plasma concentration of a substance that is required for 50% inhibition of an in vivo activity or process as further defined elsewhere herein, e.g. tumor growth in an animal or human. In other contexts, STAT3 $IC_{50}$ refers the half maximal (50%) inhibitory concentration (IC) of a substance or compound required to inhibit a process or activity an in vitro context, e.g. a cell-free or cell-based assay. For example, the STAT3 $IC_{50}$ can be in the context of the half-maximal concentration required to inhibit cell growth. As discussed below, the response is measured in a cell-line with aberrant STAT3 activity. Alternatively, the response is measured in a cell-line with persistently active STAT3. The response can be determined using a cell-line derived from a human breast cancer, human pancreatic cancer, and human prostate cancer. For example, the response can be measured in a cell-line selected from MDA-MB-231, Panc-1, and DU-145. Cell-lines transfected with specific genes can also be used. For example, the response can be measured in a cell-line transfected with v-Src. Alternatively, the cell-line transfected with v-Src is a permanent cell-line. In some cases, the STAT3 $IC_{50}$ is the half-maximal concentration required to inhibit STAT3 activity in a cell-free assay, e.g. an electrophoretic mobility shift assay ("EMSA"). Alternatively, the STAT3 $IC_{50}$ is the half-maximal concentration required to inhibit cell-growth, cell viability or cell migration activity.

As used herein, the term "STAT3 $K_D$" refers to the binding affinity of a compound or substance for the STAT3 determined in an in vitro assay. The $K_D$ of a substance for a protein can be determined by a variety of methods known to one skilled in the art, e.g. equilibrium dialysis, analytical ultracentrifugation and surface plasmon resonance ("SPR") analysis. As typically used herein, STAT3 $K_D$ is defined as the ratio of association and dissociation rate constants determined using SPR analysis using purified STAT3 protein.

As used herein, the term "STAT3 $K_i$" refers to the inhibition constant for the displacement of a STAT3 SH2 probe from STAT3 protein. For example, the STAT3 SH2 can be fluorescence-labelled GpYLPQTV. As described herein, the fluorescence label is 5-carboxyfluorescein, although other suitable fluorescence probes can be used as determined to be useful and convenient by one skilled in the art.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or non-aqueous solutions, dispersions, suspensions or emulsions, as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, butyl, n-pentyl, isopentyl, i-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like. [0086] This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH2)$_a$-, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$—OA$^2$ or —OA$^1$—(OA$^2$)$_a$—OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)2 where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $(A^1O$—$(O)C$-$A^2$-$C(O)O)_a$— or -$(A^1O(O)C$-$A^2$-$OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -$(A^1O$-$A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the $S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$", "$R^2$", "$R^3$", "$R^n$" where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^o$; $-(CH_2)_{0-4}OR^o$; $-O(CH_2)_{0-4}R^o$, $-O-(CH_2)_{0-4}C(O)OR^o$; $-(CH_2)_{0-4}CH(OR^o)_2$; $-(CH_2)_{0-4}Ph$, which may be substituted with $R^o$; $-(CH_2)_{0-4}O(CH_2)_{0-1}Ph$ which may be substituted with $R^o$; $-CH=CHPh$, which may be substituted with $R^o$; $-(CH_2)_{0-4}O(CH_2)_{0-1}$-pyridyl which may be substituted with $R^o$; $-NO_2$; $-CN$; $-N_3$; $-(CH_2)_{0-4}N(R^o)_2$; $-(CH_2)_{0-4}N(R^o)C(O)R^o$; $-N(R^o)C(S)R^o$; $-(CH_2)_{0-4}N(R^o)C(O)NR^o{}_2$; $-N(R^o)C(S)NR^o{}_2$; $-(CH_2)_{0-4}N(R^o)C(O)OR^o$—$N(R^o)N(R^o)C(O)R^o$; $-N(R^o)N(R^o)C(O)NR^o{}_2$; $-N(R^o)N(R^o)C(O)OR^o$; $-(CH_2)_{0-4}C(O)R^o$; $-C(S)R^o$; $-(CH_2)_{0-4}C(O)OR^o$, $-(CH_2)_{0-4}C(O)SR^o$; $-(CH_2)_{0-4}C(O)OSiR^o{}_3$; $-(CH_2)_{0-4}OC(O)R^o$; $-OC(O)(CH_2)_{0-4}SR-$; $SC(S)SR^o$; $-(CH_2)_{0-4}SC(O)R^o$; $-(CH_2)_{0-4}C(O)NR^o{}_2$; $-C(S)NR^o{}_2$; $-C(S)SR^o$; $-SC(S)SR^o$, $-(CH_2)_{0-4}OC(O)NR^o{}_2$; $-C(O)N(OR^oR^o)$; $-C(O)C(O)R^o$; $-C(O)CH_2C(O)R^o$; $-C(NOR^oR^o)$; $-(CH_2)_{0-4}SSR^o$; $-(CH_2)_{0-4}S(O)_2R^o$; $-(CH_2)_{0-4}S(O)_2OR^o$; $-(CH_2)_{0-4}OS(O)_2R^o$; $-S(O)_2NR^o{}_2$; $-(CH_2)_{0-4}S(O)R^o$; $-N(R^o)S(O)_2NR^o{}_2$; $-N(R^o)S(O)_2R^o$; $-N(OR^oR^o)$; $-C(NH)NR^o{}_2$; $-P(O)_2R^o$; $-P(O)R^o{}_2$; $-OP(O)R^o{}_2$; $-OP(O)(OR^o)_2$; $SiR^o{}_3$; $-(C_{1-4}$ straight or branched)alkylene) $O-N(R^o{}_2)$; or $-(C_{1-4}$ straight or branched)alkylene)$C(O)ON(R^o{}_2)$, wherein each $R^o$ may be substituted as defined below and is independently hydrogen, $C_{1-6}$ aliphatic, $-CH_2Ph$, $-O(CH_2)_{0-1}Ph$, $-CH_2-(5-6$ membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $-(CH_2)_{0-2}R^*$, -(haloR*), $-(CH_2)_{0-2}OH$, $-(CH_2)_{0-2}OR^*$, $-(CH_2)_{0-2}CH(OR^*)_2$; $-O(haloR^*)$, $-CN$, $-N_3$, $-(CH_2)_{0-2}C(O)R^*$, $-(CH_2)_{0-2}C(O)OH$, $-(CH_2)_{0-2}C(O)OR^*$, $-(CH_2)_{0-2}SR^*$, $-(CH_2)_{0-2}SH$, $-(CH_2)_{0-2}NH_2$, $-(CH_2)_{0-2}NHR^*$, $-(CH_2)_{0-2}NR^*{}_2$, $-NO_2$, $-SiR^*{}_3$, $-OSiR^*{}_3$, $-C(O)SR^*$, $-(C_{1-4}$ straight or branched alkylene)$C(O)OR^*$, or $-SSR^*$ wherein each $R^*$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^*$ include=0 and =S.

Suitable divalent substituents on a saturated carbon atom of an "optionally substituted" group include the following: =O, =S, =NNR*$_2$, =NNHC(O)R*=NNHC(O)OR*, =NNHS(O)$_2$R*, =NR*, =NOR*—O(C(R*$_2$))$_{2-3}$O— or —S(C(R*$_2$))$_{2-3}$S— wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*{}_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^*$, -(haloR*), $-OH$, $-OR^*$, $-O(haloR^*)$, $-CN$, $-C(O)OH$, $-C(O)OR^*$, $-NH_2$, $-NHR^*$, $-NR^*{}_2$, or $-NO_2$, wherein each $R^*$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^+$, $-NR^+{}_2$, $-C(O)R^+$, $-C(O)OR^+$, $-C(O)C(O)R^+$, $-C(O)CH_2C(O)R^+$, $-S(O)_2R^+$, $-S(O)_2NR^+{}_2$, $-C(S)NR^+{}_2$, $-C(NH)NR^+{}_2$, or $-N(R^+)S(O)_2R^+$; wherein each $R^+$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^+$, taken together with their intervening atom(s) form an unsubstituted 3-12-membered saturated, partially unsaturated, or aryl mono- or bicyclic ring having 0-4 heteroatoms independently selected from nitrogen, oxygen or sulfur.

Suitable substituents on the aliphatic group of R. are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet{}_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides—including chloro, bromo, and iodo—and pseudohalides (sulfonate esters)—including triflate, mesylate, tosylate, and brosylate. It is also contemplated that a hydroxyl moiety can be converted into a leaving group via Mitsunobu reaction.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{35}S$, $^{18}F$ and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as H and C are incorporated, are useful in drug and/or substrate tissue distribution assays. Tritiated, i.e., $^3$H, and carbon-14, i.e., u isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

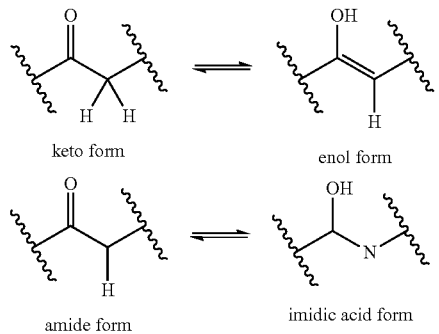

Likewise, amides with an N-hydrogen can exist in equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

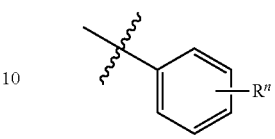

which is understood to be equivalent to a formula:

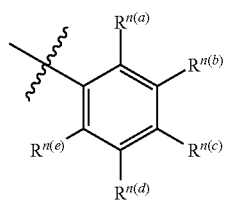

wherein n is typically an integer. That is, $R^n$ is understood to represent five independent substituents, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

In one aspect, the invention relates to compounds useful as inhibitors of STAT3/STAT5. In a further aspect, the disclosed compounds and products of disclosed methods of making are modulators of STAT3/STAT5 activity. In various aspects, the present invention relates to compounds that bind to a STAT3 protein and negatively modulate STAT3 activity. In other various aspects, the present invention relates to compounds that bind to a STAT5 protein and negatively modulate STAT5 activity. In a further aspect, the disclosed compounds exhibit inhibition of STAT3/5 activity.

In one aspect, the compounds of the invention are useful in the treatment of cancer associated with STAT3/STAT5 activity dysfunction, such as breast, prostate or brain cancer and glioblastoma, and other diseases in which a STAT3/5 protein is involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In an aspect of the disclosure, there is provided a compound of formula I

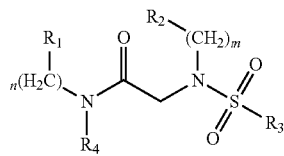

or a pharmaceutically acceptable salt, solvate or prodrug thereof, wherein each of m and n are independently an integer from 0-3;

wherein $R^1$ is selected from $A^1$, $A^2$, $-(A^1)-(A^2)$, $-(A^2)-(A^3)$, $-(A^3)-(A^2)$, $-(A^3)-(A^4)$, $-(A^5)-(A^1)-(A^7)$, $-(A^5)-(A^2)-(A^8)$, $-(A^5)-(A^3)-(A^7)$, and $-(A^5)-(A^6)-L-(A^7)$; wherein $A^1$ is $C_{3-6}$ cycloalkyl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R^5$, $(C=O)OR^5$, and $(C=O)NHR^5$; wherein $A^2$ is $C_{3-6}$ cycloalkyl or heterocycloalkyl, substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R6$, $(C=O)OR6$, and $(C=O)NHR6$; wherein $A^3$ is aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R7$, $(C=O)OR7$, and $(C=O)NHR7$; wherein $A^4$ is aryl, and substituted with 1-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R8$, $(C=O)OR8$, and $(C=O)NHR8$; wherein $A^5$ is selected from $C_{3-6}$ cycloalkyl, $C_{3-6}$ heterocycloalkyl, and aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-4}$-alk-$(C_{1-4}$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R9$, $(C=O)OR9$, and $(C=O)NHR9$; wherein $A^6$ is selected from $C_{3-6}$ cycloalkyl, $C_{3-6}$ heterocycloalkyl, and aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R10$, $(C=O)OR10$, and $(C=O)NHR10$; wherein $A^7$ is selected from $C_{3-6}$ cycloalkyl, $C_{3-6}$ heterocycloalkyl, and aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R11$, $(C=O)OR11$, and $(C=O)NHR11$; wherein $A^8$ is selected from $C_{3-6}$ cycloalkyl, $C_{3-6}$ heterocycloalkyl, and aryl, and substituted with 0-3 groups selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)R12$, $(C=O)OR12$, and $(C=O)NHR12$; wherein L is selected from $-(C=O)-$ and $-SO_2-$; wherein $R^2$ is selected from $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, $C_{1-6}$ polyhaloalkyl, $C_{2-6}$ polyhaloalkenyl, $C_{2-6}$ polyhaloalkynyl; or wherein $R^2$ is aryl, and substituted with 0-5 groups independently selected from halo, hydroxyl, amino, nitro, cyano, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylthio, $C_{1-6}$ haloalkythio, $C_{1-6}$ polyhaloalkylthio, $C_{1-6}$ alkylamino, $C_{1-6}$ dialkylamino, $(C_{1-6})$-alk-$(C_{1-6})$-alkoxy, $(C_{1-6})$-alk-$(C_{1-6})$-haloalkoxy, $(C_{1-6})$-alk-$(C_{1-6})$-polyhaloalkoxy, $(C_{1-6})$-alk-$(C_{1-6})$-alkylthio, $(C_{1-6})$-alk-$(C_{1-6})$-haloalkythio, $(C_{1-6})$-alk-$(C_{1-6})$-polyhaloalkylthio, $CO_2H$, $(C=O)OR12$, and $(C=O)NHR12$; wherein $R^3$ is aryl substituted with 0-5 groups independently selected from halo, hydroxyl, amino, nitro, cyano, $C_{1-6}$ alkyl, $C_{1-6}$ haloalkyl, $C_{1-6}$ polyhaloalkyl, $C_{1-6}$ alkoxy, $C_{1-6}$ haloalkoxy, $C_{1-6}$ polyhaloalkoxy, $C_{1-6}$ alkylamino, $C_{1-6}$ dialkylamino, $(C_{1-6})$-alk-$(C_{1-6})$-alkoxy, $(C_{1-6})$-alk-$(C_1$-6)-haloalkoxy, and $(C_{1-6})$-alk-$(C_{1-6})$-polyhaloalkoxy; wherein each of R5, R6, R7, R8, R9, R10, R11, and $R^{11}$ is independently selected from hydrogen, $C_{1-6}$ alkyl, $C_{1-6}$ haloalkyl, and $C_{1-6}$ polyhaloalkyl; or a pharmaceutically acceptable salt, hydrate, solvate, or polymorph thereof, wherein R2 is selected from the group consisting of:

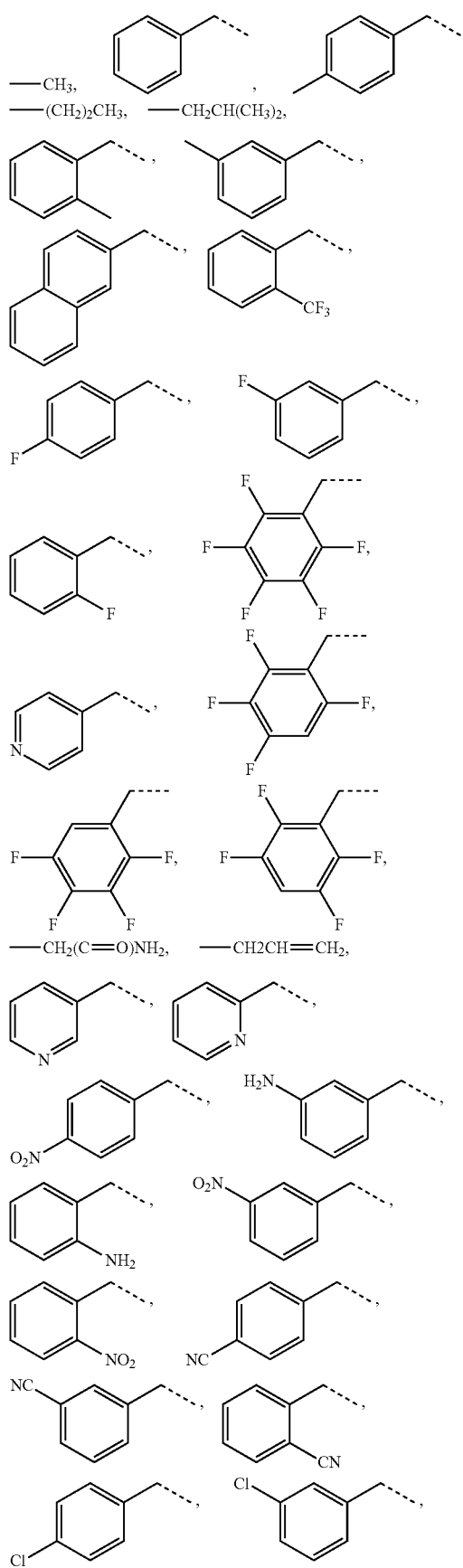
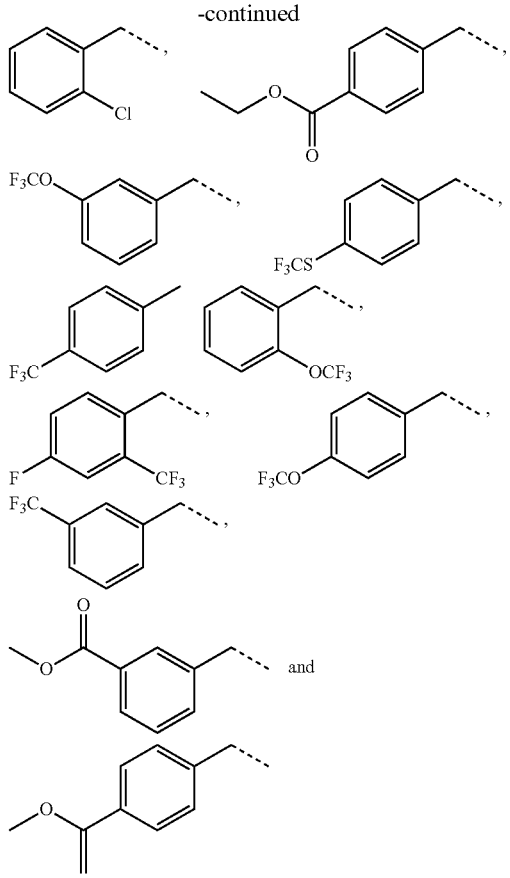
Wherein $R_3$ is selected from the structure represented by formula:
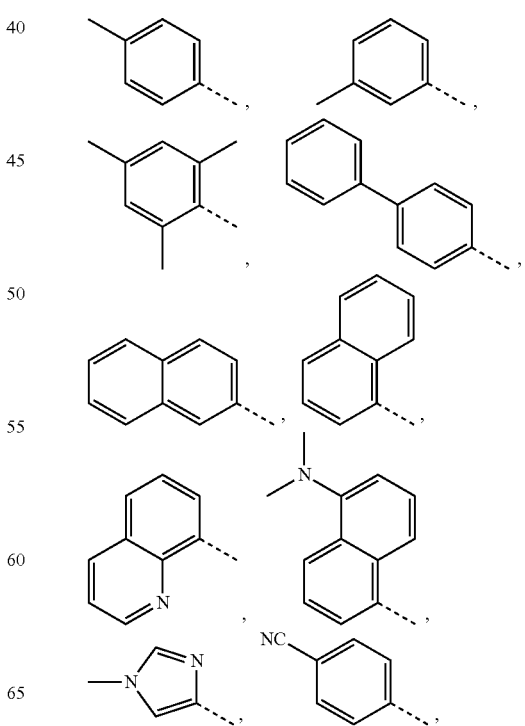

-continued

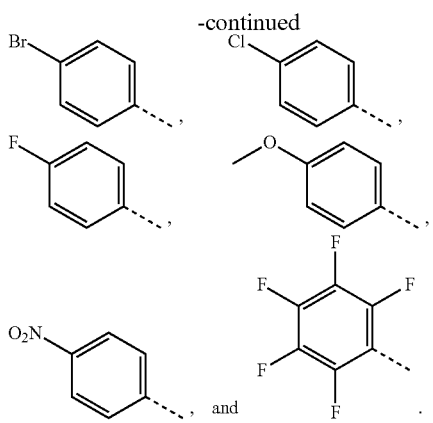

Wherein R⁴ is a structure represented by formula:

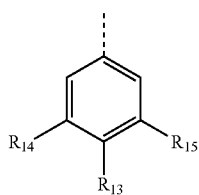

wherein $R^{13}$ is selected from the group consisting of OH, $COR^{16}$, —CN, —$CH_2PO(OH)_2$, —$CH_2P(O)_3(CH_2CH_3)_2$, —$NO_2$, —$NHR^{17}$, and 1H-tetrazole;

$R^{16}$ is selected from the group consisting of: —OH, —$OCH_2OC(O)CH_3$, —$OCH_2OC(O)$t-Butyl, and —NHOH, $R^{17}$ is selected from the group consisting of: —H, —C(O)C(O)$CH_2CH_3$, —C(O)C(O)OH, and —C(O)$CH_2$-1H-tetrazole $R^{14}$ is —H or when $R^{13}$ is COOH, $R^{14}$ is —F, —OC(O)$CH_3$; and $R^{13}$ is —H when $R^{14}$ is OH or both $R^{14}$ and $R^{15}$ are —COOH.

In an aspect of the disclosure, there is provided a focused library of 4-(2-(phenylsulfonamido)acetamido)salicylic acid analogs possessing both prodrugs, potential bioisosteres, as well as functionality deemed appropriate for salicylic acid mimicry. These compounds are tested for their inhibitory activity of STAT3/5. These two proteins have been shown to be involved in various cancers. In will be demonstrated herein that the compounds of the present invention, in comparison to other compounds that are known to be useful for treating various cancers are in fact more potent. With consideration for improving cell and BBB permeability, prodrugs designed herein were synthesized to conceal either one of, or both of, the anionic hydroxyl and carboxylic acid of the salicylic group. In this sub-family, alkyl (39-40), acetoxymethyl (AOM) (26), pivaloyloxymethyl (POM) (27), and the acetylated prodrug (22, 23) of the salicylic acid were prepared to enhance cell permeability (Table 1). In addition to salicylic acid, a phosphotyrosine-like phosphonate derivative of 1 was prepared, 21 and the prodrug analog, 20. For purposes of developing a structure activity relationship, the relative ring positions of the hydroxy- and carboxylate groups were inversed (38), the hydroxyl substituent replaced with a fluoride (33, 43) or removed entirely and replaced with a hydrogen atom (31, 42). The electronegative fluorinated analogs, 33, 43, were prepared to lower inhibitor polarity by reducing the charge on carboxylate and thus, for improving cell permeability. As an additional benefit, the hydroxyl group deletion or replacement with fluorine would preclude phase II glucoronidation. To further investigate the role of the salicylic acid in binding STAT5, an N-hydroxyl amino (32, 44), sulfonamide (12-15), sulfonamine (16), tetrazole (35, 41) and N-hydroxy-oxamic acid (28, 46) derivatives were prepared. Selected prodrug analogs of the bioisosteres were also prepared (17-18). Compounds 12-13 and 36, possessing bulky hydrophobic naphthyl group or benzene, respectively, lacking the key salicylic acid, and were synthesized as negative controls. Chemical synthetic routes toward all compounds shown are reported herein.

TABLE 1

A focused library of inhibitors consisting of prodrugs and bioisosteres of the salicylic acid functionality.

| # | R₄ | R₃ |
|---|-----|-----|
| 8 | ![4-nitrophenyl] NO₂ | ![pentafluorophenyl] F,F,F,F,F |
| 9 | ![4-nitrophenyl] NO₂ | ![4-methylphenyl] |
| 10 | ![4-aminophenyl] NH₂ | ![pentafluorophenyl] F,F,F,F,F |
| 11 | ![4-aminophenyl] NH₂ | ![4-methylphenyl] |

TABLE 1-continued

A focused library of inhibitors consisting of prodrugs and bioisosteres of the salicylic acid functionality.

| # | R₄ | R₃ |
|---|----|----|
| 12 | 4-(naphthalene-1-sulfonamido)phenyl | pentafluorophenyl |
| 13 | 4-(quinoline-5-sulfonamido)phenyl | pentafluorophenyl |
| 14 | 4-(methanesulfonamido)phenyl | pentafluorophenyl |
| 15 | 4-(1-methyl-1H-imidazole-4-sulfonamido)phenyl | pentafluorophenyl |
| 16 | 4-(sulfamoylamino)phenyl | pentafluorophenyl |
| 17 | 4-[(ethoxyoxalyl)amino]phenyl | pentafluorophenyl |

TABLE 1-continued
A focused library of inhibitors consisting of prodrugs and bioisosteres of the salicylic acid functionality.
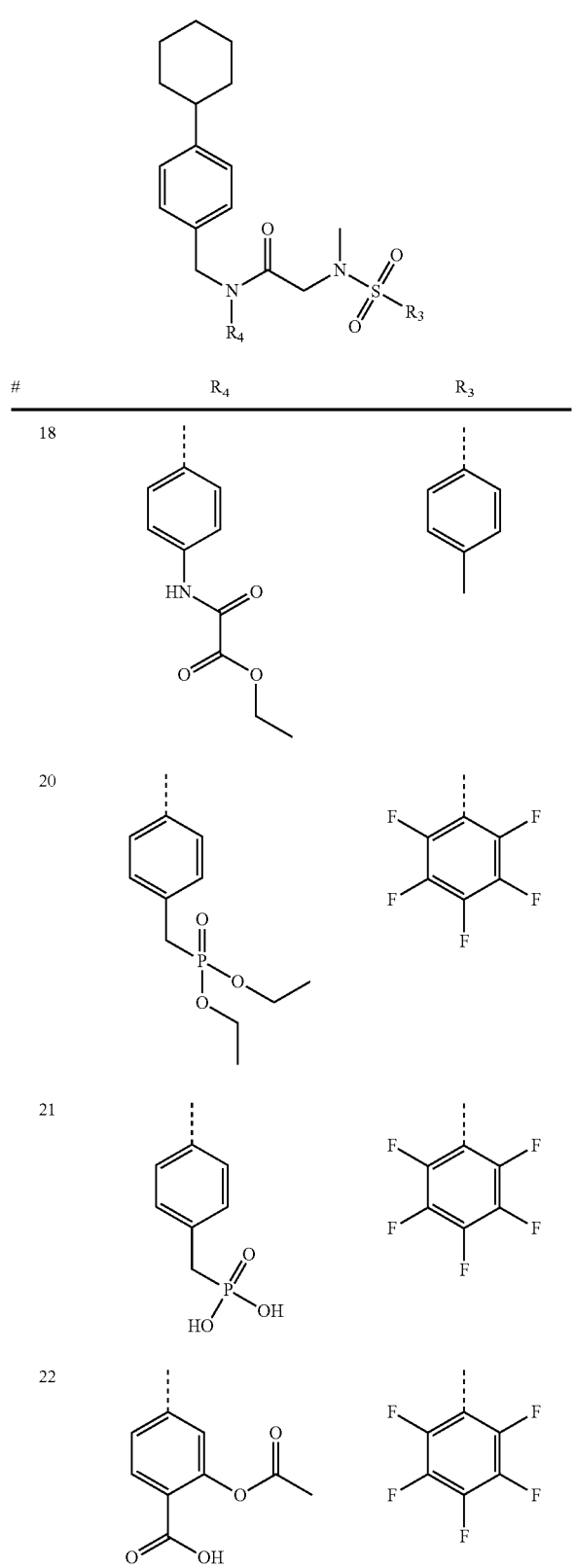
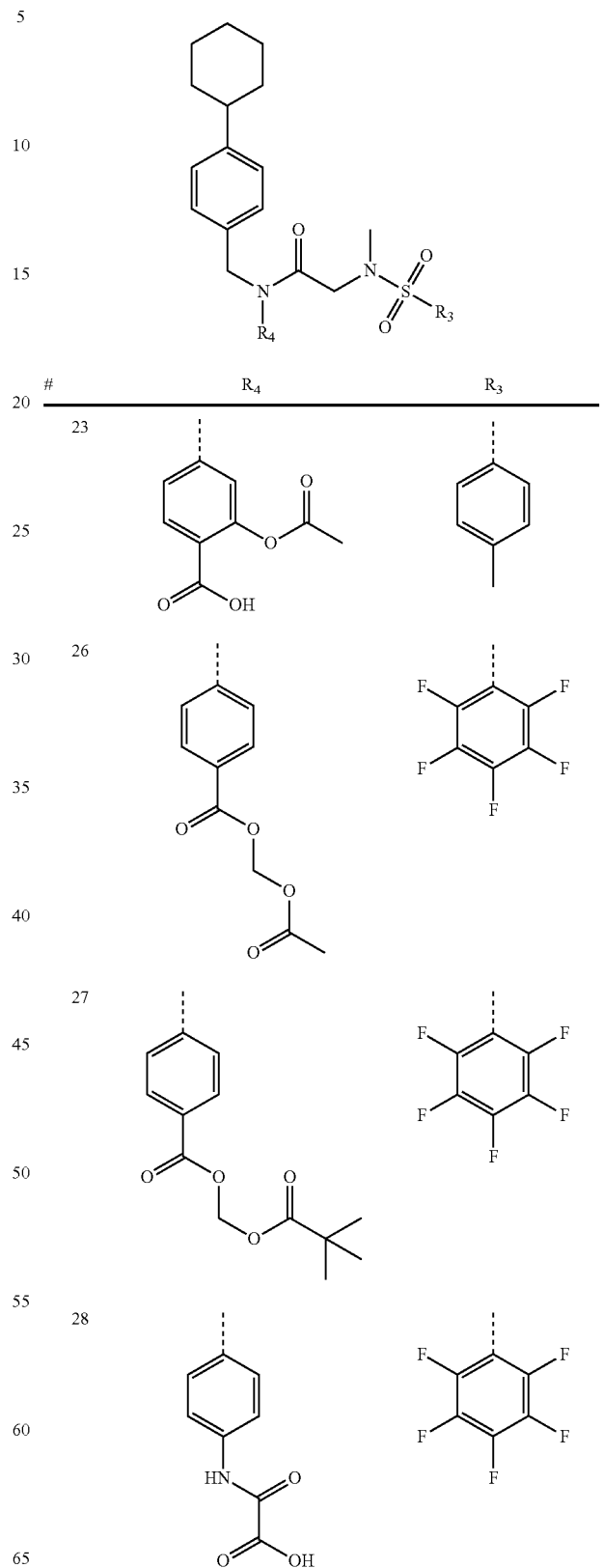

TABLE 1-continued
A focused library of inhibitors consisting of prodrugs and bioisosteres of the salicylic acid functionality.
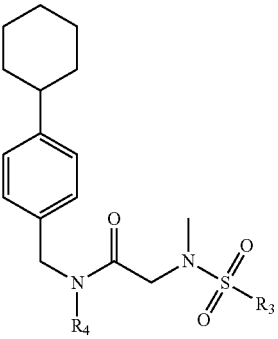
| # | R4 | R3 |
|---|----|----|
| 29 | 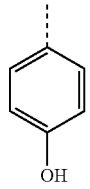 | 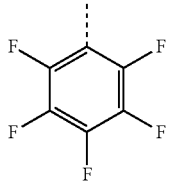 |
| 30 | 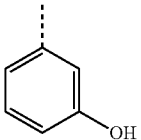 | 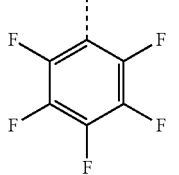 |
| 31 | 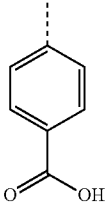 | 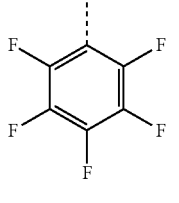 |
| 32 | 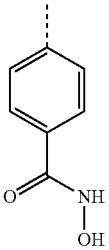 | 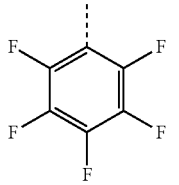 |
| 33 | 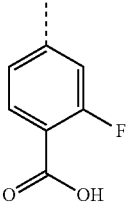 | 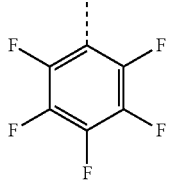 |
TABLE 1-continued
A focused library of inhibitors consisting of prodrugs and bioisosteres of the salicylic acid functionality.
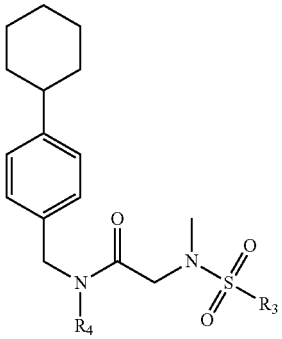
| # | R4 | R3 |
|---|----|----|
| 34 | 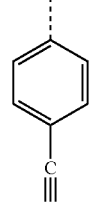 | 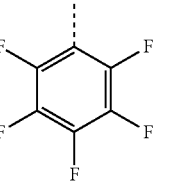 |
| 35 | 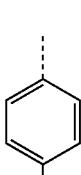 | 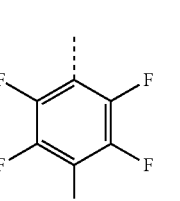 |
| 36 | 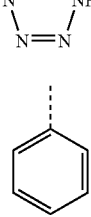 | 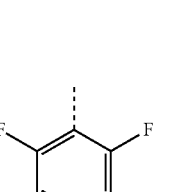 |
| 37 |  | 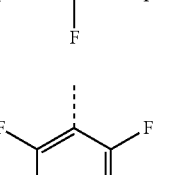 |
| 38 | 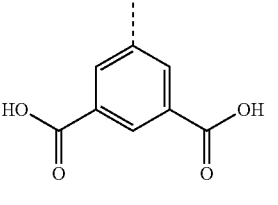 | 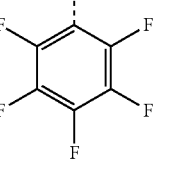 |

TABLE 1-continued

A focused library of inhibitors consisting of prodrugs and bioisosteres of the salicylic acid functionality.

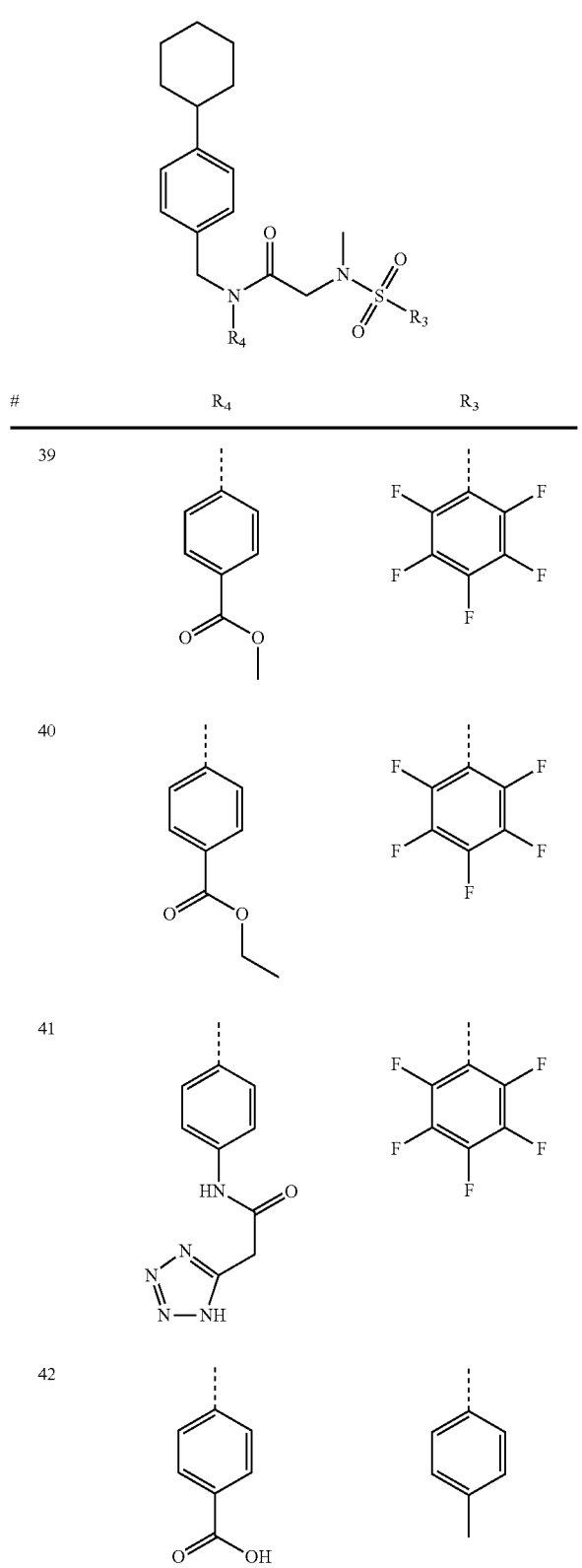
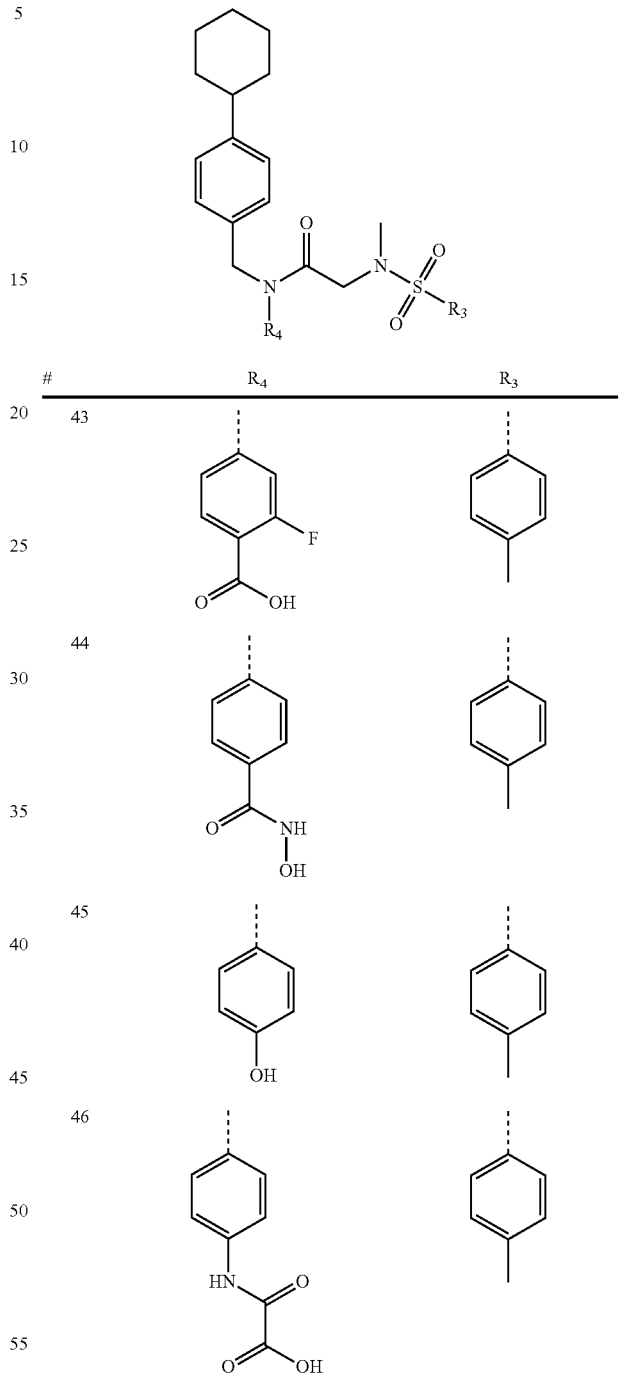

First, the library was screened for biological activity against a set of three representative GBM BTSCs derived from GBM patients, including the very aggressive GBM BTSC lines, BTSC73M, BTSC30M and BTSC68EF. Dissociated BTSC spheres were seeded at 1500 cells/96-well and treated with drug compound or vehicle (DMSO) one day after plating. Cell viability following drug treatment was assessed after 72 hrs using the ALAMARBLUE™ assay (Invitrogen) according to the manufacturer's instructions. All culture experiments were performed in triplicate with a minimum of three wells per condition. $IC_{50}$ values obtained from the results of these experiments were compared to BP-1-102 compound (also referred in these experiments as compound 1), and Cucurbitacin, a JAK2 inhibitor and the most potent inhibitor of BTSCs to date, as references (Table 2).

TABLE 2

| | $IC_{50}$ (µM) data | |
|---|---|---|
| | 30M | 73M |
| WP1066 | 1.8 ± 0.22 | 2.1 - wide error |
| Cucurbitacin 1 | 0.63 ± 0.08 | 0.70 ± 0.06 |
| Compound 31 | 0.432 ± 0.022 | 1.031 ± 0.031 |

Figure 1B:
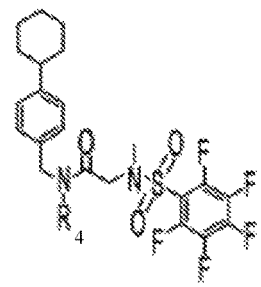
FIG. 1B is a table illustrating the $IC_{50}$ values from the compounds tested in FIG. 1A against BTSCs, 25EF, 67EF, 73E, 84EF, and 127EF.

However, poor BBB permeability has negated Cucurbitacin's clinical relevance. Consistent with findings in other tumour cells harbouring activated STAT3, compound 1 exhibited low µM activity (FIG. 1A). Most encouragingly, the library prepared exhibited a number of more potent inhibitors that exhibited low nanomolar (nM) $IC_{50}$ cytotoxicity values against BTSCs, including unprecedented activity against 73M. Of note, the tolyl analogs ($R_2$=tolyl, 18, 23, 42-46) were poorly soluble and exhibited much reduced activity cf the pentafluorobenzene $R_2$ counterparts which gave homogenous solutions. The top four ranked compounds, 22, 31, 32, and 33, which displayed $IC_{50}$ values ranging from 100 nM to 3.8 µM were further investigated against BTSCs, 25M, 67EF, 73EF, 84EF and 127EF which represent the molecular heterogeneity of human GBMs (FIGS. 1A and 1B). Across, all 8 BTSCs evaluated, compounds 22 and 31-33 showed remarkable activity, with $EC_{50}$s ranging from 66-1145 nM. However, of the top four agents evaluated, compound 31, equipped with a benzoic acid substituent, exhibited significantly higher potency against a larger number of BTSCs. Most notably, against 127EF, 31, with an $EC_{50}$ 66±33.9 nM, represents the most potent small molecule inhibitor of a BTSC, more potent even than Cucurbitacin ($EC_{50}$=630 nM and 700 nM v.s. 30M and 73M respectively).

Figure 2A:
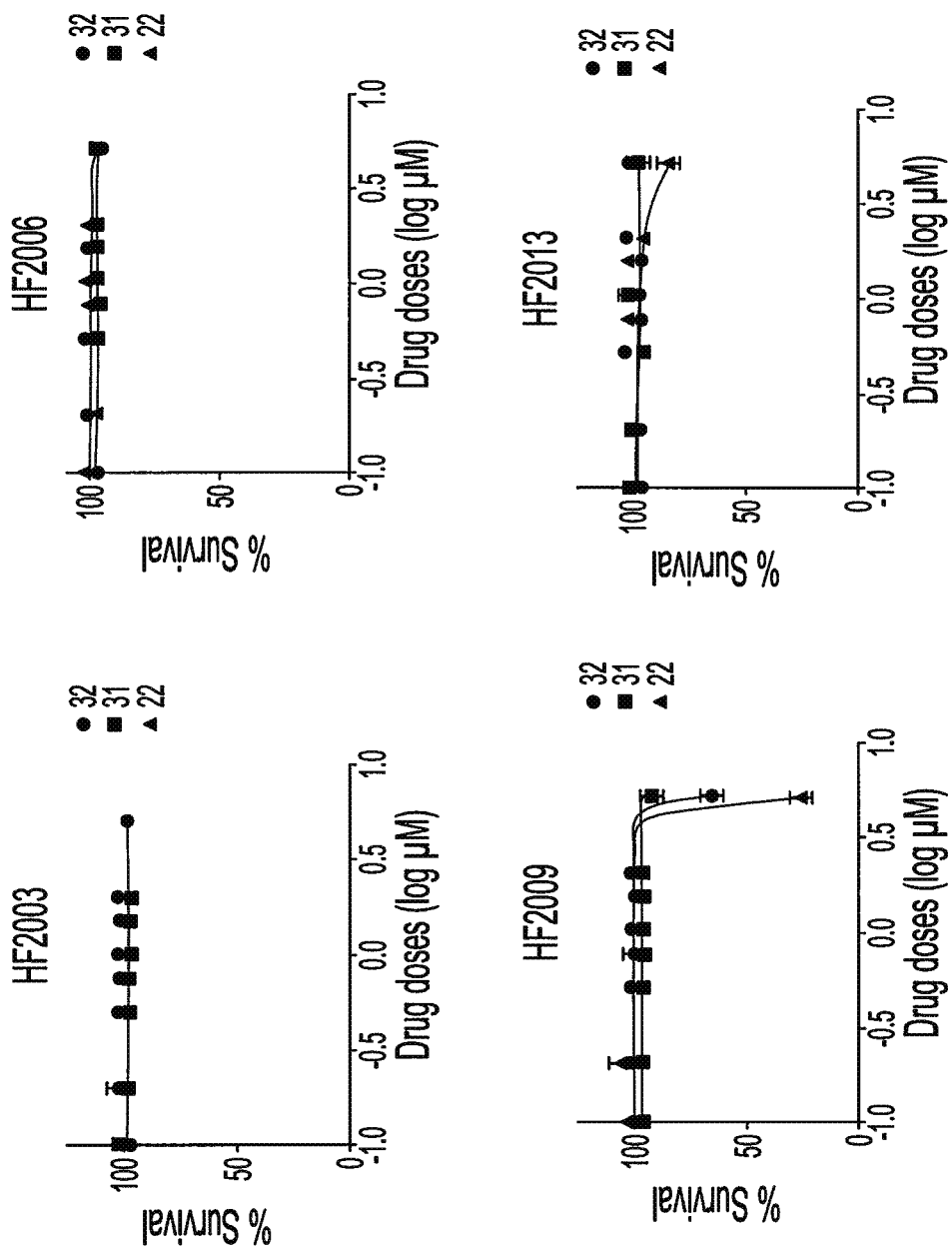
FIG. 2A illustrates the insensitivity of a number of compounds against a variety of kinases and structural proteins.

Given the nM cytoxicity, these compounds were assayed for biological effects in healthy cells. A series of normal human fetal astrocytes (HF 2003, HF 2006, HF 2009, HF 2013), were subjected to top three inhibitors at concentrations up to 5 µM (10-20 fold higher than reported $IC_{50}$s against BTSCs). As shown in FIG. 2A, compounds 22, 31 and 32 showed minimal toxicity at concentrations of up to 5 µM in normal human cells, identifying a clear therapeutic window for these agents in GBM.

Figure 2B:
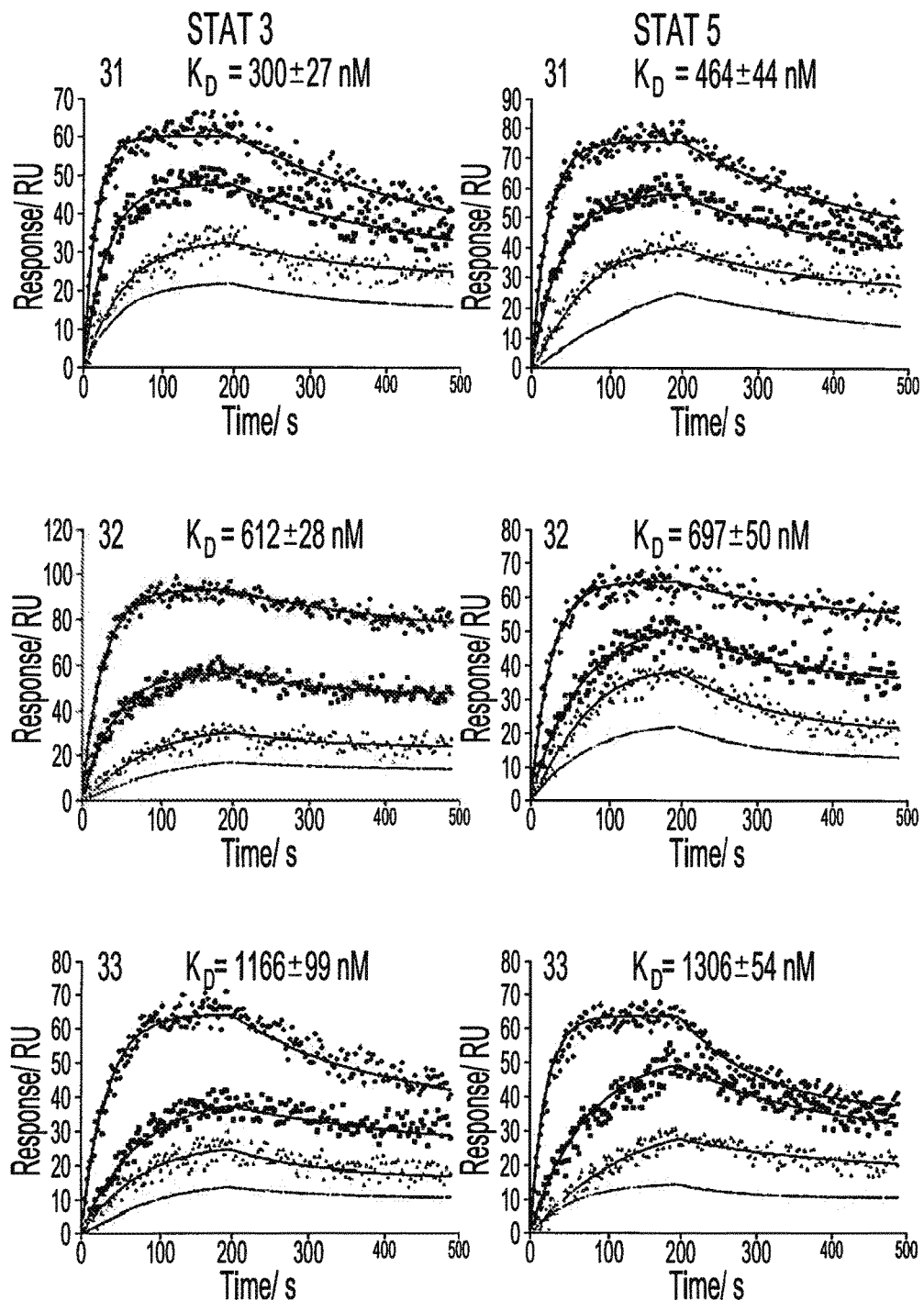
FIG. 2B illustrates SPR curves displaying the binding affinity of the best hits to STAT3/5 proteins.

Next, to confirm retention of STAT3 binding affinity, surface plasmon resonance (SPR) binding experiments were performed using a ProteOn XPR36 (Bio-rad). Briefly, full length His-tagged STAT3 protein (SignalChem) was immobilized onto THE sensor chip (bio-Rad, Ontario, Canada). To determine the kinetic association and dissociation rate constants ($k_{on}$ and $k_{off}$), drug-protein binding was evaluated at varying concentrations. Most encouragingly, all four compounds exhibited potent nM binding potencies (FIG. 2B). Compound 31 was shown to be the most potent binder, with a $K_D$ ($k_{off}/k_{on}$)=300±27 nM. Thus, with the results reported above, when compared to what exists in the prior art, compound 31 represents the most potent, non-phosphorylated STAT3 inhibitor reported to-date, with low nM $K_D$ values against STAT3 protein. Studies reported on FIG. 2B were done at multiple concentrations, i.e. 5.000, 1.667, 0.556, and 0.185 µM.

Next, to examine disruption of phosphopeptide:STAT3 SH2 domain complexation events, compounds were subjected to a fluorescence polarization (FP) assay as previously reported by Schust, J., et al. (Anal. Biochem. 330, 114-118, 2004) and Wu, P. et al. (Anal. Biochem. 249, 29-36, 1997). Briefly, fluorescein labeled peptide probe (5-FAM-GpYLPQTV-NH$_2$ (CanPeptide) was incubated with STAT3 protein (SignalChem) and inhibitor for 30 minutes and then analyzed on a Tecan M1000 fluorimeter (Tecan). Polarized fluorescence was plotted against concentration of inhibitor and $IC_{50}$ values determined by fitting to a dose response curve. Relative to compound 1, many of the new derivatives showed improved binding activity. As expected, in an extracellular setting, prodrug analogs, 17-20, 22, 26-27 and 39-40 displayed no binding activity. In addition, negative control 36, lacking the salicylic acid binding group, showed no disruption of the STAT3:phosphopeptide interaction. Compounds possessing the neutral amidosulfonamide substituent exhibited lower inhibitory potency. Substitution with a hydroxyl-amine (32) showed marked improvements in inhibitory potency. Finally, and in good agreement with SPR data, compound 27 was the most potent inhibitor of STAT3. In addition, 31 displayed a >5 fold selectivity for STAT3 and STAT5 over STAT1 which has anti-tumor roles.

Cellular levels of activated STAT3 activity were determined using Western blot analyses for phosphorylated STAT3, including, Y705 as well as pSTAT3 S727 and downstream target genes, Bcl-xL and Cyclin D1. Blockade of the STAT3 SH2 domain should not inhibit S727 phosphorylation, only Y705. For protein analysis following drug treatment, BTSC spheres were dissociated to single cells and 1×10$^6$ cells were treated with drug or vehicle (DMSO) at different concentrations and time points. 15 µg of protein were loaded on 7.5% or 10% SDS-PAGE gels and transblotted to nitrocellulose membranes. Blots were stained with antibodies: phospho-Y705, phospho-5727, Bcl-xL, cyclin D1, PARP and Actin. Bands were visualized with the ECL PLUS Western Blotting Detection System and HYPERFILM™ (Amersham). Most encouragingly, at 1 µM, the top four compounds exhibited potent suppression of pSTAT3 (Y705) with no effect on the total STAT3 concentrations or on pSTAT3 S727 (levels). In addition, off-target effects were not observed against kinase targets including, MAPK or EGFR, as well as structural protein, β-tubulin. Notably, compounds 22, 31 and 32 showed the most suppression of pSTAT3 (Y705). To determine whether the observed biological responses were STAT3 concentration dependant, and further, to establish the exact pSTAT3 inhibition potency selected BTSCs were treated to varying concentrations of lead inhibitors (0, 0.1, 0.5, 1.0 and 5.0 µM) and lysates subjected to Western Blot analysis. Most encouragingly, dose-dependent decreases in pSTAT3 levels were observed, as well as potent inhibition of downstream targets involved in cell growth and survival, Cyclin D1 and Bcl-xL. Most notably, compound 31, the most potent compound against BTSCs, exhibited concentration-dependant decreases in pSTAT3 levels that correlated well with observed cytotoxicity and downstream target suppression. Specifically, treatment with compound 31 at 500 nM completely silenced pSTAT3 signalling. Compounds 22 and 32, whilst slightly less potent, still exhibited nM inhibition of pSTAT3.

To further evaluate potential off-target effects, compounds 22, 31 and 32 were screened in vitro for activity against five cancer related kinases, c-Src, ERK1, AKT, JaK1 and JaK2 at 5 µM (10-15 fold higher than reported $IC_{50}$s against BTSCs). Briefly, this assay employs a radiometric detection system to measure kinase phosphoryl transfer activity. The top three inhibitors exhibited moderate to negligible activity against the bank of kinases. For example, all three compounds showed negligible inhibition of Akt1, Erk1 and JaK1, whilst only exhibiting modest inhibition of c-Src and JaK2 (~50% inhibition of kinase activity). Thus, since the concentration of inhibitor required to elicit effective kinase inhibition was 15-fold higher than the $IC_{50}$ values in BTSCs. It thus shows that the biological activity was not a result of upstream JaK kinase inhibition.

Figure 3:
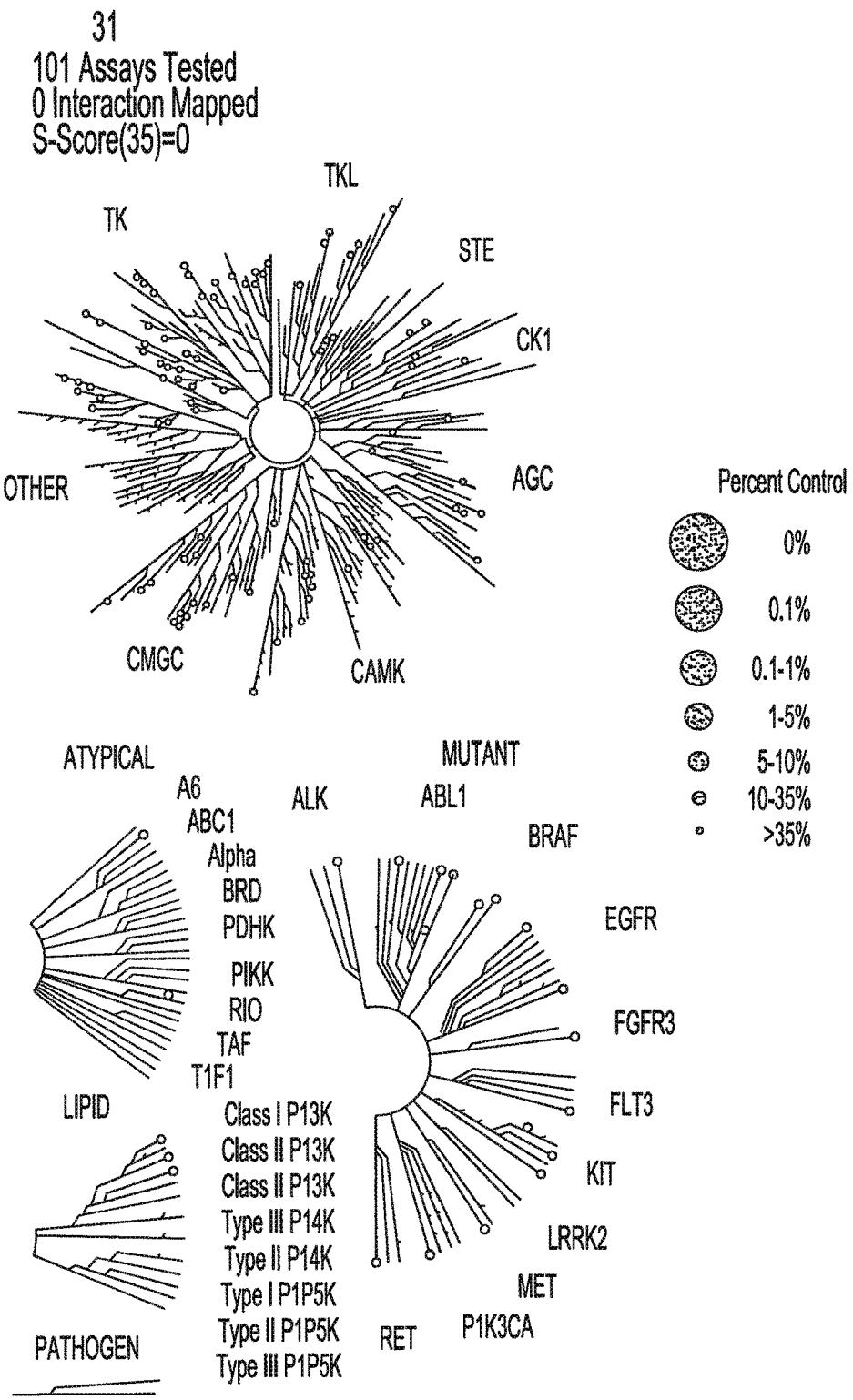
FIG. 3 illustrates a treespot dendrogram displaying that compound 31 does not inhibit any of the 101 kinases tested against, a hit being defined as >35% inhibition.

To more comprehensively investigate potential off-target effects, 31 was subjected to a kinome screen (101 diverse kinases, DISCOVERX™ KINOMEscan) as well as a protein and receptor screen (21 biologically important G protein-coupled receptors (GPCRs)). For kinome screening kinases labelled with DNA were treated with compound 31 (500 nM) and incubated with an immobilized ligand designed to capture the target kinase. Ultra-sensitive quantitative PCR (qPCR) was used to measure levels of immobilized kinases after treatment with compound 31. The immobilized kinase levels were compared to control samples and hits were designated when the quantity of the seized kinase fell below a 35% threshold. The GPCR screening employed the widely applied PathHunter β-arrestin GPCR assay platform (DISCOVERX™) to evaluate the activity of compound 31. The GPCRs are widely regarded as a most important family of membrane receptors, due to their master regulatory role in intracellular signal transduction. As a result, GPCRs are among the most heavily investigated drug targets in the pharmaceutical industry. Encouragingly, compound 32, showed no off-target activity against any of the 21 GPCRs tested (500 nM). Moreover, compound 31 at same concentration (500 nM), showed negligible effects against the representative family of kinases including a large number of both SH2 (JaK1 and JaK2) and SH3 (Fes, Fer, Fyn) domain-containing kinases. Lack of off-target kinase activity is illustrated in the TreeSpot dendrogram (FIG. 3). Since there exists an estimated 117 SH2 and 300 SH3 domains, it was important that compound 31 display relative selectivity for the target STAT3 SH2 domain, minimizing undesired off-target biological effects. Taken together, compound 31 exhibited unprecedented cytotoxicity across a range of human BTSCs, exhibited no toxicity in human fetal astrocytes at concentrations 15-20-fold higher than $IC_{50}$s, potently suppressed pSTAT3 at nM concentrations correlating well with in vitro nM $K_D$ values (SPR), inhibited STAT3's downstream targets and showed no discernible off-target effects at therapeutic doses as assessed by kinome and GPCR screens.

Figure 4:
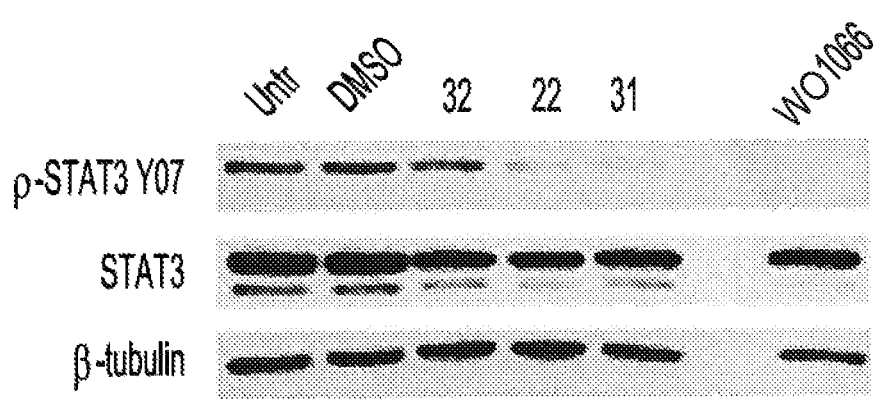
FIG. 4 illustrates a Western blot analysis of the top three compounds against BTSC 147M and their comparison against a well-established Jak2 inhibitor WP1066 at 1 µM against BTSCM 73M.

Finally, to establish inhibitors clinical relevance, compound 31's activity was compared against a leading JaK2 inhibitor, WP1066, in 73M, one of the most aggressive BTSC (FIG. 4). Comparative Western blot analyses demonstrated equipotent pSTAT3 suppression at 1 μM inhibitor concentrations. However, it should be noted that upstream JaK kinase inhibitors have suffered from lack of kinase selectivity and poor in vivo efficacy, including blood brain barrier permeability. As noted previously, the compounds reported herein do not inhibit the JaKs at therapeutic doses and appear to function through STAT3 direct inhibition.

In summary, the most potent, non-phosphorylated, direct-binding, STAT3 SH2 domain inhibitors has been synthesized and tested herein. Moreover, their application in GBM BTSCs, recently reported to harbor high levels of hyperactivated STAT3, which critically, has been shown to be the major driver in brain cancer tumourogenesis and BTSC drug resistance, has been validated. Compound 31 displayed the highest STAT3 binding affinity for a non-phosphorylated, drug-like, small molecule inhibitor (SPR, $K_D$=315 nM), and it was shown to effectively disrupt STAT3/phosphopeptide interactions. Additionally in whole cell studies, the inhibitors presented herein effectively suppress STAT3 phosphorylation and its downstream protein targets (Cyclin D1 and Bcl-xL). The potential of STAT3 inhibitors have now been clearly demonstrated for the first time for the treatment of BTSCs and its clinical efficacy for GBM clinical application.

Having brought light herein on new potent STAT3 inhibitors, where mimetics of the salicylic acid were tested. However, the inventors have also tested other STAT3 inhibitors as reported in WO2012/018868. These specific compounds are substituents on $R^4$ from formula 1 above. However, having already defined position $R^1$, $R^2$ and $R^3$, and showed that the compounds obtained were STAT3 inhibitors, the person skilled in the art will also appreciate, with the present invention that in addition to the modifications suggested on $R^4$ herein, the other substitutions as suggested in WO2012/018868 would also produce a compound with STAT3 inhibiting activity. It will however be appreciated that the modifications suggested herein provide new compounds having much better inhibiting activity against STAT3.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician. Generally, the amount administered will be empirically determined, typically in the range of about 10 μg to 100 mg/kg body weight of the recipient.

The desired dose may conveniently be presented in a single dose or as divided dose administered at appropriate intervals, for example as two, three, four or more doses per day. Pharmaceutical compositions include, without limitation, those suitable for oral, (including buccal and sublingual), transdermal, or parenteral (including intramuscular, subcutaneous and intravenous) administration or in a form suitable for administration by inhalation.

The formulations may, where appropriate, be conveniently presented in discrete dosage units and may be prepared by any of the methods well known in the art of pharmacy. The methods for preparing a pharmaceutical composition can include the steps of bringing into association the compound as defined herein and pharmaceutically acceptable excipients and then, if necessary, shaping the product into the desired formulation, including applying a coating when desired.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations as defined herein may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile water or saline, before use.

Compositions suitable for topical administration in the mouth include lozenges comprising the active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For administration by inhalation, the compounds and combinations as defined herein may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present disclosure can contain more than one chiral centre. The compounds of the present invention may thus exist in the form of different diastereomers. All such diastereomers and mixtures thereof are included within the scope of the invention. The single diastereomer can be obtained by methods well known in the art, such as HPLC, crystalisation and chromatography.

The term "Solvate" means that a compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

Abbreviations used in the Description of the Preparation of the Compounds of the Present Disclosure:
Bu Butyl
$CDCl_3$ Deuterated chloroform
DCM Dichloromethane
DMAP N,N-dimethylaminopyridine
DME 1,2-dimethoxy ethane
DMEM Dulbecco's Modified Eagle Medium
DMF N,N-Dimethylformamide
DMSO Dimethyl sulfoxide
Et Ethyl
EtOAc Ethyl acetate
HMQC Heteronuclear multiple quantum coherence
mCPBA meta-chloroperbenzoic acid
HRMS High resolution mass spectrum
Me Methyl
MeOH Methanol
$NEt_3$ Triethylamine
NFSI N-fluorobenzenesulfonimide
NMR Nuclear magnetic resonance
Ph Phenyl
RT Room temperature
THF Tetrahydofuran
TBAF tetrabutylammonium fluoride
TFA trifluoroacetic acid
TMSBr trimethylsilyl bromide
RBF Round bottom flask Preparation of the Compounds of the Invention The compounds of the present disclosure can be prepared according to the procedures denoted in the following reaction Schemes 1 and 2 and Examples or modifications thereof using readily available starting materials, reagents, and conventional procedures or variations thereof well-known to a practitioner of ordinary skill in the art of synthetic organic chemistry.

Specific definitions of variables in the Schemes are given for illustrative purposes only and are not intended to limit the procedures described.

Scheme 1:

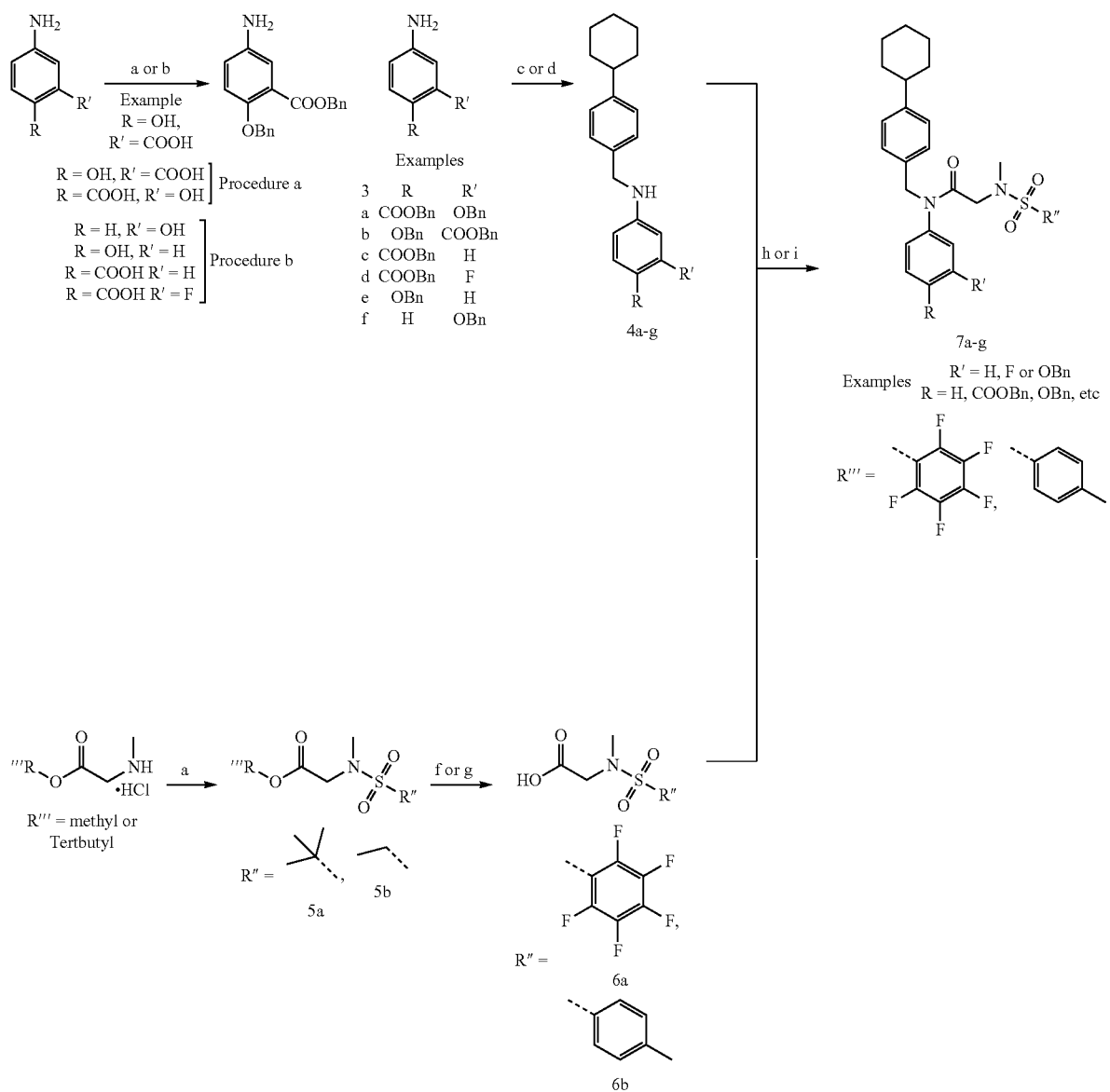

In Scheme 1; a) BnBr, KOtBu, DMF, 0° C.→R.T., 5 h; then BnBr, KOtBu, DMF, 0° C.→RT, 16 h, 61%; b) BnBr, KOtBu, DMF, 0° C.→R.T., 16 h (74%) c) Aldehyde, AcOH, 4 Å MS, MeOH, 45° C., 3 h; 2. NaCNBH$_3$, RT, 12 h, 74-91%; d) Aldehyde, AcOH, 4 Å MS, CH$_3$CH$_2$Cl$_2$, 30 min; then Na(OAc)$_3$BH, RT, 12 h, 77-98%; e) C$_5$F$_5$SO$_2$Cl or p-TsCl, DIPEA, CH$_3$CN, 0° C., RT, 1 h, 92-95%; f) DCM:TFA, 2:1, RT, 1 h, 95%; g) LiOH.H2O, THF/H2O, 3:1, RT, 1 h, 80-85% h) PPh$_3$Cl$_2$, 100° C. Microwave assisted heating, CHCl$_3$, 30 min, 60-87%; i) (COCl)$_2$, DMF$_{(cat)}$, DIPEA, CH$_2$Cl$_2$, R.T, 16 h, 71-80%. p-TsCl=para-toluenesulfonyl chloride; DIPEA=N,N-diisopropylethylamine; DMF=N,N-dimethylformamide; TFA=Trifluoroacetic acid; (COCl)$_2$=oxalyl chloride; THF=tetrahydrofuran, LiOH.H2O, lithium hydroxide hydrate.

Scheme 2:
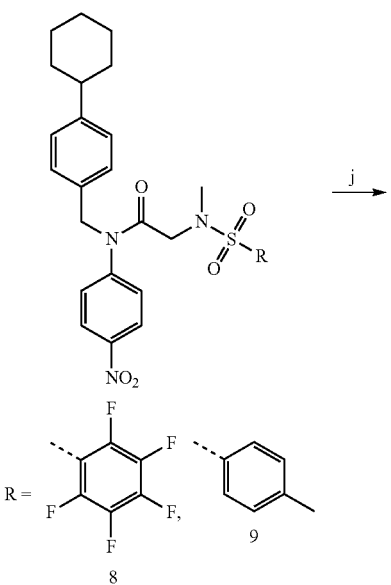
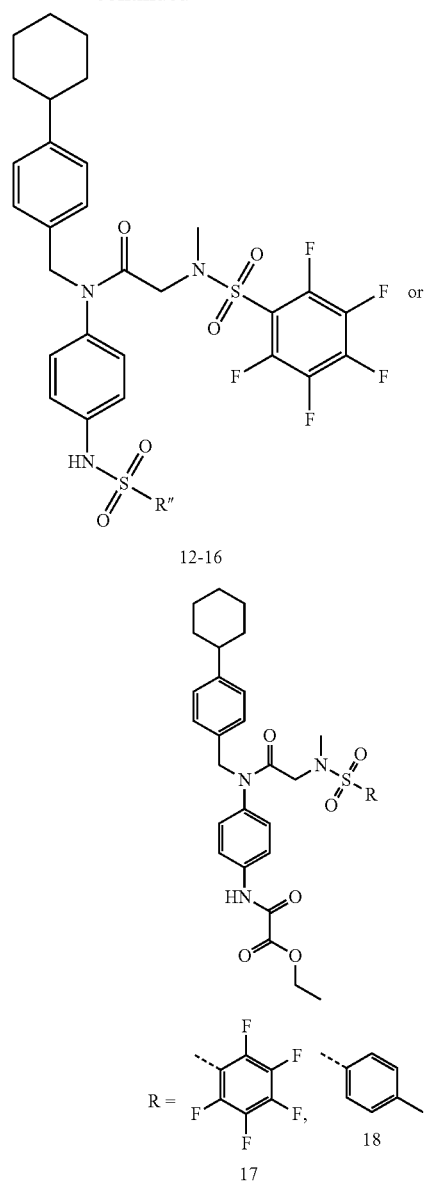
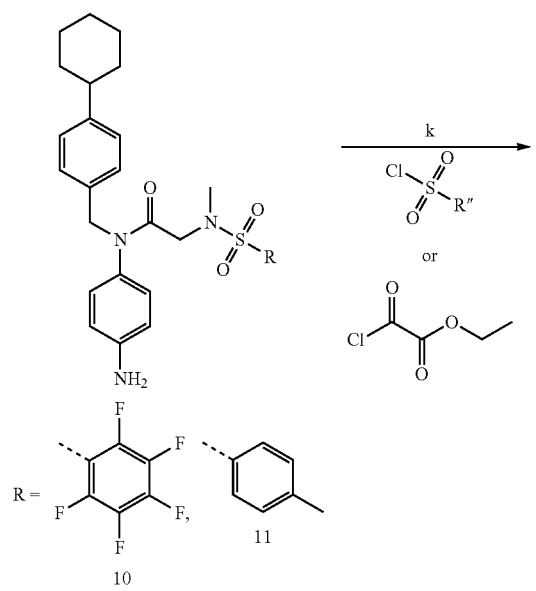
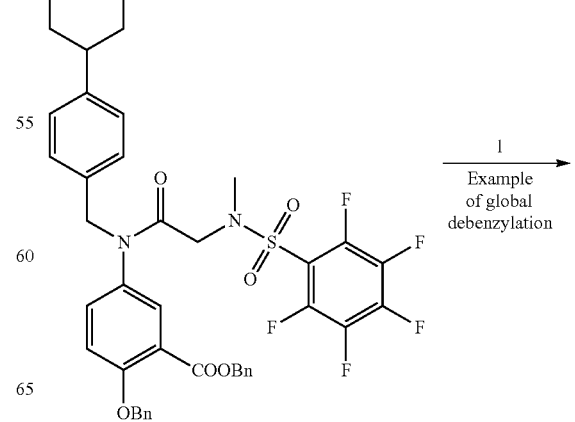

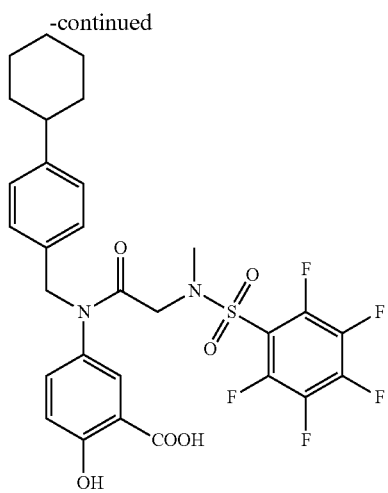

In scheme 2: j) SnCl$_2$.2H$_2$O, MeOH, reflux, 16 hr, 78%; k) "R—SO$_2$Cl, Pyridine, DCM, 0° C.→R.T., 16 h, 81% 1) H2, 10% Pd/C, MeOH/THF, 1:1, RT, 1-16 h, 85-99%. SnCl$_2$.2H$_2$O=Stannous chloride dihydrate, DCM=Dichloromethane.

Chemical Methods

Anhydrous solvents methanol, DMSO, CH$_2$Cl$_2$, THF and DMF were used directly from their Sure-Seal bottles and were purchased from Sigma Aldrich. 4 Å molecular sieves also purchased from Sigma Aldrich, were activated by heating to 300° C. under vacuum overnight. All reactions were performed in oven-dried glassware and were monitored for completeness by thin-layer chromatography (TLC) using silica gel (visualized by UV light, or developed by treatment with KMnO$_4$ stain or Hanessian's stain). A 400 MHz Bruker NMR was utilized to obtain $^1$H and $^{13}$C NMR spectra in CDCl$_3$, CD$_3$OD or d$_6$-DMSO. All NMR Chemical shifts (δ) are reported in parts per million after calibrations to residual isotopic solvent and coupling constants (J) are reported in Hz. Inhibitor purity was evaluated by a Water's reversed-phase HPLC (rpHPLC) prior to biological testing. Analysis by rpHPLC was performed using a Microsorb-MV 300 Å C18 250 mm×4.6 mm column with eluent flow set at 1 mL/min, and using gradient mixtures of (A) water with 0.1% TFA and (B) an acetonitrile solution containing 10% H$_2$O and 0.1% TFA. Ligand purity was confirmed using linear gradients from 50% A and 50% B to 100% B after an initial 2 minute period of 100% A, and a second linear gradient of 100% A to 100% B. The linear gradient consisted of a changing solvent composition of either (I) 5.2% per minute and UV detection at 254 nm or (II) 1.8% per minute and detection at 254 nm, each ending with 5 minutes of 100% B. When reporting the HPLC results, retention times for each condition are written followed by their purities in their respective order. Biologically evaluated compounds are >95% chemical purity as measured by HPLC. Traces of the HPLC results are provided in supporting information.

General Procedure a (Mono-benzylation of alcohols or acids). To a stirred solution of amino benzyl alcohols or 4-aminobenzoic acid (1.0 eq) in DMF (0.1 M) at 0° C., was added KOtBu (1.1 eq). After 15 mins, benzyl bromide (1.1 eq) was added drop-wise and the reaction left to stir over night before quenching with H$_2$O. The solution was then repeatedly extracted with ethyl acetate and the organics were combined. The organics were then washed with H$_2$O and brine then concentrated, dried over Na$_2$SO$_4$ and concentrated in vacuo. The resulting residue was purified using the Biotage Isolera automated column chromotographer in a gradient of EtOAc and Hexane and then dried under reduced pressure.

General Procedure b (Di-benzylation of the salicylic acid). To a stirred solution of 4-aminosalicyclic acid (6.00 g, 39.2 mmol) in DMF (0.1 M) at 0° C., was added KOtBu (4.84 g, 43.2 mmol). After 15 mins, benzyl bromide (5.14 mL, 43.2 mmol) was added drop-wise. The suspension was allowed to stir at R.T. for a further 4 hrs before the reaction vessel was again cooled to 0° C. A further 1.1 eqs of KtOBu (2.84 g, 43.2 mmol) were added prior to the drop-wise addition of benzyl bromide (5.14 mL, 43.2 mmol). The reaction was then stirred overnight before quenching with H$_2$O. The solution was then repeatedly extracted with ethyl acetate and the organics combined. The organics were then washed with H$_2$O and brine then concentrated, dried over Na$_2$SO$_4$ and concentrated in vacuo. The resulting residue was purified using the Biotage Isolera automated column chromotographer in a gradient of EtOAc and Hexane and then dried under reduced pressure.

General Procedure c (Reductive amination using sodium cyanoborohydride). To a solution of primary aniline (1 eq) and acetic acid (1.1 eq) stirred in anhydrous MeOH (0.1 M) with 4 Å mol. sieves was added 4-cyclohexylbenzaldehyde (1.5 eq). The solution was then heated to 45° C. for 3 hr and then allowed to cool to rt. Next, NaCNBH$_3$ (1.5 eq) was added and the reaction allowed to stir at rt overnight. When TLC indicated the reaction was complete, the reaction was concentrated in vacuo and absorbed directly onto silica for column chromatography purification using a gradient of EtOAc and Hexane.

General Procedure d (Reductive amination using sodium triacetoxy borohodyride). To a solution of primary aniline (1 eq) and acetic acid (1.1 eq) stirred in anhydrous dichloroethane (0.1 M) with 4 Å mol. sieves was added 4-cyclohexylbenzaldehyde (1.5 eq). The solution was then stirred at rt for 5 mins after which Na(OAc)$_3$BH (1.5 eq) was added and the reaction allowed to stir at rt overnight. When TLC indicated the reaction was complete, the reaction was concentrated in vacuo and absorbed directly onto silica for column chromatography purification using a gradient of EtOAc and Hexane.

General Procedure e (Sulfonylation of the secondary amine). A solution of the methyl amino (1 eq) and DIPEA (3 eq) were dissolved in anhydrous acetonitrile and cooled to 0° C. before 2,3,4,5,6-pentafluorobenzene-1-sulfonyl chloride or TsCl (1.1 eq) was added to yield the desired product. The resultant solution was allowed to stir overnight at R.T. The solvent was removed and the residue redissolved in CH$_2$Cl$_2$. The organics were then washed sequentially with 0.1 M HCl, saturated NaHCO$_3$ and brine. The organics were then dried over Na$_2$SO$_4$ and concentrated in vacuo to furnish 6a or 6b. The material was carried forward without any purification.

2-(2,3,4,5,6-pentafluoro-N-methylphenylsulfonamido) acetic acid (f). A solution of 6a was dissolved in TFA and immediately diluted with DCM to form a 1:1 TFA:DCM (0.1 M) solution. Reaction was stirred for one hour at R.T. and then co-evaporated with MeOH (3×) then CHCl$_3$ (4×) to near dryness. The residue was re-dissolved up in EtOAc and Hexanes, wet loaded onto a Biotage Isolera column, and purified using a gradient of MeOH and DCM.

General Procedure g (Ester hydrolysis using Lithium Hydroxide). Methyl or ethyl esters (1.0 eq) were dissolved in a 3:1 mixture of THF:H$_2$O. Then LiOH (1.1 eq) was added and after 30 minutes the reaction was confirmed to be complete by TLC. The reaction mixture was diluted with water, acidified (pH-5.5) by KH$_2$PO$_4$, and continuously extracted into EtOAc. Organic layers were washed with brine, dried over anhydrous Na$_2$SO$_4$ and concentrated under reduced pressure. Reaction was purified by flash column chromatography using an isocratic solvent system (35:7:1 DCM:MeOH:H$_2$O).

General Procedure h (PPh$_3$Cl$_2$ promoted peptide Amide Coupling). To a stirred solution of the acid (1.1 eq) in CHCl$_3$ (0.1 M) was added PPh$_3$Cl$_2$ (2.5 eq). After five minutes of stirring at R.T. the amine (1.0 eq) was added in one portion and the reaction was heated in the microwave at 125° C. for 15 minutes. The reaction was concentrated in vacuo and absorbed directly onto silica for column chromatography purification using a gradient of EtOAc and Hexane.

General Procedure i (Oxalyl Chloride mediated condensation). To a solution of the acid (1.0 eq) in anhydrous CH$_2$Cl$_2$ (0.1 M) at 0° C. was added oxalyl chloride (1.2 eq) followed by a drop of DMF. The reaction was stirred at 0° C. for 1 hr under an atmosphere of dry nitrogen gas before it was stopped and concentrated in vacuo. The reaction was then resumed by re-dissolving in anhydrous CH$_2$Cl$_2$ (0.1 M). After 5 mins of stirring, the amine (1.2 eq) and triethylamine (2.5 eq) was added to the reaction at 0° C. and stirred for two hours at R.T. The reaction was then quenched with H$_2$O and the aqueous layer was extracted repeatedly into ethyl acetate. The combined organic layers were then washed with brine and driver over Na$_2$SO$_4$ and the solvent was removed under reduced pressure. The crude product was purified by column chromatography on silica gel (hexanes/ethyl acetate) to afford the desired product.

Reduction of nitro to amine (j). A stirred solution of (name of the nitro) (143 mg, 0.4 mmol) and Tin (II) Chloride dihydrate (445 mg, 1.97 mmol) in DCM/MeOH (2:1) (0.1 M) was heated at 70° C. until determined to be complete by TLC. The reaction was concentrated in vacuo and diluted with water and repeatedly extracted with ethyl acetate. The collected organic layers were then combined, washed with saturated NaHCO$_3$ and dried over anhydrous Na$_2$SO$_4$, filtered and the solvent removed under reduced pressure. The material was purified using a Biotage Isolera in a gradient of 50% EtOAc:Hexanes to afford a white solid (91%).

General Procedure k (Sulfonylation of the aniline functionality). The free amine functionality was dissolved in mixture of 1:1 DCM/Pyridine (0.1 M) and cooled to 0° C. The desired sulfonyl chloride or ethyl 2-chloro-2-oxoacetate was added drop wise and the reaction stirred until deemed complete by TLC. The solvent was evaporated and the resulting residue was adsorbed onto silica gel from CH$_2$Cl$_2$ and columned using a Biotage Isolera in a gradient of EtOAc:Hexanes.

General Procedure 1 (Hydrogenolysis of benzyl ester and benzyl ether). The benzyl protected (1 eq), acid, alcohol or salicylic acid was dissolved in a stirred solution of MeOH/THF (1:2) (0.1 M). The solution was thoroughly degassed and 10% Pd/C (10 mg/mmol) was carefully added to the reaction. H$_2$ gas was bubbled through the solvent for 5 mins before the reaction was put under an atmosphere of H$_2$ gas and stirred continuously for 3 hrs. The H$_2$ gas was evacuated and the reaction filtered through celite to remove the Pd catalyst and then concentrated under reduced pressure. The resulting residue was adsorbed onto silica gel from CH$_2$Cl$_2$ and columned using a Biotage Isolera in a gradient of MeOH and DCM.

Synthesis of the benzylhydroxyl amine derivative (m)

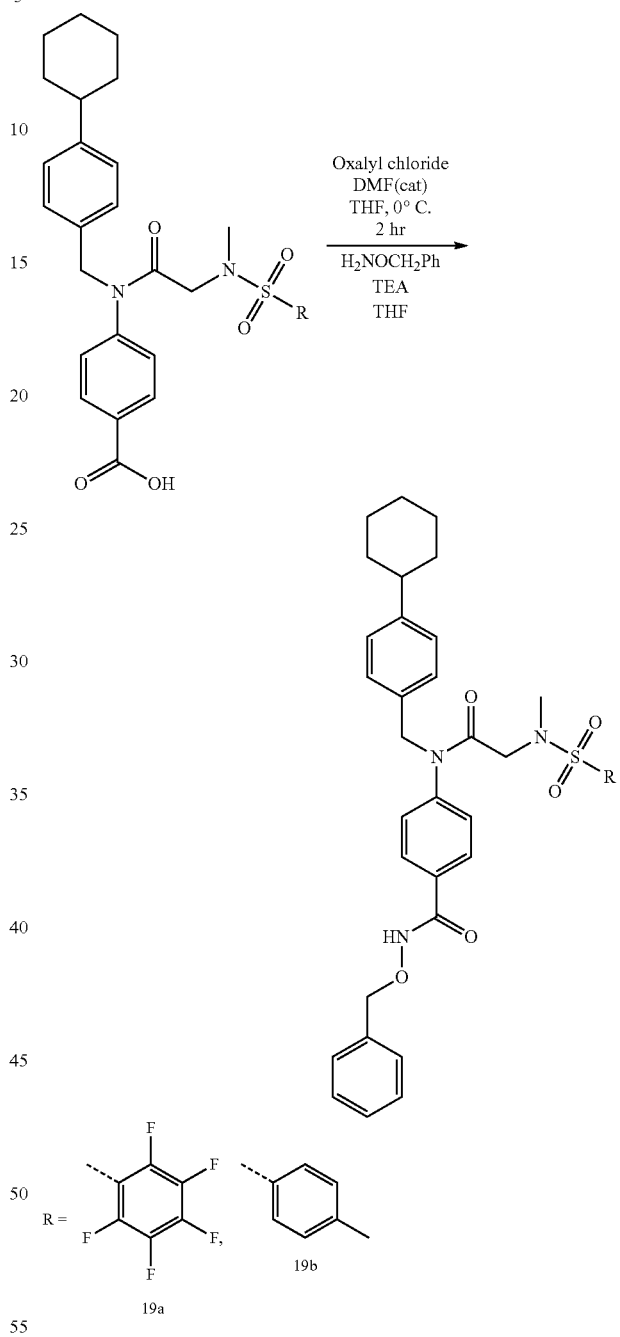

To a solution of the acid (50 mg, 0.09 mmol) in anhydrous THF (1 mL) at 0° C. was added oxalyl chloride (25.6 μM, 0.32 mmol) and a drop of DMF. The reaction was stirred at 0° C. for two hours and then concentrated under vacuo and placed under high vacuum for 15 minutes. The reaction was then resumed by re-dissolving in THF (1 mL) followed by the addition of 0-Benzylhydroxylamine (21.7 μM, 0.18 mmol) and triethylamine (52 μM, 0.37 mmol). The reaction was stirred at R.T. for 1 hr and then quenched with H$_2$O and the aqueous layer was extracted repeatedly intro ethyl acetate. The combined organic layers were then washed with brine and driver over Na₂SO₄ and the solvent was removed under reduced pressure. The crude product was purified by column chromatography on silica gel (50% hexanes/ethyl acetate) to afford the desired product (13) as a white solid (51 mg, 79%).

Synthesis of (4-(N-(4-cyclohexylbenzyl)-2-(2,3,4,5,6-pentafluoro-N methylphenylsulfonamido) acetamido)benzyl) phosphonic acid (n)

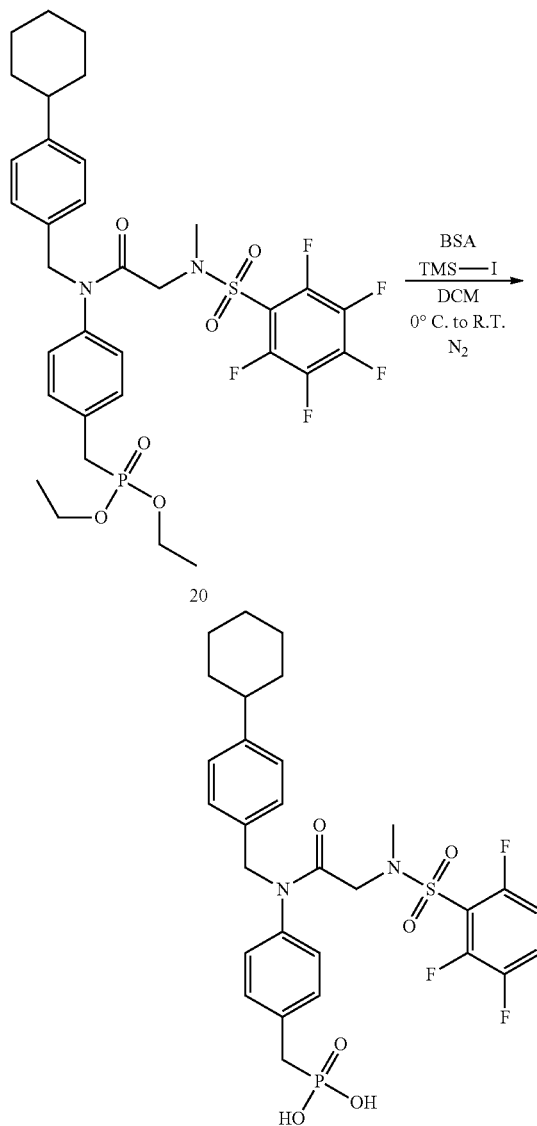

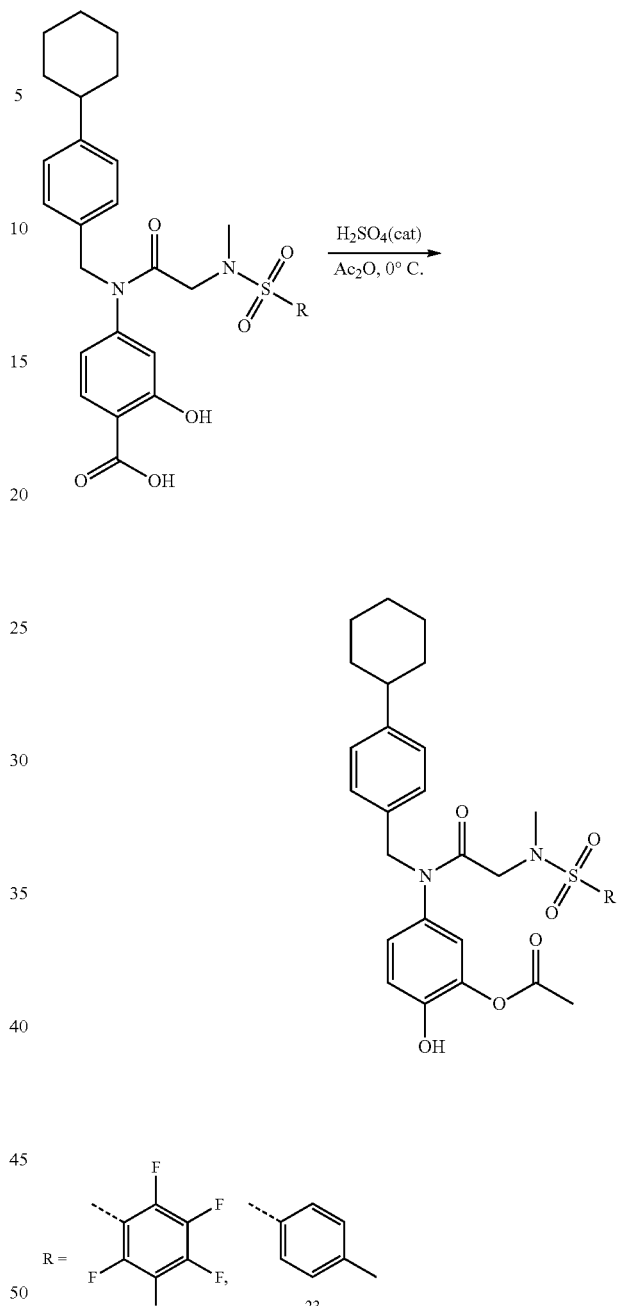

Iodotrimethylsilane (11.94 µM, 0.084 mmol) was added dropwise to a solution of phosphonate (30 mg, 0.042 mmol) and bis(timethylsilyl) trifluoroacetamide (11.25 µM, 0.046 mmol) in anhydrous DCM at 0° C. The reaction mixture was kept under nitrogen and stirred for 1 hr at 0° C. and slowly brought to room temperature and stirred for an additional 1 hr. The solution was concentrated in vacuo and purified via HPLC to yield the desired product (20 mg, 74%).

Acetylation of the salicylic acid (o).

A drop of concentrated sulphuric acid was added to a solution of the desired salicylic acid (30 mg, 0.05 mmol) in acetic anhydride (0.5 ml) at 0° C. and under an atmosphere of dry nitrogen. The reaction was stirred at R.T until complete by TLC after which the reaction was cooled to 0° C. and quenched with ice cold water. The material was concentrated in vacuo and purified by column chromatography on silica gel (5% Methanol/Dichloromethane) to afford the acetylated product (21 mg, 60%).

Synthesis of 4-(1H-tetrazol-5-yl) aniline (p)

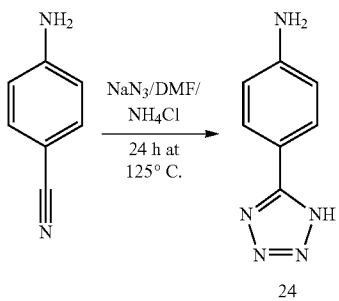 [SMILES: N#Cc1ccc(N)cc1 ; Nc1ccc(-c2nnn[nH]2)cc1]

A mixture of 4-aminobenzonitrile (100 mg, 0.85 mmol), sodium azide (110.2 mg, 1.69 mmol), DMF (8.5 mL) and ammonium chloride (45.3 mg, 0.85 mmol) was heated in an oil bath for 24 h at 125° C. When the reaction was deemed complete by TLC the mixture was acidified with 1N HCL and extracted with ethyl acetate (3×). The combined ethyl acetate was washed with brine and dried over $Na_2SO_4$, filtered and concentrated to give the crude product. The tetrazole compound was purified by column chromatography on silica gel (90% $CH_2Cl_2$/MeOH) to yield the desired product (102 mg, 74%).

Synthesis of methyl and ethyl esters (q)

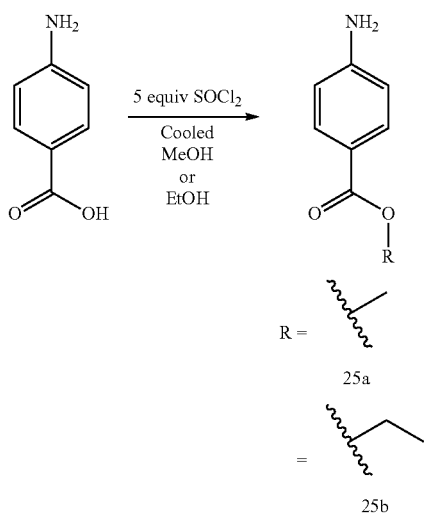

$SOCl_2$ (5 eq) was added dropwise to a cooled solution of 4-amino benzoic acid (1 eq) in alcohol (MeOH or EtOH). The reaction mixture was then stirred at R.T. for 30 minutes.

When determined to be complete by TLC the reaction was concentrated in vacuo and absorbed directly onto silica for column chromatography purification.

Synthesis of the pivoloxyl and acetoxy methyl esters (r)

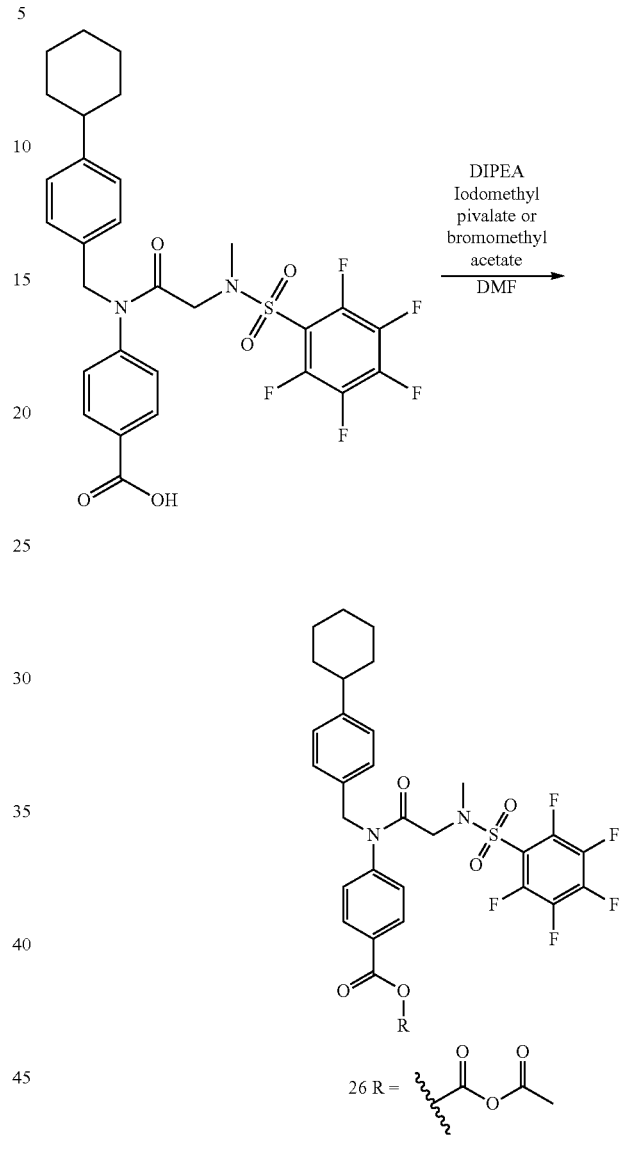

The free acid (1.0 eq) was dissolved up in anhydrous DMF. Re-distilled DIPEA (2.1 eq) was added in a single portion, followed by the addition of iodomethyl pivalate or bromomethyl acetate (2.0 eq). Reaction was covered with tin foil and allowed to react at R.T. for 24 hours. At this point, the reaction was diluted with water and repeatedly extracted into EtOAc. The combined organics were washed with water and brine, dried over anhydrous $Na_2SO_4$, filtered and concentrated under reduced pressure. The concentrated product was re-dissolved in the HPLC solution condition B. This solution was purified using preparative HPLC and immediately lyophilized from the eluent solution.

EXAMPLE 1

Compound 5a

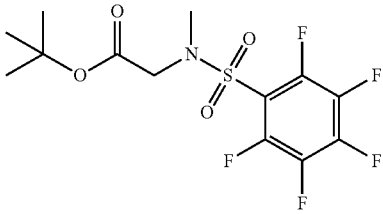 [SMILES: CN(CC(=O)OC(C)(C)C)S(=O)(=O)c1c(F)c(F)c(F)c(F)c1F]

tert-butyl 2-(2,3,4,5,6-pentafluoro-N-methylphenylsulfonamido)acetate

Chemical Formula: $C_{13}H_{14}F_5NO_4S$

Molecular Weight: 375.31

Compound 5a was synthesized according to general procedure a, yielding the final product 5a as a white solid (93%). $\delta_H$ (400 MHz, d-CDCl$_3$) 1.37 (s, 9H, CH$_3$), 3.03 (s, 3H, CH$_3$), 4.10 (s, 2H, CH$_2$); $\delta_C$ (100 MHz, d-CDCl$_3$) 27.5, 35.3, 51.5, 82.8, 115.6, 136.4, 144.8, 145.9, 167.0; LRMS (ES+) Calcd for [C$_{13}$H$_{14}$F$_5$NO$_4$S+H] 376.06 found 376.09.

EXAMPLE 2

Compound 5b

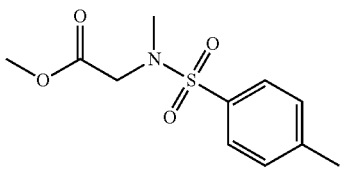

methyl 2-(N,4-dimethylphenylsulfonamido)acetate

Chemical Formula: $C_{11}H_{15}NO_4S$

Molecular Weight: 257.31

Compound 5b was synthesized according to general procedure a, yielding the final product 5b as a white solid (91%). $\delta_H$ (400 MHz, d-CDCl$_3$) 2.42 (s, 3H, CH$_3$), 2.87 (s, 3H, CH$_3$), 3.65 (s, 3H, CH$_3$), 3.96 (s, 2H, CH$_2$), 7.30 (d, J=8.0 Hz, 2H, CH), 7.68 (d, J=8.2 Hz, 2H, CH); $\delta_C$ (100 MHz, d-CDCl$_3$) 21.1, 35.2, 50.3, 52.0, 126.9, 134.6, 143.0, 168.3; LRMS (ES+) Calcd for [C$_{11}$H$_{15}$NO$_4$S+H] 258.08 found 258.29.

EXAMPLE 3

Compound 6a

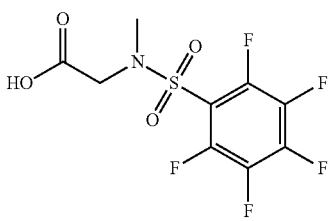 [SMILES: CN(CC(=O)O)S(=O)(=O)c1c(F)c(F)c(F)c(F)c1F]

2-(2,3,4,5,6-pentafluoro-N-methylphenylsulfonamido)acetic acid

Chemical Formula: $C_9H_6F_5NO_4S$

Molecular Weight: 319.21

Compound 6a was synthesized according to general procedure a, yielding the final product 6a as a brown solid (95%). ($\delta_H$ (400 MHz, d-CDCl$_3$) 2.86 (s, 3H, CH$_3$), 4.10 (s, 2H, CH$_2$); $\delta_C$ (100 MHz, d-CDCl$_3$) 35.4, 51.8, 115.3, 136.4, 144.8, 145.9, 167.1; LRMS (ES+) Calcd for [C$_9$H$_6$F$_5$NO$_4$S+H] 320.00 found 319.97.

EXAMPLE 4

Compound 6b

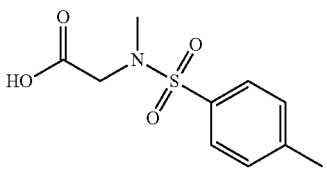 [SMILES: Cc1ccc(S(=O)(=O)N(C)CC(=O)O)cc1]

2-(N,4-dimethylphenylsulfonamido)acetic acid

Chemical Formula: $C_{10}H_{13}NO_4S$

Molecular Weight: 243.28

Compound 6b was synthesized according to general procedure g, yielding the final product 6b as a white solid (84%). $\delta_H$ (400 MHz, d-CDCl$_3$) 2.32 (s, 3H, CH$_3$), 2.76 (s, 3H, CH$_3$), 3.86 (s, 2H, CH$_2$), 7.21 (d, J=8.0 Hz, 2H, CH), 7.68 (d, J=8.2 Hz, 2H, CH); $\delta_C$ (100 MHz, d-CDCl$_3$) 20.8, 35.1, 50.0, 126.7, 129.0, 134.2, 143.1, 172.9; LRMS (ES+) Calcd for [C$_{10}$H$_{13}$NO$_4$S+H] 244.06 found 244.28.

EXAMPLE 5

Compound 3a

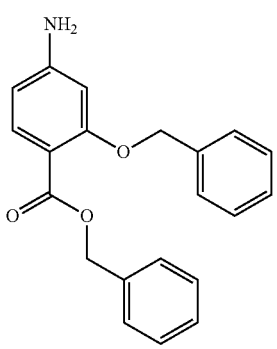 [SMILES: Nc1ccc(C(=O)OCc2ccccc2)c(OCc2ccccc2)c1]

benzyl 4-amino-2-(benzyloxy)benzoate

Chemical Formula: $C_{21}H_{19}NO_3$

Molecular Weight: 333.3805

Compound 3a was synthesized according to general procedure a, yielding the final product 3a as an orange solid (71%). $\delta_H$ (400 MHz, d-CDCl$_3$) 4.13 (brs, 2H, NH$_2$), 5.05 (s, 2H, CH$_2$), 5.35 (s, 2H, CH$_2$), 6.19-6.23 (m, 2H, CH), 7.31-7.49 (m, 10H, CH), 7.81-7.86 (m, 1H, CH); $\delta_C$ (100 MHz, d-CDCl$_3$) 65.8, 70.3, 99.1, 106.7, 108.8, 126.9, 127.6, 127.8, 128.0, 128.4, 134.4, 136.6, 136.7, 152.5, 160.8, 165.8; LRMS (ES+) Calcd for [$C_{21}H_{19}NO_3$+Na] 356.13 found 356.33.

EXAMPLE 6

Compound 3b

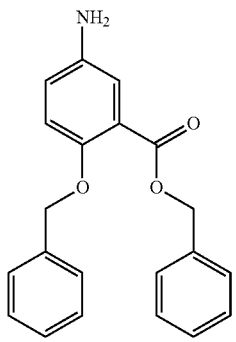 [SMILES: Nc1ccc(OCc2ccccc2)c(C(=O)OCc2ccccc2)c1]

benzyl 5-amino-2-(benzyloxy)benzoate

Chemical Formula: $C_{21}H_{19}NO_3$

Molecular Weight: 333.38

Compound 3b was synthesized according to general procedure a, yielding the final product 3b as a yellow solid (75%). $\delta_H$ (400 MHz, d-(CDCl$_3$) 4.21 (brs, 2H, NH$_2$), 5.10 (s, 2H, CH$_2$), 5.33 (s, 2H, CH$_2$), 7.35-7.48 (m, 10H, CH); $\delta_C$ (100 MHz, d-CDCl$_3$) 67.1, 70.8, 100.1, 105.4, 110.2, 126.4, 127.3, 127.9, 128.2, 128.1, 134.8, 136.3, 136.5, 152.5, 160.2, 165.7; LRMS (ES+) Calcd for [$C_{21}H_{19}NO_3$+Na] 356.13 found 356.14.

EXAMPLE 7

Compound 3c

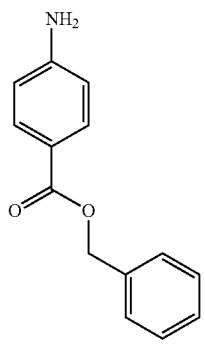 [SMILES: Nc1ccc(C(=O)OCc2ccccc2)cc1]

benzyl 4-aminobenzoate

Chemical Formula: $C_{14}H_{13}NO_2$

Molecular Weight: 227.26

Compound 3c was synthesized according to general procedure b, yielding the final product 3c as a white solid (82%). $\delta_H$ (400 MHz, d-CDCl$_3$) 4.25 (brs, 2H, NH$_2$), 5.38 (s, 2H, CH), 6.63 (d, J=8.2 Hz, 2H, CH), 7.33-7.51 (m, 5H, CH), 7.96 (d, J=8.2 Hz, 2H, CH); $\delta_C$ (100 MHz, d-CDCl$_3$) 66.1, 113.7, 118.9, 127.9, 128.0, 128.7, 131.7, 136.6, 151.5, 166.6; LRMS (ES+) Calcd for [$C_{14}H_{13}NO_2$+Na] 250.08 found 250.07.

EXAMPLE 8

Compound 3d

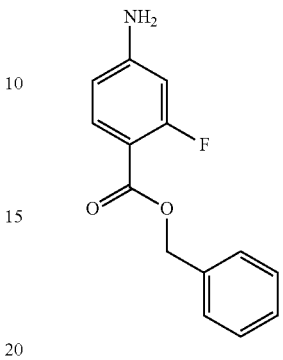

benzyl 4-amino-2-fluorobenzoate

Chemical Formula: $C_{14}H_{12}FNO_2$

Molecular Weight: 245.25

Compound 3d was synthesized according to general procedure b, yielding the final product 3d as a white solid (98%). $\delta_H$ (400 MHz, d-CDCl$_3$) 4.15 (brs, 2H, NH$_2$), 5.34 (s, 2H, CH), 6.31-6.36 (m, 1H, CH), 6.38-6.43 (m, 1H, CH), 7.28-7.45 (m, 5H, CH), 7.76-7.82 (m, 1H, CH); $\delta_C$ (100 MHz, d-CDCl$_3$) 66.1, 113.7, 118.9, 127.9, 128.0, 128.7, 131.7, 136.6, 151.5, 166.6; LRMS (ES+) Calcd for [$C_{14}H_{12}FNO_2$+Na] 268.07 found 268.06.

EXAMPLE 9

Compound 3e

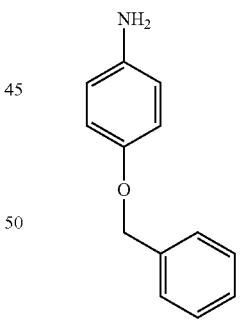

4-(benzyloxy)aniline

Chemical Formula: $C_{13}H_{13}NO$

Molecular Weight: 199.25

Compound 3e was synthesized according to general procedure b, yielding the final product 3e as a grey solid (84%). $\delta_H$ (400 MHz, d-CDCl$_3$) 3.66 (brs, 2H, NH$_2$), 5.03 (s, 2H, CH$_2$), 6.29-6.35 (m, 2H, CH), 6.38-6.44 (m, 2H, CH), 7.03-7.1 (m, 1H, CH), 7.29-7.45 (m, 5H, CH); $\delta_C$ (100 MHz, d-CDCl$_3$) 68.1, 114.2, 116.6, 125.0, 127.5, 127.5, 127.9, 128.1, 136.9; LRMS (ES+) Calcd for [$C_{13}H_{13}NO$+H] 199.19 found 199.23.

EXAMPLE 10

Compound 3f

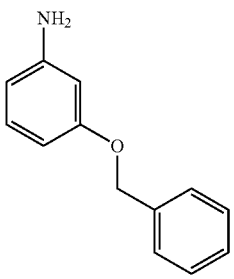 [SMILES: Nc1cccc(OCc2ccccc2)c1]

3-(benzyloxy)aniline
Chemical Formula: $C_{13}H_{13}NO$
Molecular Weight: 199.2484

Compound 3f was synthesized according to general procedure b, yielding the final product 3f as a white solid. $\delta_H$ (400 MHz, d-CDCl$_3$) 3.66 (brs, 2H, NH$_2$), 5.03 (s, 2H, CH$_2$), 6.29-6.34 (m, 2H, CH), 6.38-6.43 (m, 1H, CH) 7.03-7.1 (m, 1H, CH), 7.31-7.45 (m, 5H, CH); $\delta_C$ (100 MHz, d-CDCl$_3$) 70.9, 102.7, 105.6, 107.3, 126.5, 127.5, 127.7, 128.1, 130.1, 151.2, 160.4; LRMS (ES+) Calcd for [$C_{13}H_{13}NO+H$] 199.19 found 199.23.

EXAMPLE 11

Compound 4a

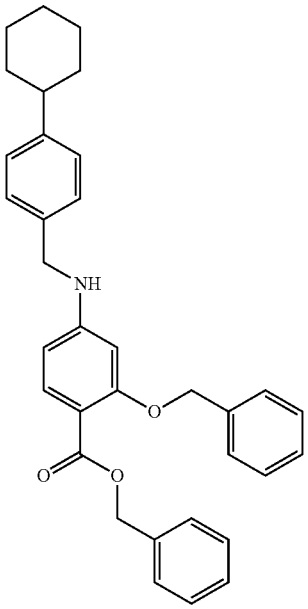 [SMILES: O=C(OCc1ccccc1)c1ccc(NCc2ccc(C3CCCCC3)cc2)cc1OCc1ccccc1]

benzyl 2-(benzyloxy)-4-((4-cyclohexylbenzyl)amino)benzoate
Chemical Formula: $C_{34}H_{35}NO_3$
Molecular Weight: 505.65

Compound 4a was synthesized according to general procedure c, yielding the final product 4a as an orange solid (81%). $\delta_H$ (400 MHz, d-(CDCl$_3$) 1.25-1.48 (m, 5H, CH$_2$), 1.73-1.94 (m, 5H, CH$_2$), 2.48-2.52 (m, 1H, CH), 4.30 (s, 2H, CH$_2$), 5.05 (s, 2H, CH$_2$), 5.35 (s, 2H, CH$_2$), 6.68-6.75 (m, 1H, CH), 6.19-6.23 (m, 2H, CH), 6.86-6.92 (m, 1H, CH), 7.16-7.22 (m, 2H, CH), 7.30-7.48 (m, 10H, CH), 7.37-7.4 (m, 2H, CH); $\delta_C$ (100 MHz, d-CDCl$_3$) 26.1, 26.6, 34.3, 44.1, 47.1, 65.5, 70.2, 97.3, 104.9, 108.1, 125.9, 126.8, 127.2, 127.4, 127.5, 127.8, 128.1, 128.3, 133.9, 134.8, 135.2, 136.6, 136.8, 147.3, 152.8, 160.6, 165.7; LRMS (ES+) Calcd for [$C_{34}H_{35}NO_3+Na$] 528.65 found 528.35.

EXAMPLE 12

Compound 4b benzyl 2-(benzyloxy)-5-((4-cyclohexylbenzyl)amino)benzoate
Chemical Formula: $C_{34}H_{35}NO_3$
Molecular Weight: 505.65

Compound 4b was synthesized according to general procedure c, yielding the final product 4b as an orange solid (86%). $\delta_H$ (400 MHz, d-(CDCl$_3$) 1.29-1.49 (m, 5H, CH$_2$), 1.72-1.95 (m, 5H, CH$_2$), 2.44-2.56 (m, 1H, CH), 4.25 (s, 2H, CH$_2$), 5.05 (s, 2H, CH$_2$), 5.4 (s, 2H, CH$_2$), 6.68-6.75 (m, 1H, CH), 6.86-6.92 (m, 1H, CH), 7.16-7.22 (m, 3H, CH), 7.25-7.36 (m, 10H, CH), 7.37-7.4 (m, 2H, CH); $\delta_C$ (100 MHz, d-CDCl$_3$) 26.1, 26.8, 34.4, 44.2, 48.6, 66.6, 72.2, 115.6, 116.8, 117.6, 121.7, 126.9, 127.2, 127.5, 127.9, 128.1, 128.3, 128.6, 136.1, 136.3, 137.2, 142.4, 147.2, 150.5, 166.6; LRMS (ES+) Calcd for [$C_{34}H_{35}NO_3+Na$] 528.65 found 528.35.

EXAMPLE 13

Compound 4c

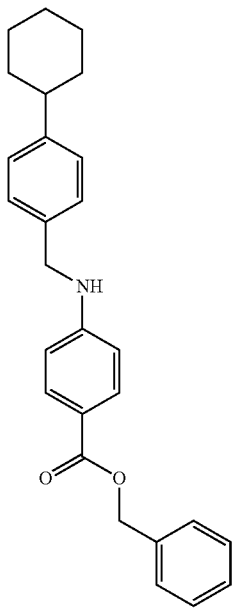 [SMILES: O=C(OCc1ccccc1)c1ccc(NCc2ccc(C3CCCCC3)cc2)cc1]

benzyl 4-((4-cyclohexylbenzyl)amino)benzoate
Chemical Formula: $C_{27}H_{29}NO_2$
Molecular Weight: 399.52

Compound 4c was synthesized according to general procedure d, yielding the final product 4c as a white solid (88%). $\delta_H$ (400 MHz, d-CDCl$_3$) 1.28-1.48 (m, 5H, CH$_2$), 1.71-1.93 (m, 5H, CH$_2$), 2.42-2.55 (m, 1H, CH), 4.35 (s, 2H, CH$_2$), 5.36 (s, 2H, CH$_2$), 6.87 (d, J=8.0 Hz, 2H, CH), 7.10-7.16 (m, 4H, CH), 7.33-7.47 (m, 5H, CH), 8.10 (d, J=8.0 Hz, 2H, CH); $\delta_C$ (100 MHz, d-CDCl$_3$) 26.2, 26.5, 34.1, 44.1, 46.8, 66.9, 126.9, 128.2, 128.2, 128.4, 128.5, 128.4, 131.3, 133.4, 135.1, 147.8, 165.1, 165.7; LRMS (ES+) Calcd for [C$_{27}$H$_{29}$NO$_2$+H] 399.22 found 399.16.

EXAMPLE 14

Compound 4d

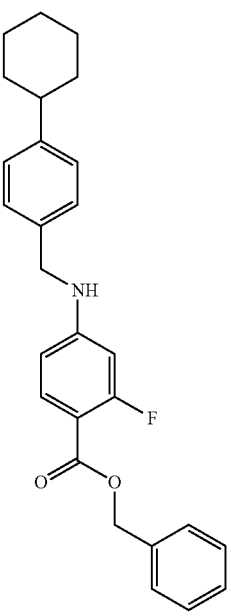 [SMILES: O=C(OCc1ccccc1)c1ccc(NCc2ccc(C3CCCCC3)cc2)cc1F]

benzyl 4-((4-cyclohexylbenzyl)amino)-2-fluorobenzoate
Chemical Formula: $C_{27}H_{28}FNO_2$
Molecular Weight: 417.52

Compound 4d was synthesized according to general procedure d, yielding the final product 4d as a white solid (98%). $\delta_H$ (400 MHz, d-CDCl$_3$) 1.26-1.49 (m, 5H, CH$_2$), 1.72-1.95 (m, 5H, CH$_2$), 2.48-2.56 (m, 1H, CH), 4.31 (s, 2H, CH$_2$), 4.72 (brs, 1H, NH), 5.34 (s, 2H, CH$_2$), 6.27-6.32 (m, 1H, CH), 6.36-6.41 (m, 1H, CH), 7.22 (d, J=8.1 Hz, 2H, CH), 7.27 (d, J=8.1 Hz, 2H, CH), 7.32-7.49 (m, 5H, CH), 7.78-7.84 (m, 1H, CH); $\delta_C$ (100 MHz, d-CDCl$_3$) 25.9, 26.8, 34.3, 44.1, 47.3, 65.9, 106.2, 108.3, 127.2, 127.4, 127.8, 128.4, 133.4, 134.9, 136.4, 147.6, 153.5, 153.6, 162.9, 164.3, 165.6; LRMS (ES+) Calcd for [C$_{27}$H$_{28}$FNO$_2$+H] 418.21 found 419.38.

EXAMPLE 15

Compound 4e

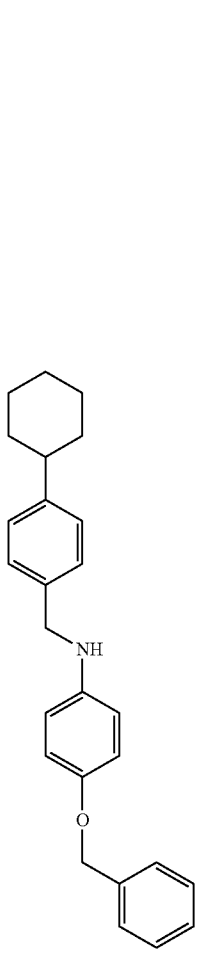 [SMILES: c1ccc(COc2ccc(NCc3ccc(C4CCCCC4)cc3)cc2)cc1]

4-(benzyloxy)-N-(4-cyclohexylbenzyl)aniline
Chemical Formula: $C_{26}H_{29}NO$
Molecular Weight: 371.51

Compound 4e was synthesized according to general procedure c, yielding the final product 4e as a yellow solid (86%). $\delta_H$ (400 MHz, d-CDCl$_3$) 1.32-1.50 (m, 5H, CH$_2$), 1.29-1.48 (m, 5H, CH$_2$), 2.43-2.56 (m, 1H, CH), 4.25 (s, 2H, CH$_2$), 5.01 (s, 2H, CH$_2$), 6.58-6.65 (m, 2H, CH), 6.84-6.90 (m, 2H, CH), 7.20 (d, J=7.9 Hz, 2H, CH), 7.31 (d, J=8.2 Hz, 2H, CH), 7.33-7.46 (m, 5H, CH); $\delta_C$ (100 MHz, d-CDCl$_3$) 26.2, 26.9, 34.5, 44.3, 49.0, 70.9, 113.9, 116.2, 127.0, 127.5, 127.6, 127.7, 128.5, 136.9, 137.7, 142.9, 147.1, 151.4; LRMS (ES+) Calcd for [$C_{26}H_{29}NO+H$] 371.23 found 372.25.

EXAMPLE 16

Compound 4f

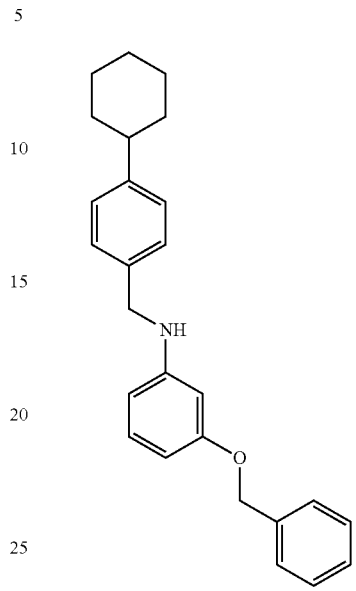

3-(benzyloxy)-N-(4-cyclohexylbenzyl)aniline
Chemical Formula: $C_{26}H_{29}NO$
Molecular Weight: 371.51

Compound 4f was synthesized according to general procedure d, yielding the final product 4f as a yellow solid (76%). $\delta_H$ (400 MHz, d-CDCl$_3$) 1.22-1.42 (m, 5H, CH$_2$), 1.71-1.91 (m, 5H, CH$_2$), 2.43-2.54 (m, 1H, CH), 4.26 (s, 2H, CH$_2$), 5.01 (s, 2H, CH$_2$), 6.27-6.33 (m, 2H, CH), 6.35-6.40 (m, 1H, CH) 7.06-7.13 (m, 1H, CH), 7.19 (d, J=8.1 Hz, 2H, CH), 7.28 (d, J=8.1 Hz, 2H, CH), 7.31-7.45 (m, 5H, CH); $\delta_C$ (100 MHz, d-CDCl$_3$)) 26.2, 26.5, 34.1, 44.1, 49.5, 70.1, 103.1, 106.8, 106.9, 114.1, 116.4, 127.3, 127.5, 127.6, 127.7, 128.5, 136.9, 137.7, 147.1; LRMS (ES+) Calcd for [$C_{26}H_{29}NO+H$] 371.23 found 372.28.

EXAMPLE 17

Compound 4g

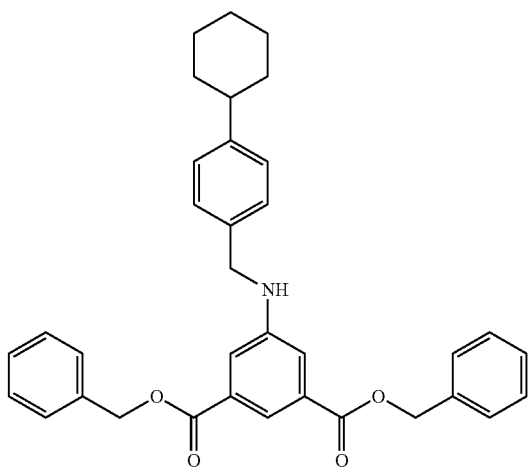 [SMILES: O=C(OCc1ccccc1)c1cc(NCc2ccc(C3CCCCC3)cc2)cc(C(=O)OCc2ccccc2)c1]

dibenzyl 5-((4-cyclohexylbenzyl)amino)isophthalate
Chemical Formula: $C_{35}H_{35}NO_4$
Molecular Weight: 533.6567

Compound 4g was synthesized according to general procedure d, yielding the final product 4g as a white solid (88%). $\delta_H$ (400 MHz, d-(CDCl$_3$)) 1.31-1.42 (m, 5H, CH$_2$), 1.74-1.89 (m, 5H, CH$_2$), 2.41-2.50 (m, 1H, CH), 4.94 (s, 2H, CH$_2$), 5.31 (s, 4H, CH$_2$), 7.01-7.14 (m, 4H, CH), 7.37-7.52 (m, 10H, CH), 7.81-7.86 (m, 2H, CH), 8.42 (s, 1H, CH)); $\delta_C$ (100 MHz, d-CDCl$_3$) 26.1, 26.5, 34.1, 35.1, 49.1, 67.2, 68.1, 116.1, 118.5, 119.1, 126.1, 126.3, 127.1, 127.5, 127.9, 138.4, 138.7, 141.2, 144.3, 147.5, 161.4, 166.1; LRMS (ES+) Calcd for [$C_{35}H_{35}NO_4$+H] 534.32 found 534.17.

EXAMPLE 18

Compound 4h

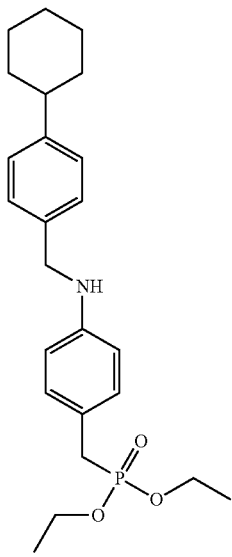 [SMILES: CCOP(=O)(Cc1ccc(NCc2ccc(C3CCCCC3)cc2)cc1)OCC]

diethyl 4-((4-cyclohexylbenzyl)amino)benzylphosphonate
Chemical Formula: $C_{24}H_{34}NO_3P$
Molecular Weight: 415.5054

Compound 4h was synthesized according to general procedure c, yielding the final product 4h as a yellow oil (78%). $\delta_H$ (400 MHz, d-(CDCl$_3$)) 1.24 (t, J=7.1 Hz, 6H, CH$_3$), 1.34-1.45 (m, 5H, CH$_2$), 1.70-1.89 (m, 5H, CH$_2$), 2.43-2.54 (m, 1H, CH), 3.01 (s, 3H, CH$_3$), 3.10 (s, 1H, CH), 3.16 (s, 1H, CH), 3.93-4.04 (m, 4H, CH$_2$), 4.25 (m, 2H, CH$_2$), 6.58 (d, J=8.2 Hz, 2H, CH), 7.10 (d, J=7.9 Hz, 2H, CH), 7.17 (d, J=8.0 Hz, 2H, CH), 7.27 (d, J=8.0 Hz, 2H, CH); $\delta_C$ (100 MHz, d-CDCl$_3$) 16.2, 16.3, 26.0, 26.8, 44.2, 48.0, 61.8, 61.9, 112.9, 113.0, 126.9, 127.5, 130.4, 130.5, 136.5, 147.0; HRMS (ES+) Calcd for [$C_{24}H_{34}NO_3P$+H] 416.24 found 416.32.

EXAMPLE 19

Compound 4i

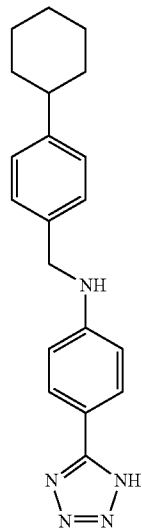 [SMILES: c1cc(C2CCCCC2)ccc1CNc1ccc(-c2nnn[nH]2)cc1]

N-(4-cyclohexylbenzyl)-4-(1H-tetrazol-5-yl)aniline
Chemical Formula: $C_{20}H_{23}N_5$
Molecular Weight: 333.43

Compound 4i was synthesized according to procedure d, yielding the final product 4i as white solid (89%). $\delta_H$ (400 MHz, d-MeOD$_3$) 1.23-1.45 (m, 5H, CH$_2$), 1.71-1.91 (m, 5H, CH$_2$), 2.45-2.55 (m, 1H, CH), 4.31 (d, J=5.3 Hz, 2H, CH$_2$), 4.71 (brs, 1H, NH), 6.55 (d, J=8.8 Hz, 2H, CH), 7.20-7.28 (m, 4H, CH), 8.10 (d, J=8.8 Hz, 2H, CH); $\delta_C$ (100 MHz, d-C$_2$D$_6$CO) 113.1, 121.5, 126.6, 143.2, 154.3; LRMS (ES+) Calcd for [$C_{20}H_{23}N_5$+H] 334.20 found 334.31.

EXAMPLE 20

Compound 4j

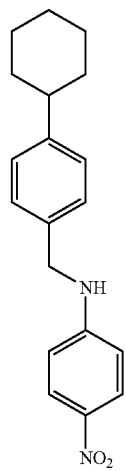 [SMILES: O=[N+]([O-])c1ccc(NCc2ccc(C3CCCCC3)cc2)cc1]

N-(4-cyclohexylbenzyl)-4-nitroaniline
Chemical Formula: $C_{19}H_{22}N_2O_2$

Molecular Weight: 310.39

Compound 4j was synthesized according to general procedure c, yielding the final product 4j as a yellow solid (85%). $\delta_H$ (400 MHz, d-CDCl$_3$) 1.21-1.47 (m, 5H, CH$_2$), 1.72-1.92 (m, 5H, CH$_2$), 2.45-2.57 (m, 1H, CH), 4.28 (d, J=5.3 Hz, 2H, CH$_2$), 4.78 (brs, 1H, NH), 6.57 (d, J=8.9 Hz, 2H, CH), 7.19-7.29 (m, 4H, CH), 8.10 (d, J=8.9 Hz, 2H, CH); $\delta_C$ (100 MHz, d-CDCl$_3$) 25.2, 26.1, 34.1, 43.2, 48.7, 113.5, 126.2, 127.5, 128.5, 136.9, 137.7, 145.1, 154.4; LRMS (ES+) Calcd for [C$_{19}$H$_{22}$F$_5$N$_2$O$_2$+H] 311.16 found 311.21.

EXAMPLE 21

Compound 4k

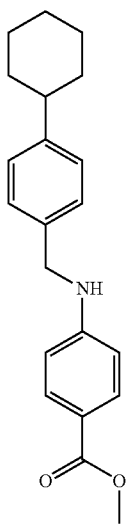

methyl 4-((4-cyclohexylbenzyl)amino)benzoate
Chemical Formula: C$_{21}$H$_{25}$NO$_2$
Molecular Weight: 323.43

Compound 4k was synthesized according to general procedure c, yielding the final product 4k as a brown solid (81%). $\delta_H$ (400 MHz, d-CDCl$_3$) 1.26-1.47 (m, 5H, CH$_2$), 1.64-1.91 (m, 5H, CH$_2$), 2.37-2.54 (m, 1H, CH), 3.91 (s, 3H, CH$_3$), 4.32 (s, 2H, CH$_2$), 6.79 (d, J=7.4 Hz, 2H, CH), 7.01-7.14 (m, 4H, CH), 7.89 (d, J=8.0 Hz, 2H, CH); $\delta_C$ (100 MHz, d-CDCl$_3$) 25.2, 26.1, 34.3, 43.6, 48.1, 51.8, 112.3, 122.1, 126.4, 128.1, 131.2, 137.3, 147.6, 152.4, 165.8; LRMS (ES+) Calcd for [C$_{21}$H$_{25}$NO$_2$+Na] 346.18 found 345.88.

EXAMPLE 22

Compound 4l

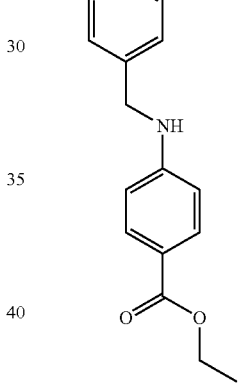

ethyl 4-((4-cyclohexylbenzyl)amino)benzoate
Chemical Formula: C$_{22}$H$_{27}$NO$_2$
Molecular Weight: 337.46

Compound 4l was synthesized according to general procedure c, yielding the final product 4l as a white solid (81%). $\delta_H$ (400 MHz, d-CDCl$_3$) 1.24-1.46 (m, 8H, CH$_2$), 1.64-1.91 (m, 5H, CH$_2$), 2.38-2.54 (m, 1H, CH), 4.31 (q, J=7.1 Hz, 2H, CH$_2$), 4.32 (s, 2H, CH$_2$), 6.64 (d, J=7.9 Hz, 2H, CH), 7.01-7.14 (m, 4H, CH), 7.86 (d, J=8.1 Hz, 2H, CH); $\delta_C$ (100 MHz, d-CDCl$_3$) 14.3, 25.4, 26.1, 34.5, 44.1, 48.1, 60.3, 112.3, 122.1, 126.4, 128.1, 131.8, 136.9, 147.6, 151.4, 166.8; LRMS (ES+) Calcd for [C$_{22}$H$_{27}$NO$_2$+Na] 360.19 found 359.89.

EXAMPLE 23

Compound 7a

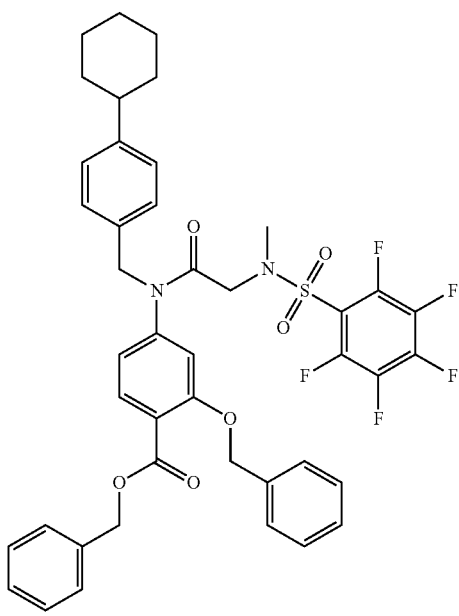 [SMILES: CN(CC(=O)N(Cc1ccc(C2CCCCC2)cc1)c1ccc(C(=O)OCc2ccccc2)c(OCc2ccccc2)c1)S(=O)(=O)c1c(F)c(F)c(F)c(F)c1F]

benzyl 2-(benzyloxy)-4-(N-(4-cyclohexylbenzyl)-2-(2,3,4,5,6-pentafluoro-N-methylphenylsulfonamido)acetamido)benzoate
Chemical Formula: $C_{43}H_{39}F_5N_2O_6S$
Molecular Weight: 806.84

Compound 7a was synthesized according to general procedure d, yielding the final product 7a as a yellow oil (81%). $\delta_H$ (400 MHz, d-CDCl$_3$) 1.33-1.41 (m, 5H, CH$_2$), 1.70-1.85 (m, 5H, CH$_2$), 2.42-2.51 (m, 1H, CH), 3.10 (s, 3H, CH$_3$), 3.84 (s, 2H, CH$_2$), 4.47 (s, 2H, CH$_2$), 4.76 (s, 2H, CH$_2$), 5.38 (s, 2H, CH$_2$), 6.43 (s, 1H, CH), 6.68 (d, J=8.0 Hz, 1H, CH), 6.95 (d, J=7.0 Hz, 2H, CH), 7.10 (d, J=7.2 Hz, 2H, CH), 7.30-7.41 (m, 10H, CH), 7.85 (dd, J=8.0 and 1.2 Hz, 1H, CH); $\delta_C$ (100 MHz, d-CDCl$_3$) 26.1, 26.7, 34.3, 35.3, 44.2, 51.9, 52.7, 67.1, 70.7, 112.0, 114.1, 115.9, 119.8, 121.0, 127.1, 127.2, 128.1, 128.3, 128.5, 128.6, 128.7, 133.3, 133.4, 135.6, 135.7, 137.8, 141.6, 142.9, 144.2, 147.9, 158.7, 165.2, 165.8; LRMS (ES+) Calcd for [C$_{43}$H$_{39}$F$_5$N$_2$O$_6$S+H] 807.84 found 807.79.

EXAMPLE 24

Compound 7b

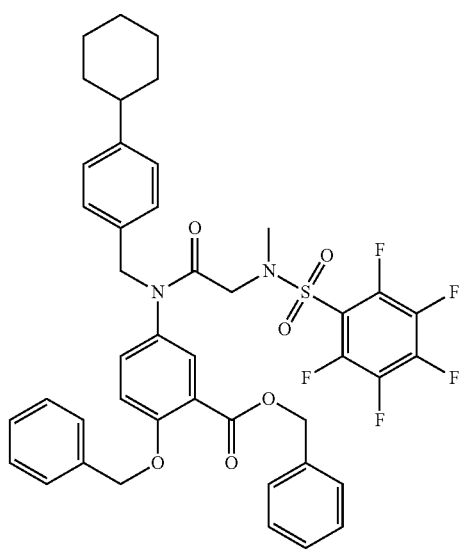 [SMILES: CN(CC(=O)N(Cc1ccc(C2CCCCC2)cc1)c1ccc(OCc2ccccc2)c(C(=O)OCc2ccccc2)c1)S(=O)(=O)c1c(F)c(F)c(F)c(F)c1F]

benzyl 2-(benzyloxy)-5-(N-(4-cyclohexylbenzyl)-2-(2,3,4,5,6-pentafluoro-N-methylphenylsulfonamido)acetamido)benzoate
Chemical Formula: $C_{43}H_{39}F_5N_2O_6S$
Molecular Weight: 806.84

Compound 7b was synthesized according to general procedure h, yielding the final product 7b as an orange solid (68%). $\delta_H$ (400 MHz, d-(CDCl$_3$) 1.33-1.43 (m, 5H, CH$_2$), 1.72-1.89 (m, 5H, CH$_2$), 2.42-2.52 (m, 1H, CH), 3.10 (s, 3H, CH$_3$), 3.94 (s, 2H, CH$_2$), 4.67 (s, 2H, CH$_2$), 5.15 (s, 2H, CH$_2$), 5.33 (s, 2H, CH$_2$), 6.93-6.99 (m, 4H, CH), 7.06-7.12 (m, 2H, CH), 7.31-7.45 (m, 10H, CH), 7.53-7.56 (m, 1H, CH); $\delta_C$ (100 MHz, d-CDCl$_3$) 26.0, 26.7, 34.3, 35.8, 44.1, 52.3, 53.1, 67.1, 70.9, 34.4, 44.2, 48.6, 66.6, 72.2, 114.6, 121.9, 126.8, 127.1, 127.5, 127.9, 128.1, 128.3, 128.5, 128.6, 131.3, 132.3, 133.2, 133.4, 135.5, 135.7, 147.6, 157.9, 165.1, 166.3; LRMS (ES+) Calcd for [C$_{43}$H$_{39}$F$_5$N$_2$O$_6$S+Na] 829.84 found 829.28.

EXAMPLE 25

Compound 7c

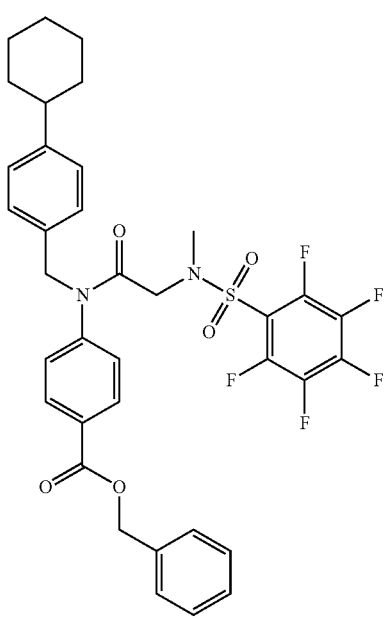 [SMILES: CN(CC(=O)N(Cc1ccc(C2CCCCC2)cc1)c1ccc(C(=O)OCc2ccccc2)cc1)S(=O)(=O)c1c(F)c(F)c(F)c(F)c1F]

benzyl 4-(N-(4-cyclohexylbenzyl)-2-(2,3,4,5,6-pentafluoro-N-methylphenylsulfonamido)acetamido)benzoate Chemical Formula: $C_{36}H_{33}F_5N_2O_5S$ Molecular Weight: 700.71

Compound 7c was synthesized according to general procedure h, yielding the final product 7c as a white solid (78%). $\delta_H$ (400 MHz, d-CDCl$_3$) 1.28-1.48 (m, 5H, CH$_2$), 1.71-1.93 (m, 5H, CH$_2$), 2.42-2.55 (m, 1H, CH), 3.10 (s, 3H, CH$_3$), 3.96 (s, 2H, CH$_2$), 4.79 (s, 2H, CH$_2$), 5.38 (s, 2H, CH$_2$), 6.90 (d, J=8.0 Hz, 2H, CH), 7.10-7.16 (m, 4H, CH), 7.33-7.47 (m, 5H, CH), 8.10 (d, J=8.0 Hz, 2H, CH); $\delta_C$ (100 MHz, d-CDCl$_3$) 26.1, 26.8, 34.3, 35.8, 44.1, 52.2, 53.0, 66.9, 126.9, 128.2, 128.3, 128.4, 128.5, 128.6, 131.4, 133.1, 135.5, 147.8, 165.1, 165.7; LRMS (ES+) Calcd for [$C_{36}H_{33}F_5N_2O_5S$+H] 723.19 found 723.13.

EXAMPLE 26

Compound 7d

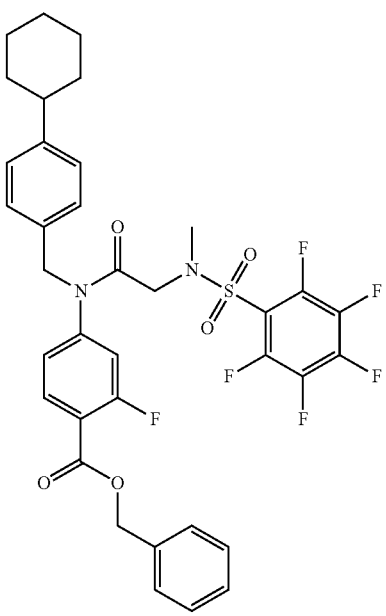 [SMILES: CN(CC(=O)N(Cc1ccc(C2CCCCC2)cc1)c1ccc(C(=O)OCc2ccccc2)c(F)c1)S(=O)(=O)c1c(F)c(F)c(F)c(F)c1F]

benzyl 4-(N-(4-cyclohexylbenzyl)-2-(2,3,4,5,6-pentafluoro-N-methylphenylsulfonamido)acetamido)-2-fluorobenzoate Chemical Formula: $C_{36}H_{32}F_6N_2O_5S$ Molecular Weight: 718.7051

Compound 7d was synthesized according to general procedure h, yielding the final product 7d as a colorless oil. $\delta_H$ (400 MHz, d-CDCl$_3$) 1.23-1.46 (m, 5H, CH$_2$), 1.71-1.91 (m, 5H, CH$_2$), 2.42-2.52 (m, 1H, CH), 3.1 (s, 3H, CH$_3$), 3.98 (s, 2H, CH$_2$), 4.21 (s, 2H, CH$_2$), 4.76 (s, 2H, CH$_2$), 5.38 (s, 2H, CH$_2$), 6.81-6.91 (m, 2H, CH), 6.98 (d, J=7.9 Hz, 2H, CH), 7.32-7.47 (m, 5H, CH), 7.93-7.99 (m, 1H, CH); $\delta_C$ (100 MHz, d-CDCl$_3$) 25.9, 26.8, 34.2, 35.8, 44.2, 52.1, 52.9, 67.2, 106.5, 108.3, 116.9, 123.9, 127.2, 127.4, 127.7, 128.1, 128.4, 128.6, 132.7, 133.2, 135.1, 147.5, 162.9, 165.6; LRMS (ES+) Calcd for [$C_{36}H_{32}F_6N_2O_5S$+H] 718.19 found 719.32.

EXAMPLE 27

Compound 7f

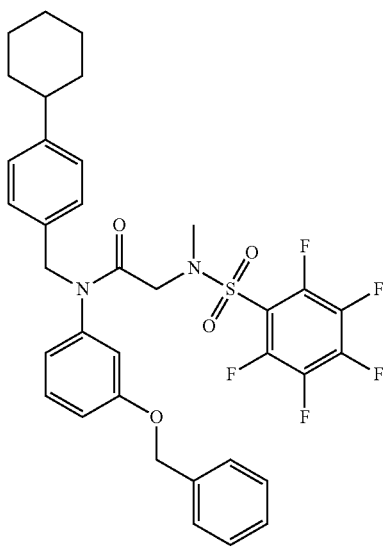 [SMILES: CN(CC(=O)N(Cc1ccc(C2CCCCC2)cc1)c1cccc(OCc2ccccc2)c1)S(=O)(=O)c1c(F)c(F)c(F)c(F)c1F]

N-(3-(benzyloxy)phenyl)-N-(4-cyclohexylbenzyl)-2-(2,3,4,5,6-pentafluoro-N-methylphenylsulfonamido)acetamide Chemical Formula: $C_{35}H_{33}F_5N_2O_4S$ Molecular Weight: 672.7045

Compound 7f was synthesized according to general procedure h, yielding the final product 7f as a white solid. $\delta_H$ (400 MHz, d-CDCl$_3$) 1.26-1.44 (m, 5H, CH$_2$), 1.72-1.91 (m, 5H, CH$_2$), 2.42-2.51 (m, 1H, CH), 3.11 (s, 3H, CH$_3$), 3.96 (s, 2H, CH$_2$), 4.65 (s, 2H, CH$_2$), 5.02 (s, 2H, CH$_2$), 6.74-6.82 (m, 2H, CH), 6.89-6.93 (m, 1H, CH), 6.95 (d, J=8.0 Hz, 2H, CH), 7.12 (d, J=7.9 Hz, 2H, CH), 7.31-7.45 (m, 5H, CH); $\delta_C$ (100 MHz, d-CDCl$_3$) 26.2, 25.9, 34.1, 35.3, 44.11, 51.2, 52.2, 71.3, 115.4, 123.5, 127.1, 128.1, 128.2, 128.9, 129.1, 132.5, 133.1, 136.1, 147.4, 157.8, 165.1; LRMS (ES+) Calcd for [C$_{35}$H$_{33}$F$_5$N$_2$O$_4$S+Na] 695.21 found 696.30.

EXAMPLE 28

Compound 7g dibenzyl 5-(N-(4-cyclohexylbenzyl)-2-(2,3,4,5,6-pentafluoro-N-methylphenylsulfonamido)acetamido)isophthalate Chemical Formula: $C_{44}H_{39}F_5N_2O_7S$ Molecular Weight: 834.8467

Compound 7g was synthesized according to general procedure h, yielding the final product 7g as a white solid. $\delta_H$ (400 MHz, d-(CDCl$_3$) 1.38-1.51 (m, 5H, CH$_2$), 1.75-1.81 (m, 5H, CH$_2$), 2.43-2.52 (m, 1H, CH), 3.11 (s, 3H, CH$_3$), 3.91 (s, 2H, CH$_2$), 4.69 (s, 2H, CH$_2$), 5.31 (s, 4H, CH$_2$), 7.13-7.18 (m, 4H, CH), 7.37-7.52 (m, 10H, CH), 7.79-7.85 (m, 2H, CH), 8.40 (s, 1H, CH); $\delta_C$ (100 MHz, d-CDCl$_3$) 26.3, 26.6, 34.5, 35.1, 35.6, 48.2, 49.3, 67.1, 68.4, 117.2, 118.1, 120.2, 126.3, 126.8, 127.3, 127.7, 127.9, 134.5, 138.1, 138.4, 140.3, 141.1, 144.5, 147.7, 165.1, 166.4, 166.9; LRMS (ES+) Calcd for [C$_{44}$H$_{39}$F$_5$N$_2$O$_7$S+H] 835.61 found 836.17.

EXAMPLE 29

Compound 7h

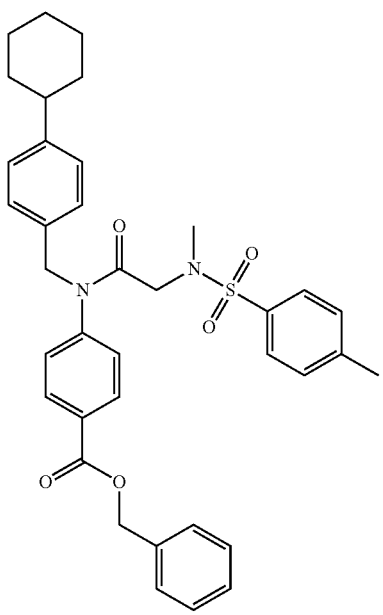 [SMILES: Cc1ccc(S(=O)(=O)N(C)CC(=O)N(Cc2ccc(C3CCCCC3)cc2)c2ccc(C(=O)OCc3ccccc3)cc2)cc1]

benzyl 4-(N-(4-cyclohexylbenzyl)-2-(N,4-dimethylphenyl-sulfonamido)acetamido)benzoate Chemical Formula: $C_{37}H_{40}N_2O_5S$ Molecular Weight: 624.79

Compound 7h was synthesized according to general procedure h, yielding the final product 7h as a white solid (91%). $\delta_H$ (400 MHz, d-CDCl$_3$) 1.26-1.46 (m, 5H, CH$_2$), 1.70-1.93 (m, 5H, CH$_2$), 2.40 (s, 3H, CH$_3$), 2.43-2.53 (m, 1H, CH), 2.87 (s, 3H, CH$_3$), 3.76 (s, 2H, CH$_2$), 4.82 (s, 2H, CH$_2$), 5.38 (s, 2H, CH$_2$), 7.04 (d, J=8.0 Hz, 2H, CH), 7.11 (s, J=8.1 Hz, 2H, CH), 7.26 (d, J=8.0 Hz, 2H, CH), 7.32-7.43 (m, 5H, CH), 7.45 (d, J=8.0 Hz, 2H, CH), 7.63 (d, J=8.3 Hz, 2H, CH), 8.10 (d, J=8.3 Hz, 2H, CH); $\delta_C$ (100 MHz, d-CDCl$_3$) 21.4, 26.0, 26.8, 34.3, 35.7, 44.1, 51.5, 52.9, 66.9, 70.2, 126.9, 127.4, 128.2, 128.3, 128.6, 129.4, 129.4, 131.2, 133.5, 135.2, 135.6, 143.3, 144.9, 147.5, 165.3, 166.6 LRMS (ES+) Calcd for [C$_{37}$H$_{40}$N$_2$O$_5$S+H] 625.27 found 625.31.

EXAMPLE 30

Compound 7i

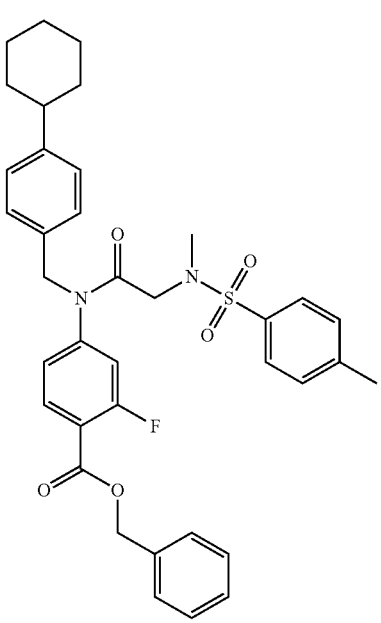 [SMILES: Cc1ccc(S(=O)(=O)N(C)CC(=O)N(Cc2ccc(C3CCCCC3)cc2)c2ccc(C(=O)OCc3ccccc3)c(F)c2)cc1]

benzyl 4-(N-(4-cyclohexylbenzyl)-2-(N,4-dimethylphenyl-sulfonamido)acetamido)-2-fluorobenzoate Chemical Formula: $C_{37}H_{39}FN_2O_5S$ Molecular Weight: 642.78

Compound 7i was synthesized according to general procedure h, yielding the final product 7i as a white solid (80%). $\delta_H$ (400 MHz, d-CDCl$_3$) 1.28-1.46 (m, 5H, CH$_2$), 1.70-1.93 (m, 5H, CH$_2$), 2.41 (s, 3H, CH$_3$), 2.45-2.51 (m, 1H, CH), 2.86 (s, 3H, CH$_3$), 3.76 (s, 2H, CH$_2$), 4.82 (s, 2H, CH$_2$), 5.38 (s, 2H, CH$_2$), 6.82-6.93 (m, 2H, CH), 7.03 (d, J=8.2 Hz, 2H, CH), 7.12 (d, J=8.2 Hz, 2H, CH), 7.27 (s, J=8.0 Hz, 2H, CH), 7.30-7.46 (m, 5H, CH), 7.63 (d, J=8.0 Hz, 2H, CH), 7.93-7.98 (m, 1H, CH); $\delta_C$ (100 MHz, d-CDCl$_3$) 21.4, 26.0, 26.7, 34.2, 35.8, 44.1, 51.6, 52.9, 67.2, 71.3, 126.9, 127.4, 128.1, 128.3, 128.4, 128.6, 129.4, 133.2, 135.1, 135.3, 143.3, 147.3, 147.8, 163.1, 163.4, 166.6; LRMS (ES+) Calcd for [C$_{37}$H$_{39}$FN$_2$O$_5$S+H] 643.26 found 643.39.

EXAMPLE 31

Compound 7j

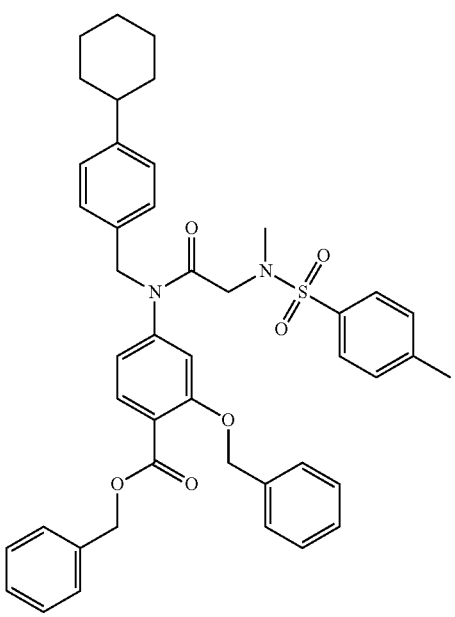 [SMILES: Cc1ccc(S(=O)(=O)N(C)CC(=O)N(Cc2ccc(C3CCCCC3)cc2)c2ccc(C(=O)OCc3ccccc3)c(OCc3ccccc3)c2)cc1]

benzyl 2-(benzyloxy)-4-(N-(4-cyclohexylbenzyl)-2-(N,4-dimethylphenylsulfonamido)acetamido)benzoate Chemical Formula: $C_{44}H_{46}N_2O_6S$ Molecular Weight: 730.91

Compound 7j was synthesized according to general procedure h, yielding the final product 7j as a yellow oil. $\delta_H$ (400 MHz, d-CDCl$_3$) 1.21-1.41 (m, 5H, CH$_2$), 1.71-1.88 (m, 5H, CH$_2$), 2.30 (s, 3H, CH$_3$), 2.40-2.48 (m, 1H, CH), 3.1 (s, 3H, CH$_3$), 3.58 (s, 2H, CH$_2$), 4.57 (s, 2H, CH$_2$), 4.79 (s, 2H, CH$_2$), 5.28 (s, 2H, CH$_2$), 6.59 (dd, J=8.2 and 1.5 Hz, 1H, CH), 6.93 (d, J=8.0 Hz, 2H, CH), 7.02 (d, J=8.0 Hz, 2H, CH), 7.14-7.35 (m, 12H, CH), 7.52 (d, J=8.2 Hz, 2H, CH), 7.75 (d, J=8.2 Hz, 2H, CH); $\delta_C$ (100 MHz, d-CDCl$_3$) 21.4, 25.9, 26.4, 34.2, 35.7, 44.1, 51.1, 52.3, 66.5, 70.4, 114.1, 119.9, 120.5, 126.8, 126.9, 127.3, 127.8, 128.0, 128.1, 128.4, 128.5, 128.7, 129.3, 133.0, 133.8, 135.2, 135.6, 135.7, 143.1, 144.9, 147.6, 158.6, 165.2, 166.6. LRMS (ES+) Calcd for [C$_{44}$H$_{46}$N$_2$O$_6$S+H] 731.32 found 731.28.

EXAMPLE 32

Compound 7k

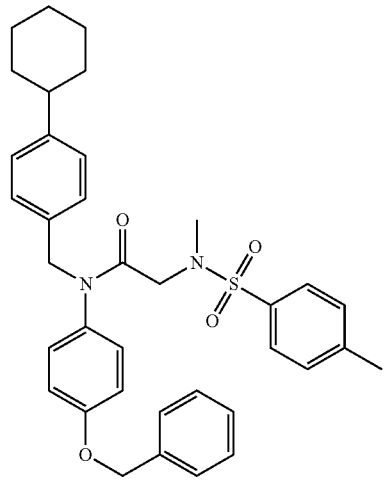 [SMILES: Cc1ccc(S(=O)(=O)N(C)CC(=O)N(Cc2ccc(C3CCCCC3)cc2)c2ccc(OCc3ccccc3)cc2)cc1]

N-(4-(benzyloxy)phenyl)-N-(4-cyclohexylbenzyl)-2-(N,4-dimethylphenylsulfonamido)acetamide Chemical Formula: $C_{36}H_{40}N_2O_4S$ Molecular Weight: 596.78

Compound 7k was synthesized according to general procedure h, yielding the final product as a white solid. $\delta_H$ (400 MHz, d-CDCl$_3$) 1.31-1.46 (m, 5H, CH$_2$), 1.71-1.91 (m, 5H, CH$_2$), 2.42 (s, 3H, CH$_3$), 2.44-2.51 (m, 1H, CH), 2.89 (s, 3H, CH$_3$), 3.74 (s, 2H, CH$_2$), 4.73 (s, 2H, CH$_2$), 5.05 (s, 2H, CH$_2$), 6.89 (d, J=8.8 Hz, 2H, CH), 6.93 (s, J=8.8 Hz, 2H, CH), 7.05 (d, J=8.0 Hz, 2H, CH), 7.10 (d, J=8.0 Hz, 2H, CH), 7.27 (d, J=8.2 Hz, 2H, CH), 7.31-7.45 (m, 5H, CH), 7.67 (d, J=8.2 Hz, 2H, CH); $\delta_C$ (100 MHz, d-CDCl$_3$) 21.4, 26.1, 26.8, 34.3, 35.7, 44.1, 51.3, 53.1, 70.2, 115.7, 126.7, 127.4, 128.1, 128.5, 128.7, 129.3, 129.4, 133.5, 134.2, 135.6, 136.2, 143.1, 147.3, 158.5, 167.2; LRMS (ES+) Calcd for [C$_{36}$H$_{40}$N$_2$O$_4$S+Hg/5] 597.28 found 597.34.

EXAMPLE 33

Compound 8

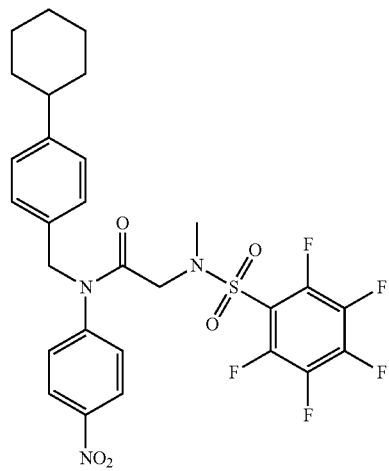 [SMILES: CN(CC(=O)N(Cc1ccc(C2CCCCC2)cc1)c1ccc([N+](=O)[O-])cc1)S(=O)(=O)c1c(F)c(F)c(F)c(F)c1F]

N-(4-cyclohexylbenzyl)-N-(4-nitrophenyl)-2-(2,3,4,5,6-pentafluoro-N-methylphenylsulfonamido)acetamide Chemical Formula: $C_{28}H_{26}F_5N_3O_5S$ Molecular Weight: 611.5802

Compound 8 was synthesized according to general procedure h, yielding the final product 8 as a yellow oil. $\delta_H$ (400 MHz, d-CDCl$_3$) 1.26-1.44 (m, 5H, CH$_2$), 1.69-1.86 (m, 5H, CH$_2$), 2.41-2.53 (m, 1H, CH), 3.10 (s, 3H, CH$_3$), 3.98 (s, 2H, CH$_2$), 4.78 (s, 2H, CH$_2$), 6.97 (d, J=7.5 Hz, 2H, CH), 7.13 (d, J=7.5 Hz, 2H, CH), 7.21 (d, J=8.3 Hz, 2H, CH), 8.24 (d, J=8.6 Hz, 2H, CH); $\delta_C$ (100 MHz, d-CDCl$_3$) 25.9, 26.6, 34.2, 35.8, 44.1, 52.2, 53.1, 125.2, 127.2, 128.4, 129.2, 132.5, 148.2, 146.9, 147.8, 165.6; HRMS (ES+) Calcd for [$C_{28}H_{26}F_5N_3O_5S$+H] 612.5881 found 612.1582; HPLC (I) $t_R$=31.615 min (100.0%), (II) $t_R$=48.560 min (100.0%).

EXAMPLE 34

Compound 9

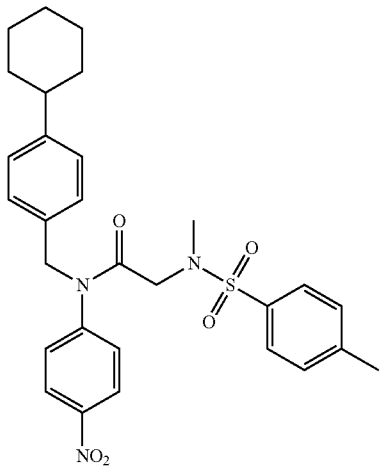 [SMILES: Cc1ccc(S(=O)(=O)N(C)CC(=O)N(Cc2ccc(C3CCCCC3)cc2)c2ccc([N+](=O)[O-])cc2)cc1]

N-(4-cyclohexylbenzyl)-2-(N,4-dimethylphenylsulfonamido)-N-(4-nitrophenyl)acetamide Chemical Formula: $C_{29}H_{33}N_3O_5S$ Molecular Weight: 535.6544

Compound 9 was synthesized according to general procedure h, yielding the final product 9 as a yellow oil. $\delta_H$ (400 MHz, d-CDCl$_3$) 1.27-1.44 (m, 5H, CH$_2$), 1.68-1.89 (m, 5H, CH$_2$), 2.41 (s, 3H, CH$_3$), 2.43-2.50 (m, 1H, CH), 2.83 (s, 3H, CH$_3$), 3.76 (s, 2H, CH$_2$), 4.86 (s, 2H, CH$_2$), 7.04 (d, J=7.9 Hz, 2H, CH), 7.11 (d, J=7.9 Hz, 2H, CH), 7.21-7.29 (m, 4H, CH), 7.61 (d, J=8.3 Hz, 2H, CH), 8.21 (d, J=8.3 Hz, 2H, CH); $\delta_C$ (100 MHz, d-CDCl$_3$) 21.4, 25.7, 26.6, 34.3, 35.8, 44.2, 52.1, 53.1, 124.9, 127.1, 127.4, 128.4, 128.9, 129.5, 133.1, 134.6, 143.4, 146.6, 146.9, 147.8, 166.6; HRMS (ES+) Calcd for [$C_{29}H_{33}N_3O_5S$+H] 536.6624 found 536.2222; HPLC (I) $t_R$=28.939 min (100.0%), (II) $t_R$=46.607 min (100.0%).

EXAMPLE 35

Compound 10

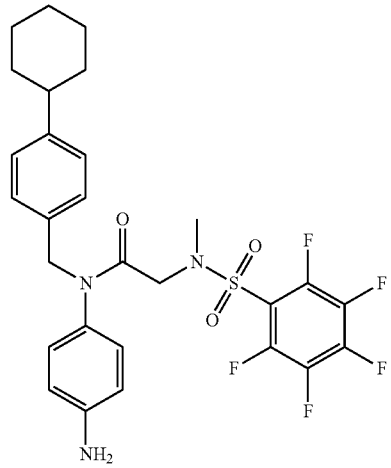 [SMILES: CN(CC(=O)N(Cc1ccc(C2CCCCC2)cc1)c1ccc(N)cc1)S(=O)(=O)c1c(F)c(F)c(F)c(F)c1F]

N-(4-aminophenyl)-N-(4-cyclohexylbenzyl)-2-(2,3,4,5,6-pentafluoro-N-methylphenylsulfonamido)acetamide Chemical Formula: $C_{28}H_{28}F_5N_3O_3S$ Molecular Weight: 581.5972

Compound 10 was synthesized according to general procedure j, yielding the final product 10 as a colorless oil. $\delta_H$ (400 MHz, d-CDCl$_3$) 1.25-1.43 (m, 5H, CH$_2$), 1.70-1.88 (m, 5H, CH$_2$), 2.41-2.52 (m, 1H, CH), 3.10 (s, 3H, CH$_3$), 3.78 (s, 2H, CH$_2$), 3.96 (s, 2H, CH$_2$), 4.63 (s, 2H, NH$_2$), 6.59 (d, J=8.3 Hz, 2H, CH), 6.71 (d, J=8.3 Hz, 2H, CH), 6.97 (d, J=7.7 Hz, 2H, CH), 7.10 (d, J=7.7 Hz, 2H, CH); $\delta_C$ (100 MHz, d-CDCl$_3$) 25.9, 26.3, 34.1, 35.6, 44.2, 51.5, 53.2, 120.9, 126.2, 127.7, 129.1, 131.3, 135.1, 136.9, 147.1, 165.8; HRMS (ES+) Calcd for [$C_{28}H_{28}F_5N_3O_3S$+H] 582.6052 found 582.1859; HPLC (I) $t_R$=20.503 min (94.4%), (II) $t_R$=40.315 min (95.3%).

EXAMPLE 36

Compound 11

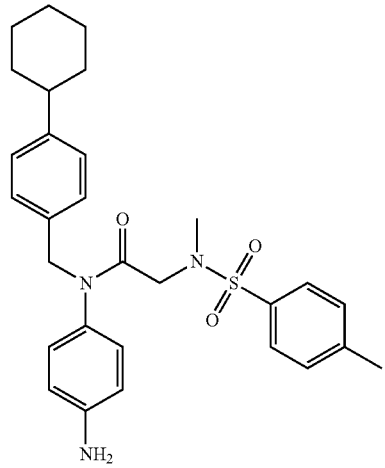

N-(4-aminophenyl)-N-(4-cyclohexylbenzyl)-2-(N,4-dimethylphenylsulfonamido)acetamide
Chemical Formula: $C_{29}H_{35}N_3O_3S$
Molecular Weight: 505.6715

Compound 11 was synthesized according to general procedure j, yielding the final product 11 as a yellow oil. $\delta_H$ (400 MHz, d-CDCl$_3$) 1.25-1.45 (m, 5H, CH$_2$), 1.71-1.89 (m, 5H, CH$_2$), 2.40 (s, 3H, CH$_3$), 2.42-2.53 (m, 1H, CH), 2.87 (s, 3H, CH$_3$), 3.74 (s, 2H, CH$_2$), 4.71 (s, 2H, CH$_2$), 6.57 (d, J=8.6 Hz, 2H, CH), 6.71 (d, J=8.6 Hz, 2H, CH), 7.02-7.11 (m, 4H, CH), 7.25 (d, J=7.0 Hz, 2H, CH), 7.65 (d, J=8.2 Hz, 2H, CH); $\delta_C$ (100 MHz, d-CDCl$_3$) 21.4, 26.1, 26.7, 34.3, 35.7, 44.1, 51.2, 53.1, 115.5, 126.6, 127.4, 128.8, 129.1, 129.3, 130.9, 134.4, 135.6, 143.0, 146.6, 147.1, 167.4; HRMS (ES+) Calcd for [C$_{29}$H$_{35}$N$_3$O$_3$S+H] 506.6794 found 506.2467; HPLC (I) t$_R$=15.995 min (100.0%), (II) t$_R$=36.789 min (100.0%).

EXAMPLE 37

Compound 12

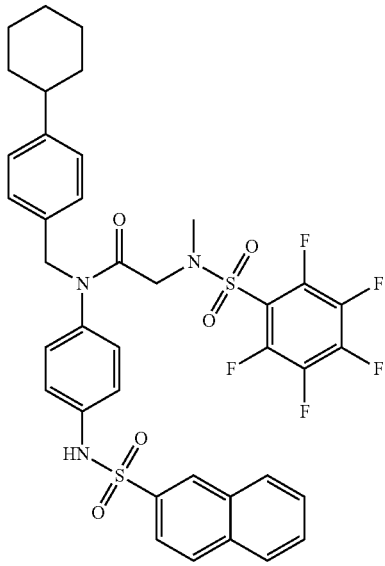 [SMILES: CN(CC(=O)N(Cc1ccc(C2CCCCC2)cc1)c1ccc(NS(=O)(=O)c2ccc3ccccc3c2)cc1)S(=O)(=O)c1c(F)c(F)c(F)c(F)c1F]

N-(4-cyclohexylbenzyl)-N-(4-(naphthalene-2-sulfonamido)phenyl)-2-(2,3,4,5,6-pentafluoro-N-methylphenylsulfonamido)acetamide
Chemical Formula: $C_{38}H_{34}F_5N_3O_5S_2$
Molecular Weight: 771.8157

Compound 12 was synthesized according to general procedure d, yielding the final product 12 as a yellow oil. $\delta_H$ (400 MHz, d-CDCl$_3$) 1.30-1.43 (m, 5H, CH$_2$), 1.71-1.90 (m, 5H, CH$_2$), 2.37-2.48 (m, 1H, CH), 3.01 (s, 3H, CH$_3$), 3.75 (s, 2H, CH$_2$), 4.58 (s, 2H, CH$_2$), 6.79 (d, J=8.3 Hz, 2H, CH), 6.84 (d, J=7.9 Hz, 2H, CH), 6.99 (d, J=7.9 Hz, 2H, CH), 7.09 (d, J=8.4 Hz, 2H, CH), 7.43 (brs, 1H, NH), 7.59-7.71 (m, 2H, CH), 7.74-7.79 (m, 1H, CH), 7.86-7.95 (m, 3H, CH), 8.35-8.41 (m, 1H, CH); $\delta_C$ (100 MHz, d-CDCl$_3$) 26.0, 26.7, 34.2, 35.7, 44.0, 52.1, 52.9, 121.8, 122.0, 126.7, 127.7, 127.8, 128.4, 128.8, 129.1, 129.2, 129.5, 131.8, 133.2, 134.9, 135.5, 136.6, 137.1, 147.6, 165.9; HRMS (ES+) Calcd for [C$_{38}$H$_{34}$F$_5$N$_3$O$_5$S$_2$+H] 772.8236 found 772.1938; HPLC (I) t$_R$=32.086 min (95.8%), (II) t$_R$=47.265 min (96.9%).

EXAMPLE 38

Compound 13

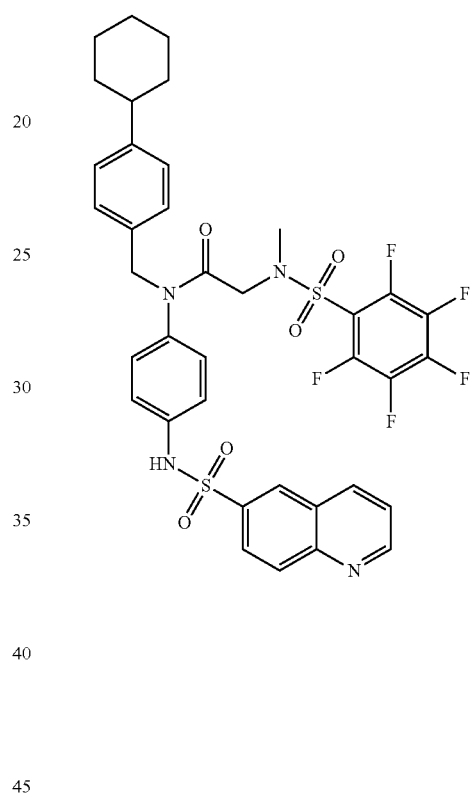

N-(4-cyclohexylbenzyl)-2-(2,3,4,5,6-pentafluoro-N-methylphenylsulfonamido)-N-(4-(quinoline-6-sulfonamido)phenyl)acetamide
Chemical Formula: $C_{37}H_{33}F_5N_4O_5S_2$
Molecular Weight: 772.8037

Compound 13 was synthesized according to general procedure d, yielding the final product 15 as a yellow oil. $\delta_H$ (400 MHz, d-CDCl$_3$) 1.28-1.44 (m, 5H, CH$_2$), 1.70-1.88 (m, 5H, CH$_2$), 2.38-2.48 (m, 1H, CH), 3.01 (s, 3H, CH$_3$), 3.72 (s, 2H, CH$_2$), 4.55 (s, 2H, CH$_2$), 6.72 (d, J=8.4 Hz, 2H, CH), 6.82 (d, J=7.9 Hz, 2H, CH), 6.98-7.06 (m, 4H, CH), 7.59-7.68 (m, 2H, CH), 8.10 (d, J=8.0 Hz, 1H, CH), 8.32 (d, J=7.5 Hz, 1H, CH), 8.36 (d, J=7.1 Hz, 1H, CH), 8.61 (brs, 1H, NH), 9.12-9.16 (m, 1H, CH); $\delta_C$ (100 MHz, d-CDCl$_3$) 25.9, 26.7, 34.2, 35.7, 44.0, 52.1, 52.9, 122.4, 122.8, 125.6, 126.7, 128.28, 128.74, 128.82, 131.5, 133.2, 133.84, 135.1, 136.7, 137.3, 137.5, 142.9, 147.5, 151.2, 166.0; HRMS (ES+) Calcd for [C$_{37}$H$_{33}$F$_5$N$_4$O$_5$S$_2$+H] 773.8117 found 773.1871; HPLC (I) t$_R$=29.764 min (95.6%), (II) t$_R$=47.224 min (97.8%).

EXAMPLE 39

Compound 14

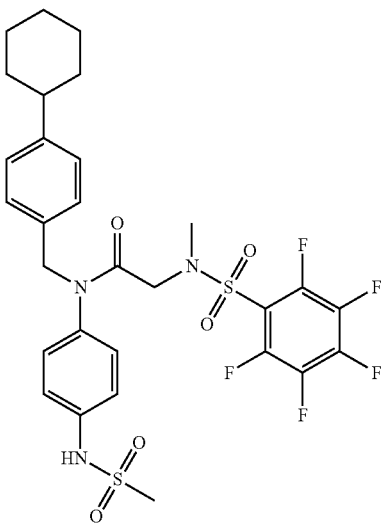 [SMILES: CN(CC(=O)N(Cc1ccc(C2CCCCC2)cc1)c1ccc(NS(C)(=O)=O)cc1)S(=O)(=O)c1c(F)c(F)c(F)c(F)c1F]

N-(4-cyclohexylbenzyl)-N-(4-(methylsulfonamido)phenyl)-2-(2,3,4,5,6-pentafluoro-N-methylphenylsulfonamido)acetamide Chemical Formula: $C_{29}H_{30}F_5N_3O_5S_2$ Molecular Weight: 659.6876

Compound 14 was synthesized according to general procedure d, yielding the final product 13 as a yellow oil. $\delta_H$ (400 MHz, d-CDCl$_3$) 1.26-1.48 (m, 5H, CH$_2$), 1.69-1.89 (m, 5H, CH$_2$), 2.41-2.52 (m, 1H, CH), 3.05 (s, 3H, CH$_3$), 3.10 (s, 3H, CH$_3$), 3.94 (s, 2H, CH$_2$), 4.68 (s, 2H, CH$_2$), 6.93-7.02 (m, 4H, CH), 7.10 (d, 2H, J=7.7 Hz, CH), 7.21 (d, J=8.4 Hz, 2H, CH), 7.41 (brs, 1H, NH); $\delta_C$ (100 MHz, d-CDCl$_3$) 26.0, 26.7, 34.3, 35.8, 39.7, 44.10, 52.20, 53.09, 120.7, 126.9, 128.4, 129.5, 133.3, 136.4, 137.5, 147.6, 166.1; HRMS (ES+) Calcd for [C$_{29}$H$_{30}$F$_5$N$_3$O$_5$S$_2$+H] 660.6956 found 660.1634; HPLC (I) t$_R$=26.394 min (95.55%), (II) t$_R$=44.372 min (94.33%).

EXAMPLE 40

Compound 15

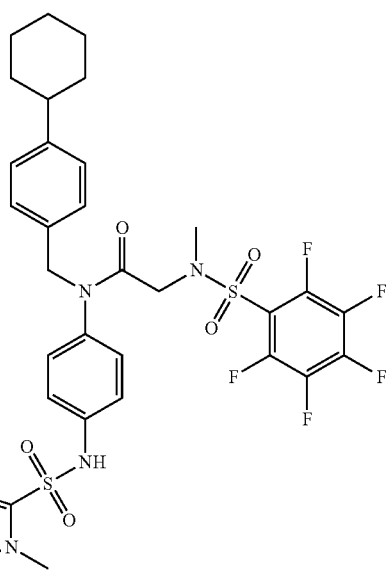

N-(4-cyclohexylbenzyl)-N-(4-(1-methyl-1H-imidazole-5-sulfonamido)phenyl)-2-(2,3,4,5,6-pentafluoro-N-methylphenylsulfonamido)acetamide Chemical Formula: $C_{32}H_{32}F_5N_5O_5S_2$ Exact Mass: 725.1765

Compound 15 was synthesized according to general procedure d, yielding the final product 14 as a yellow oil. $\delta_H$ (400 MHz, d-CDCl$_3$) 1.30-1.47 (m, 5H, CH$_2$), 1.70-1.94 (m, 5H, CH$_2$), 2.42-2.53 (m, 1H, CH), 3.07 (s, 3H, CH$_3$), 3.70 (s, 3H, CH$_3$), 3.86 (s, 2H, CH$_2$), 4.62 (s, 2H, CH$_2$), 6.85 (d, J=8.3 Hz, 2H, CH), 6.94 (d, J=7.7 Hz, 2H, CH), 7.10 (d, J=7.9 Hz, 2H, CH), 7.34 (d, J=8.4 Hz, 2H, CH), 7.41 (s, 1H, CH), 7.56 (s, 1H, CH), 10.23 (s, 1H, CH); $\delta_C$ (100 MHz, d-CDCl$_3$) 26.0, 26.7, 34.1, 34.3, 35.8, 44.0, 52.1, 53.0, 122.3, 124.9, 126.8, 128.2, 128.8, 133.4, 136.3, 137.8, 138.7, 139.3, 147.5, 166.2; HRMS (ES+) Calcd for [C$_{32}$H$_{32}$F$_5$N$_5$O$_5$S$_2$+H] 726.1843 found 726.1821; HPLC (I) t$_R$=23.409 min (94.7%), (II) t$_R$=42.488 min (94.9%).

EXAMPLE 41

Compound 16

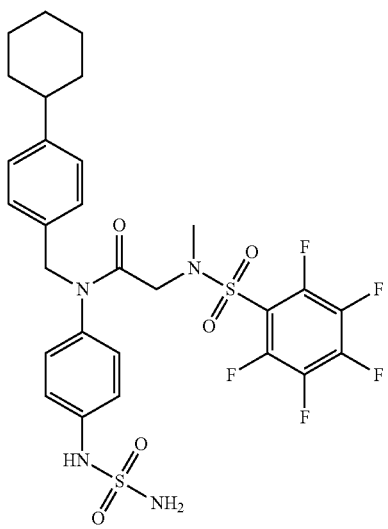 [SMILES: CN(CC(=O)N(Cc1ccc(C2CCCCC2)cc1)c1ccc(NS(N)(=O)=O)cc1)S(=O)(=O)c1c(F)c(F)c(F)c(F)c1F]

N-(4-cyclohexylbenzyl)-2-(2,3,4,5,6-pentafluoro-N-methylphenylsulfonamido)-N-(4-(sulfamoylamino)phenyl)acetamide Chemical Formula: $C_{28}H_{29}F_5N_4O_5S_2$ Molecular Weight: 660.6757

Compound 16 was synthesized according to general procedure d, yielding the final product X as a yellow oil. $\delta_H$ (400 MHz, d-CDCl$_3$) 1.28-1.44 (m, 5H, CH$_2$), 1.70-1.89 (m, 5H, CH$_2$), 2.41-2.50 (m, 1H, CH), 3.06 (s, 3H, CH$_3$), 3.92 (s, 2H, CH$_2$), 4.68 (s, 2H, CH$_2$), 5.10 (brs, 2H, NH$_2$) 6.94-7.01 (m, 4H, CH), 7.10 (d, J=7.9 Hz, 2H, CH), 7.19 (d, J=8.4 Hz, 2H, CH); $\delta_C$ (100 MHz, d-CDCl$_3$) 25.9, 26.7, 34.3, 35.7, 44.1, 52.2, 53.2, 121.0, 126.9, 128.4, 129.2, 133.3, 136.3, 137.6, 147.6, 166.3; HRMS (ES+) Calcd for [$C_{28}H_{29}F_5N_4O_5S_2$+H] 661.6836 found 661.1575; HPLC (I) $t_R$=23.259 min (90.9%), (II) $t_R$=42.445 min (91.4%).

EXAMPLE 42

Compound 17

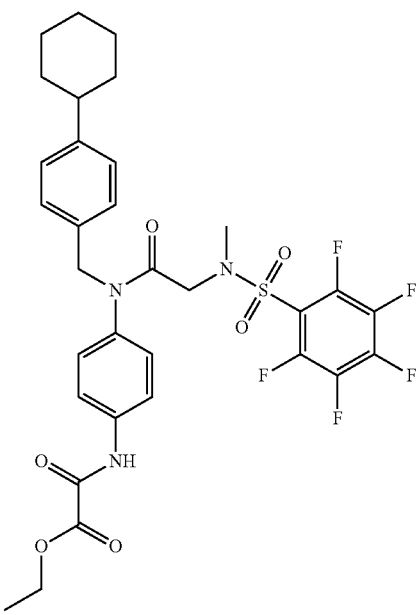 [SMILES: CCOC(=O)C(=O)Nc1ccc(N(Cc2ccc(C3CCCCC3)cc2)C(=O)CN(C)S(=O)(=O)c2c(F)c(F)c(F)c(F)c2F)cc1]

ethyl 2-((4-(N-(4-cyclohexylbenzyl)-2-(2,3,4,5,6-pentafluoro-N-methylphenylsulfonamido)acetamido)phenyl)amino)-2-oxoacetate Chemical Formula: $C_{32}H_{32}F_5N_3O_6S$ Molecular Weight: 681.6700

Compound 17 was synthesized according to general procedure k, yielding the final product 17 as a colorless oil. $\delta_H$ (400 MHz, d-CDCl$_3$) 1.32-1.46 (m, 8H, CH$_2$ and CH$_3$), 1.69-1.90 (m, 5H, CH$_2$), 2.41-2.52 (m, 1H, CH), 3.10 (s, 3H, CH$_3$), 3.94 (s, 2H, CH$_2$), 4.41 (q, J=7.2 Hz, 2H, CH$_2$), 4.70 (s, 2H, CH$_2$), 6.92-7.02 (m, 4H, CH), 7.10 (d, J=7.7 Hz, 2H, CH), 7.67 (d, J=8.3 Hz, 2H, CH), 9.02 (brs, 1H, NH); $\delta_C$ (100 MHz, d-CDCl$_3$) 13.9, 26.1, 26.8, 34.3, 35.9, 44.1, 52.2, 53.1, 63.8, 121.0, 126.9, 128.6, 129.1, 133.4, 136.7, 136.8, 147.7, 154.0, 160.6, 166.2; HRMS (ES+) Calcd for [$C_{32}H_{32}F_5N_3O_6S$+H] 682.6779 found 682.1994; HPLC (I) $t_R$=28.867 min (93.7%), (II) 46.469 min (95.6%).

EXAMPLE 43

Compound 18

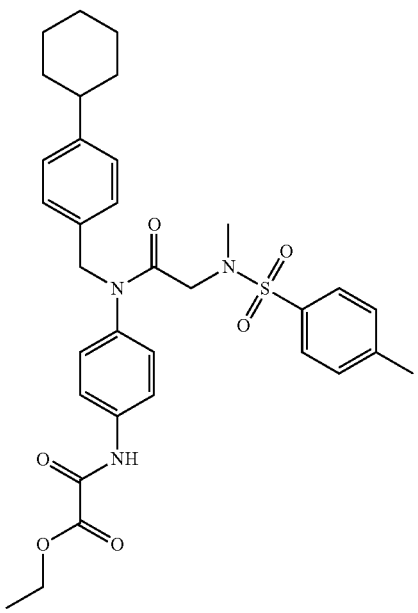 [SMILES: CCOC(=O)C(=O)Nc1ccc(N(Cc2ccc(C3CCCCC3)cc2)C(=O)CN(C)S(=O)(=O)c2ccc(C)cc2)cc1]

EXAMPLE 44

Compound 19a

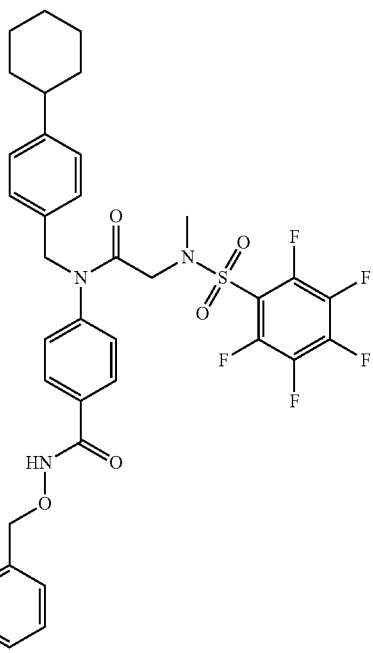

ethyl 2-((4-(N-(4-cyclohexylbenzyl)-2-(N,4-dimethylphenylsulfonamido)acetamido)phenyl)amino)-2-oxoacetate
Chemical Formula: $C_{33}H_{39}N_3O_6S$
Molecular Weight: 605.7443
Compound 18 was synthesized according to general procedure g, yielding the final product 18 as a colorless oil. $\delta_H$ (400 MHz, d-CDCl$_3$) 1.23-1.41 (m, 5H, CH$_2$), 1.42 (t, J=7.2 Hz, 3H, CH$_3$), 1.69-1.86 (m, 5H, CH$_2$), 2.40 (s, 3H, CH$_3$), 2.42-2.52 (m, 1H, CH), 2.85 (s, 3H, CH$_3$), 3.72 (s, 2H, CH$_2$), 4.41 (q, J=7.2 Hz, 2H, CH$_2$), 4.75 (s, 2H, CH$_2$), 6.95-7.05 (m, 4H, CH), 7.10 (d, J=7.8 Hz, 2H, CH), 7.24 (d, J=7.4 Hz, 2H, CH), 7.58-7.67 (m, 4H, CH), 9.01 (s, 1H, NH); $\delta_C$ (100 MHz, d-CDCl$_3$) 13.8, 21.4, 26.1, 26.7, 34.2, 35.6, 44.1, 51.4, 53.1, 63.7, 120.9, 126.7, 128.7, 129.2, 129.4, 133.9, 135.2, 136.4, 137.3, 143.2, 147.4, 154.1, 160.6, 166.7, 167.4; HRMS (ES+) Calcd for [C$_{33}$H$_{39}$N$_3$O$_6$S+H] 606.7522 found 606.2635; HPLC (I) t$_R$=25.724 min (100.0%), (II) t$_R$=44.185 min (100.0%).

N-(benzyloxy)-4-(N-(4-cyclohexylbenzyl)-2-(2,3,4,5,6-pentafluoro-N-methylphenylsulfonamido)acetamido) benzamide
Chemical Formula: $C_{36}H_{34}F_5N_3O_5S$
Molecular Weight: 715.73
Compound 19a was synthesized according to general procedure m, yielding the final product 19a as a white solid. $\delta_H$ (400 MHz, d-CDCl$_3$) 1.27-1.45 (m, 5H, CH$_2$), 1.69-1.91 (m, 5H, CH$_2$), 2.41-2.53 (m, 1H, CH), 3.10 (s, 3H, CH$_3$), 3.89 (s, 2H, CH$_2$), 4.71 (s, 2H, CH$_2$), 5.01 (s, 2H, CH$_2$), 6.90-7.10 (m, 4H, CH), 7.11-7.15 (m, 2H, CH), 7.33-7.45 (m, 5H, CH), 7.63-7.70 (m, 1H, CH), 8.10 (d, J=8.3 Hz, 1H, CH), 8.72-8.91 (brs, 1H, NH); $\delta_C$ (100 MHz, d-CDCl$_3$) 25.9, 26.7, 34.2, 35.8, 44.1, 52.2, 53.0, 78.4, 126.9, 128.4, 128.5, 128.6, 128.9, 129.1, 130.9, 131.8, 132.9, 148.0, 158.9, 159.9, 161.2, 166.7; LRMS (ES+) Calcd for [C$_{36}$H$_{34}$N$_3$F$_5$N$_3$O$_5$S+Na] 738.20 found 738.15.

EXAMPLE 45

Compound 19b

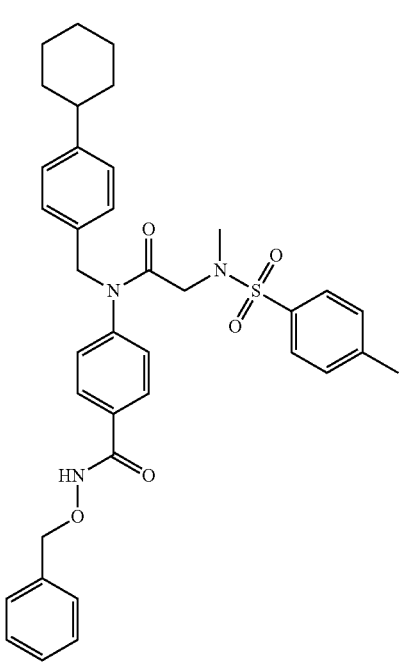 [SMILES: Cc1ccc(S(=O)(=O)N(C)CC(=O)N(Cc2ccc(C3CCCCC3)cc2)c2ccc(C(=O)NOCc3ccccc3)cc2)cc1]

N-(benzyloxy)-4-(N-(4-cyclohexylbenzyl)-2-(N,4-dimethylphenylsulfonamido)acetamido)benzamide Chemical Formula: $C_{37}H_{41}N_3O_5S$ Molecular Weight: 639.80

Compound 19b was synthesized according to general procedure m, yielding the final product 19b as a white solid. $\delta_H$ (400 MHz, d-CDCl$_3$) 1.28-1.45 (m, 5H, CH$_2$), 1.69-1.91 (m, 5H, CH$_2$), 2.41 (s, 3H, CH$_3$), 2.42-2.50 (m, 1H, CH), 2.83 (s, 3H, CH$_3$), 3.68 (s, 2H, CH$_2$), 4.77 (s, 2H, CH$_2$), 5.03 (s, 2H, CH$_2$), 6.97-7.11 (m, 6H, CH), 7.22-7.30 (m, 2H, CH), 7.33-7.48 (m, 5H, CH), 7.61 (d, J=8.3 Hz, 2H, CH), 7.65-7.71 (m, 2H, CH), 8.72-8.91 (brs, 1H, NH); $\delta_C$ (100 MHz, d-CDCl$_3$) 21.4, 25.9, 26.7, 34.3, 35.7, 44.1, 51.5, 52.9, 59.1, 117.1, 126.9, 127.4, 128.1, 128.5, 128.6, 128.7, 129.2, 129.4, 133.5, 135.1, 143.3, 147.6, 158.9, 159.9, 161.2, 166.7; LRMS (ES+) Calcd for [$C_{37}H_{41}N_3O_5S$+Na] 640.28 found 640.41.

EXAMPLE 46

Compound 20

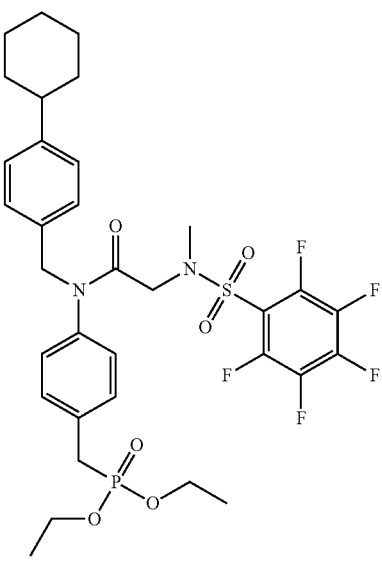 [SMILES: CCOP(=O)(Cc1ccc(N(Cc2ccc(C3CCCCC3)cc2)C(=O)CN(C)S(=O)(=O)c2c(F)c(F)c(F)c(F)c2F)cc1)OCC]

diethyl 4-(N-(4-cyclohexylbenzyl)-2-(2,3,4,5,6-pentafluoro-N-methylphenylsulfonamido)acetamido)benzylphosphonate Chemical Formula: $C_{33}H_{38}F_5N_2O_6PS$ Molecular Weight: 716.6954

Compound 20 was synthesized according to general procedure i, yielding the final product 20 as a viscous orange oil (74%). $\delta_H$ (400 MHz, d-CDCl$_3$) 1.23 (t, J=6.9 Hz, 6H, CH$_3$), 1.27-1.47 (m, 5H, CH$_2$), 1.70-1.87 (m, 5H, CH$_2$), 2.4-2.5 (m, 1H, CH), 3.08 (s, 3H, CH$_3$), 3.10 (s, 1H, CH), 3.16 (s, 1H, CH), 3.92 (s, 2H, CH$_2$), 3.95-4.07 (m, 4H, CH$_2$), 4.73 (s, 2H, CH$_2$), 6.98 (d, J=7.7 Hz, 2H, CH), 7.03 (d, J=7.7 Hz, 2H, CH), 7.10 (d, J=7.9 Hz, 2H, CH), 7.31-7.37 (m, 2H, CH); $\delta_C$ (100 MHz, d-CDCl$_3$) 15.1, 15.2, 25.7, 26.4, 34.1, 44.1, 51.5, 52.5, 62.3, 62.5, 126.4, 128.1, 128.2, 131.1, 131.2, 133.7, 138.9, 147.1, 166.7; HRMS (ES+) Calcd for [$C_{33}H_{38}F_5N_2O_6PS$+H] 717.7033 found 717.2198; HPLC (I) $t_R$=29.18 min (96.1%), (II) $t_R$=41.38 min (95.1%).

EXAMPLE 47

Compound 21

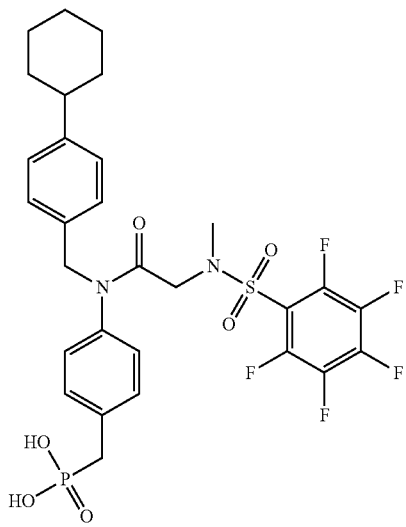 [SMILES: CN(CC(=O)N(Cc1ccc(C2CCCCC2)cc1)c1ccc(CP(=O)(O)O)cc1)S(=O)(=O)c1c(F)c(F)c(F)c(F)c1F]

(4-(N-(4-cyclohexylbenzyl)-2-(2,3,4,5,6-pentafluoro-N-methylphenylsulfonamido)acetamido)benzyl)phosphonic acid Chemical Formula: $C_{29}H_{30}F_5N_2O_6PS$ Molecular Weight: 660.5891

Compound 21 was synthesized according to general procedure n, yielding the final product 21 as a white solid. $\delta_H$ (400 MHz, d-(CDCl$_3$) 1.27-1.42 (m, 5H, CH$_2$), 1.70-1.87 (m, 5H, CH$_2$), 2.40-2.50 (m, 1H, CH), 3.03 (s, 3H, CH$_3$), 3.10 (s, 2H, CH$_2$), 3.90 (s, 2H, CH$_2$), 4.65 (s, 2H, CH$_2$), 6.89-7.05 (m, 4H, CH), 7.11 (d, J=8.1 Hz, 2H, CH), 7.20-7.31 (m, 2H, CH); $\delta_C$ (100 MHz, d-(CD$_3$)$_2$SO) 25.7, 26.4, 34.1, 35.5, 43.5, 44.1, 51.5, 53.4, 126.4, 128.1, 128.2, 131.1, 131.2, 133.7, 138.9, 147.1, 166.7; HRMS (ES+) Calcd for [C$_{29}$H$_{30}$P$_5$N$_2$O$_6$PS+H] 661.5970 found 661.1566; HPLC (I) t$_R$=17.489 min (97.9%), (II) t$_R$=38.028 min (100.0%).

EXAMPLE 48

Compound 22

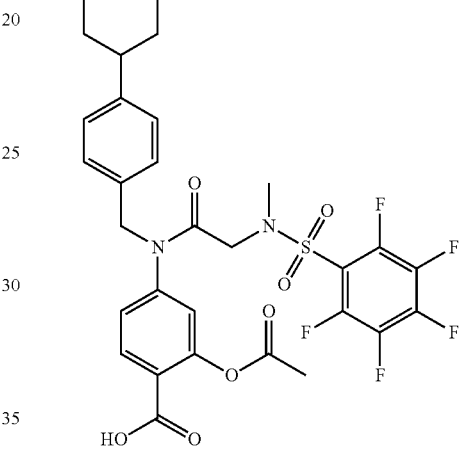

2-acetoxy-4-(N-(4-cyclohexylbenzyl)-2-(2,3,4,5,6-pentafluoro-N-methylphenylsulfonamido)acetamido)benzoic acid Chemical Formula: $C_{31}H_{29}F_5N_2O_7S$ Exact Mass: 668.1616

Compound 22 was synthesized according to general procedure o, yielding the final product 22 as a yellow oil. $\delta_H$ (400 MHz, d-CDCl$_3$) 1.32-1.48 (m, 5H, CH$_2$), 1.70-1.88 (m, 5H, CH$_2$), 2.32 (s, 3H, CH$_3$), 2.43-2.51 (m, 1H, CH), 3.10 (s, 3H, CH$_3$), 4.00 (s, 2H, CH$_2$), 4.76 (s, 2H, CH$_2$), 6.82 (s, 1H, CH), 6.93-7.02 (m, 3H, CH), 7.12 (d, J=7.7 Hz, 2H, CH), 8.10 (d, J=8.1 Hz, 1H, CH); $\delta_C$ (100 MHz, d-(CD$_3$)$_2$SO) 20.5, 26.0, 26.4, 33.6, 36.3, 44.3, 52.1, 53.4, 118.4, 120.0, 120.1, 123.0, 123.1, 125.6, 130.8, 139.2, 158.8, 159.0, 168.0; HRMS (ES+) Calcd for [C$_{31}$H$_{29}$F$_5$N$_2$O$_7$S+H] 669.1691 found 669.1701; HPLC (I) t$_R$=24.679 min (93.9%), (II) t$_R$=43.441 min (93.3%).

EXAMPLE 49

Compound 23

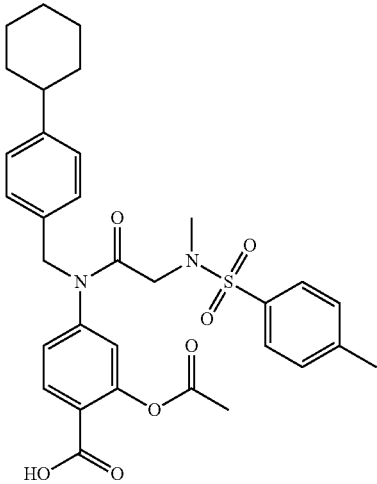 [SMILES: CC(=O)Oc1cc(N(Cc2ccc(C3CCCCC3)cc2)C(=O)CN(C)S(=O)(=O)c2ccc(C)cc2)ccc1C(=O)O]

2-acetoxy-4-(N-(4-cyclohexylbenzyl)-2-(N,4-dimethylphenylsulfonamido)acetamido)benzoic acid Chemical Formula: $C_{32}H_{36}N_2O_7S$ Molecular Weight: 592.7024

Compound 23 was synthesized according to general procedure o, yielding the final product 23 as a yellow oil. $\delta_H$ (400 MHz, d-CDCl$_3$) 1.24-1.47 (m, 5H, CH$_2$), 1.70-1.91 (m, 5H, CH$_2$), 2.32 (s, 3H, CH$_3$), 2.40 (s, 3H, CH$_3$), 2.43-2.52 (m, 1H, CH), 2.83 (s, 3H, CH$_3$), 3.77 (s, 2H, CH$_2$), 4.85 (s, 2H, CH$_2$), 6.87 (s, 1H, CH), 7.03 (d, 1H, J=8.1 Hz, CH), 7.11 (d, J=7.9 Hz, 2H, CH), 7.13 (d, J=7.9 Hz, 1H, CH), 7.27 (d, J=8.4 Hz, 2H, CH); $\delta_C$ (100 MHz, d-(CD$_3$)$_2$SO) 20.9, 25.8, 26.2, 29.5, 33.6, 36.3, 44.3, 52.1, 53.4, 118.4, 120.1, 120.5, 123.0, 123.1, 125.6, 130.8, 134.9, 139.2, 142.5, 147.1, 158.8, 159.0, 168.0, 169.2; HRMS (ES+) Calcd for [C$_{32}$H$_{36}$N$_2$O$_7$S+H] 593.7104 found 593.2316; HPLC (I) $t_R$=22.090 min (94.8%), (II) $t_R$=41.402 min (96.3%).

EXAMPLE 50

Compound 24

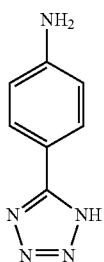 [SMILES: Nc1ccc(-c2nnn[nH]2)cc1]

4-(1H-tetrazol-5-yl)aniline

Chemical Formula: $C_7H_7N_5$

Molecular Weight: 161.1640

Compound 24 was synthesized according to procedure p, yielding the final product 24 as white powder (74%). $\delta_H$ (400 MHz, d-MeOD$_3$) 4.34 (brs, 2H, NH$_2$), 6.51 (d, J=8.9 Hz, 2H, CH), 7.71 (s, J=8.9 Hz, 2H, CH); $\delta_C$ (100 MHz, d-C$_2$D$_6$CO) 113.4, 121.6, 126.8, 143.1, 154.2; LRMS (ES+) Calcd for [C$_7$H$_7$N$_5$+H] 161.07 found 162.16.

EXAMPLE 51

Compound 25a

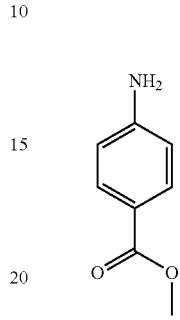

methyl 4-aminobenzoate

Chemical Formula: $C_8H_9NO_2$

Molecular Weight: 151.16

Compound 25a was synthesized according to general procedure q, yielding the final product 25a as a brown solid (91%). $\delta_H$ (400 MHz, d-CDCl$_3$) 3.83 (s, 3H, CH$_3$), 3.90-3.95 (brs, 2H, CH$_2$), 6.61 (d, J=8.8 Hz, 2H, CH), 7.84 (d, J=8.8 Hz, 2H, CH); $\delta_C$ (100 MHz, d-CDCl$_3$) 51.6, 114.1, 120.1, 131.5, 151.2, 167.4; LRMS (ES+) Calcd for [C$_8$H$_9$NO$_2$+H] 152.07 found 152.04.

EXAMPLE 52

Compound 25b

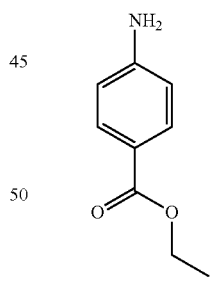

ethyl 4-aminobenzoate

Chemical Formula: $C_9H_{11}NO_2$

Molecular Weight: 165.19

Compound 25b was synthesized according to general procedure q, yielding the final product 25b as a brown solid (87%). $\delta_H$ (400 MHz, d-CDCl$_3$) 1.34 (t, J=7.0 Hz, 3H, CH$_3$), 3.95-4.02 (brs, 2H, NH$_2$), 4.31 (q, J=7.1 Hz, 2H, CH$_2$), 6.63 (d, J=8.0 Hz, 2H, CH), 7.86 (d, J=8.0 Hz, 2H, CH); $\delta_C$ (100 MHz, d-CDCl$_3$) 14.5, 60.2, 114.1, 120.2, 131.5, 152.1, 167.9; LRMS (ES+) Calcd for [C$_9$H$_{11}$NO$_2$+H] 166.09 found 166.1.

EXAMPLE 53

Compound 26

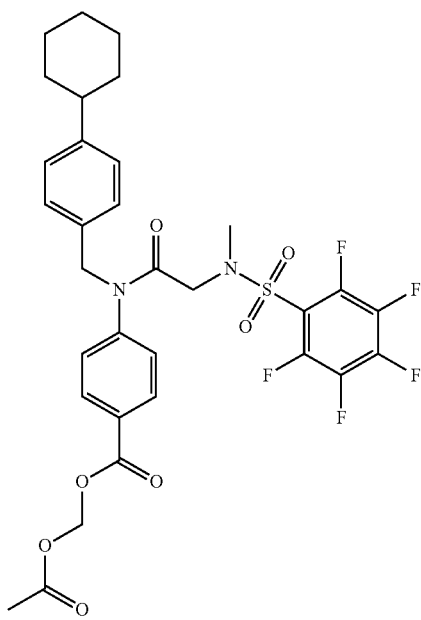 [SMILES: CC(=O)OCOC(=O)c1ccc(N(Cc2ccc(C3CCCCC3)cc2)C(=O)CN(C)S(=O)(=O)c2c(F)c(F)c(F)c(F)c2F)cc1]

acetoxymethyl 4-(N-(4-cyclohexylbenzyl)-2-(2,3,4,5,6-pentafluoro-N-methylphenylsulfonamido)acetamido)benzoate Chemical Formula: $C_{32}H_{31}F_5N_2O_7S$
Molecular Weight: 682.6548

Compound 26 was synthesized according to general procedure r, yielding the final product 26 as a yellow oil. $\delta_H$ (400 MHz, d-CDCl$_3$) 1.27-1.46 (m, 5H, CH$_2$), 1.69-1.92 (m, 5H, CH$_2$), 2.14 (s, 3H, CH$_3$), 2.42-2.52 (m, 1H, CH), 3.10 (s, 3H, CH$_3$), 3.94 (s, 2H, CH$_2$), 4.74 (s, 2H, CH$_2$), 5.98 (s, 2H, CH$_2$), 6.95 (d, J=7.5 Hz, 2H, CH), 7.05-7.15 (m, 4H, CH), 8.10 (d, J=8.3 Hz, 2H, CH); $\delta_C$ (100 MHz, d-CDCl$_3$) 20.6, 26.0, 26.7, 34.2, 35.8, 44.1, 52.2, 53.0, 79.6, 126.9, 127.8, 128.0, 128.2, 128.4, 131.7, 132.9, 147.8, 164.0, 165.7, 169.4; HRMS (ES+) Calcd for [C$_{32}$H$_{31}$P$_5$N$_2$O$_7$S+H] 683.6627 found 683.1877; HPLC (I) t$_R$=30.783 min (97.3%), (II) t$_R$=47.872 min (100.0%).

EXAMPLE 54

Compound 27

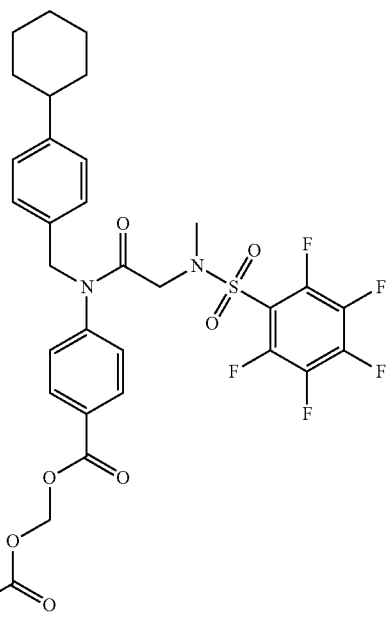

(pivaloyloxy)methyl 4-(N-(4-cyclohexylbenzyl)-2-(2,3,4,5,6-pentafluoro-N-methylphenylsulfonamido)acetamido)benzoate Chemical Formula: $C_{35}H_{37}F_5N_2O_7S$
Molecular Weight: 724.7345

Compound 27 was synthesized according to general procedure r, yielding the final product 27 as a white solid. $\delta_H$ (400 MHz, d-CDCl$_3$) 1.23 (s, 9H, CH$_3$), 1.34-1.44 (m, 5H, CH$_2$), 1.71-1.89 (m, 5H, CH$_2$), 2.42-2.52 (m, 1H, CH), 3.10 (s, 3H, CH$_3$), 3.94 (s, 2H, CH$_2$), 4.74 (s, 2H, CH$_2$), 5.99 (s, 2H, CH$_2$), 6.96 (d, J=7.7 Hz, 2H, CH), 7.06-7.13 (m, 4H, CH), 8.10 (d, J=8.6 Hz, 2H, CH); $\delta_C$ (100 MHz, d-CDCl$_3$) 26.0, 26.6, 26.7, 34.2, 35.8, 38.7, 44.1, 52.2, 53.0, 80.0; HRMS (ES+) Calcd for [C$_{35}$H$_{37}$F$_5$N$_2$O$_7$S+H] 725.7424 found 725.2339; HPLC (I) t$_R$=35.701 min (96.2%), (II) t$_R$=52.017 min (99.5%).

EXAMPLE 55

Compound 28

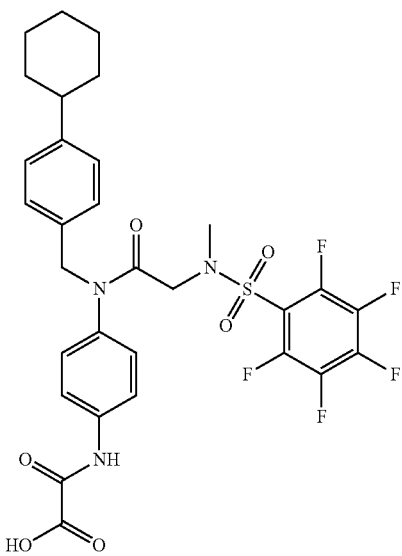 [SMILES: CN(CC(=O)N(Cc1ccc(C2CCCCC2)cc1)c1ccc(NC(=O)C(=O)O)cc1)S(=O)(=O)c1c(F)c(F)c(F)c(F)c1F]

2-((4-(N-(4-cyclohexylbenzyl)-2-(2,3,4,5,6-pentafluoro-N-methylphenylsulfonamido)acetamido)phenyl)amino)-2-oxoacetic acid Chemical Formula: $C_{30}H_{28}F_5N_3O_6S$ Molecular Weight: 653.62

Compound 28 was synthesized according to general procedure g, yielding the final product 28 as a white solid. $\delta_H$ (400 MHz, d-$(CD_3)_2SO$) 1.25-1.40 (m, 5H, $CH_2$), 1.62-1.80 (m, 5H, $CH_2$), 2.37-2.55 (m, 1H, CH), 2.97 (s, 3H, $CH_3$), 3.97 (s, 2H, $CH_2$), 4.67 (s, 2H, $CH_2$), 6.98 (d, J=7.5 Hz, 2H, CH), 7.03-7.13 (m, 4H, CH), 7.83 (d, J=7.9 Hz, 2H, CH), 10.54 (brs, 1H, NH); $\delta_C$ (100 MHz, d-$CDCl_3$) 26.1, 26.7, 34.2, 35.9, 44.2, 52.4, 53.3, 121.0, 126.9, 128.6, 129.1, 133.4, 136.7, 136.8, 147.7, 154.2, 160.5, 166.1; HRMS (ES+) Calcd for $[C_{30}H_{28}F_5N_3O_6S+H]$ 653.1619 found 654.1691; HPLC (I) $t_R$=23.256 min (92.9%), (II) $t_R$=42.389 min (90.7%).

EXAMPLE 56

Compound 29

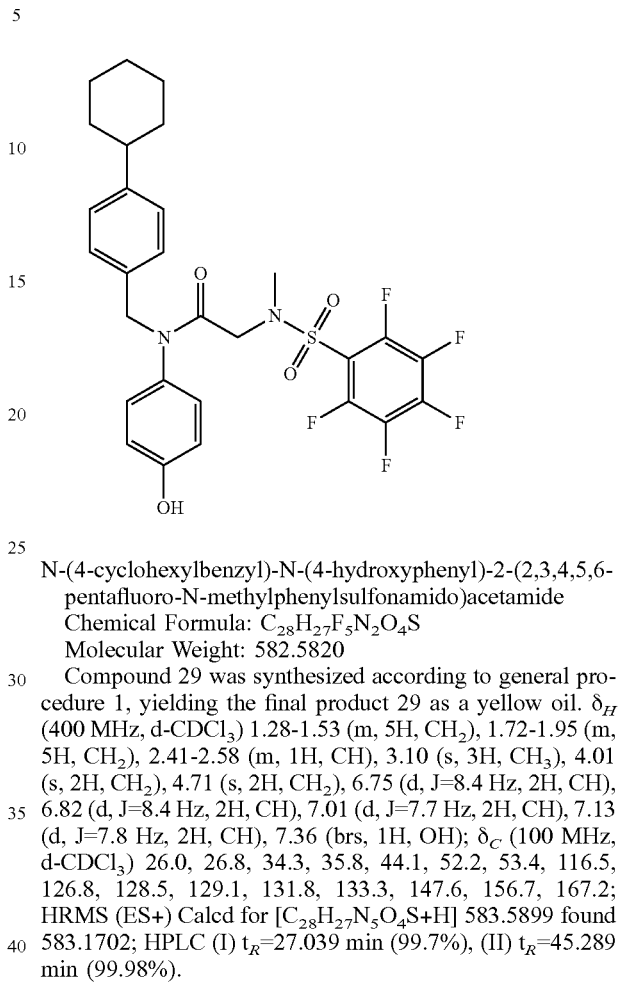

N-(4-cyclohexylbenzyl)-N-(4-hydroxyphenyl)-2-(2,3,4,5,6-pentafluoro-N-methylphenylsulfonamido)acetamide Chemical Formula: $C_{28}H_{27}F_5N_2O_4S$ Molecular Weight: 582.5820

Compound 29 was synthesized according to general procedure 1, yielding the final product 29 as a yellow oil. $\delta_H$ (400 MHz, d-$CDCl_3$) 1.28-1.53 (m, 5H, $CH_2$), 1.72-1.95 (m, 5H, $CH_2$), 2.41-2.58 (m, 1H, CH), 3.10 (s, 3H, $CH_3$), 4.01 (s, 2H, $CH_2$), 4.71 (s, 2H, $CH_2$), 6.75 (d, J=8.4 Hz, 2H, CH), 6.82 (d, J=8.4 Hz, 2H, CH), 7.01 (d, J=7.7 Hz, 2H, CH), 7.13 (d, J=7.8 Hz, 2H, CH), 7.36 (brs, 1H, OH); $\delta_C$ (100 MHz, d-$CDCl_3$) 26.0, 26.8, 34.3, 35.8, 44.1, 52.2, 53.4, 116.5, 126.8, 128.5, 129.1, 131.8, 133.3, 147.6, 156.7, 167.2; HRMS (ES+) Calcd for $[C_{28}H_{27}N_5O_4S+H]$ 583.5899 found 583.1702; HPLC (I) $t_R$=27.039 min (99.7%), (II) $t_R$=45.289 min (99.98%).

EXAMPLE 57

Compound 30

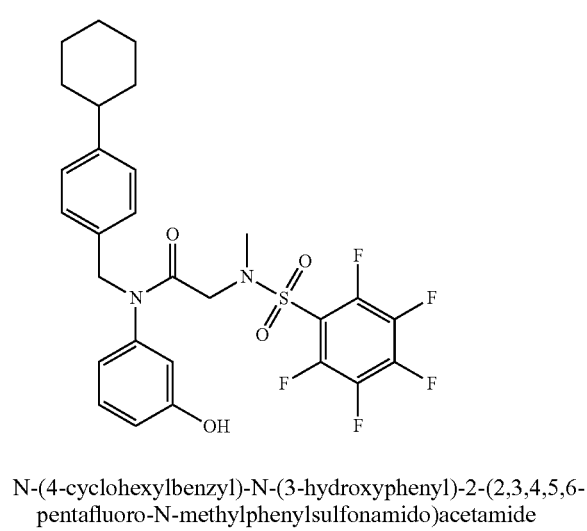

N-(4-cyclohexylbenzyl)-N-(3-hydroxyphenyl)-2-(2,3,4,5,6-pentafluoro-N-methylphenylsulfonamido)acetamide Chemical Formula: $C_{28}H_{27}F_5N_2O_4S$ Molecular Weight: 582.5820

Compound 30 was synthesized according to general procedure 1, yielding the final product 30 as a white solid (77%). $\delta_H$ (400 MHz, d-CDCl$_3$) 1.28-1.45 (m, 5H, CH$_2$), 1.70-1.93 (m, 5H, CH$_2$), 2.41-2.53 (m, 1H, CH), 3.08 (s, 3H, CH$_3$), 4.02 (s, 2H, CH$_2$), 4.70 (s, 2H, CH$_2$), 6.39 (brs, 1H, OH), 6.51 (d, J=7.4 Hz, 2H, CH), 6.79 (d, J=8.1 Hz, 1H, CH), 7.01 (d, J=7.7 Hz, 2H, CH), 7.10 (d, J=7.7 Hz, 2H, CH), 7.13-7.21 (m, 1H, CH); $\delta_C$ (100 MHz, d-CDCl$_3$) 26.1, 26.8, 34.4, 35.9, 44.2, 52.2, 53.2, 115.1, 116.0, 119.9, 126.9, 128.5, 130.9, 133.5, 141.2, 147.7, 157.3, 166.5; HRMS (ES+) Calcd for [C$_{28}$H$_{37}$F$_5$N$_2$O$_4$S+H] 538.5899 found 583.1703; HPLC (I) t$_R$=26.890 min (98.1%), (II) t$_R$=45.172 min (100.0%).

EXAMPLE 58

Compound 31

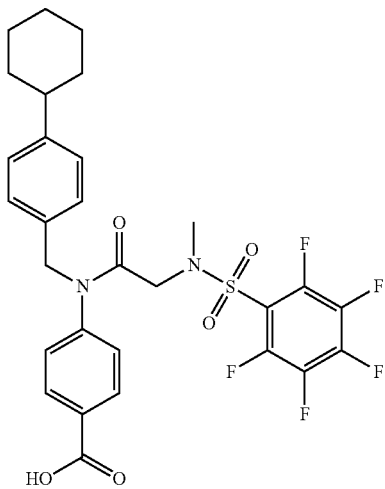 [SMILES: CN(CC(=O)N(Cc1ccc(C2CCCCC2)cc1)c1ccc(C(=O)O)cc1)S(=O)(=O)c1c(F)c(F)c(F)c(F)c1F]

4-(N-(4-cyclohexylbenzyl)-2-(2,3,4,5,6-pentafluoro-N-methylphenylsulfonamido)acetamido)benzoic acid Chemical Formula: $C_{29}H_{27}F_5N_2O_5S$ Molecular Weight: 610.5921

Compound 31 was synthesized according to general procedure 1, yielding the final product 31 as a yellow oil. $\delta_H$ (400 MHz, d-CDCl$_3$) 1.30-1.46 (m, 5H, CH$_2$), 1.71-1.88 (m, 5H, CH$_2$), 2.42-2.52 (m, 1H, CH), 3.10 (s, 3H, CH$_3$), 3.97 (s, 2H, CH$_2$), 4.76 (s, 2H, CH$_2$), 6.97 (d, J=7.7 Hz, 2H, CH), 7.06-7.15 (d, 4H, CH), 8.11 (d, J=8.4 Hz, 2H, CH); $\delta_C$ (100 MHz, d-CDCl$_3$) 26.0, 26.8, 34.3, 35.9, 44.1, 52.3, 53.2, 127.1, 128.4, 128.5, 129.9, 131.9, 132.9, 147.9, 166.0, 170.6, 177.6; HRMS (ES+) Calcd for [C$_{29}$H$_{27}$F$_5$N$_2$O$_5$S+H] 611.6000 found 611.1642; HPLC (I) t$_R$=26.244 min (100.0%), (II) t$_R$=44.532 min (100.0%).

EXAMPLE 59

Compound 32

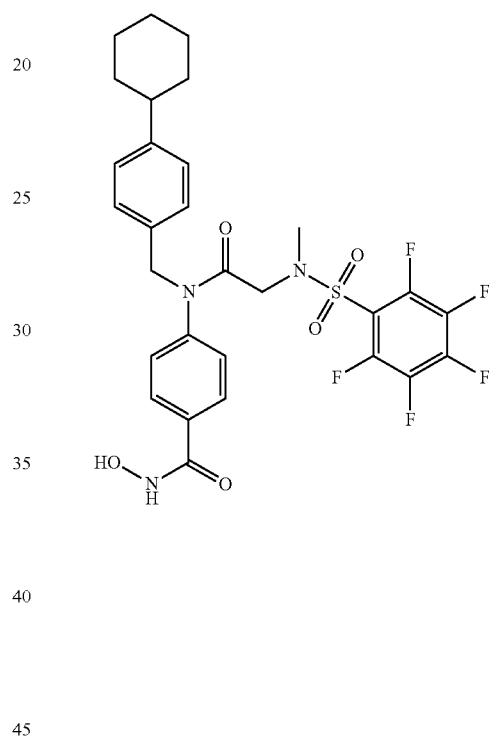

4-(N-(4-cyclohexylbenzyl)-2-(2,3,4,5,6-pentafluoro-N-methylphenylsulfonamido)acetamido)-N-hydroxybenzamide Chemical Formula: $C_{29}H_{28}F_5N_3O_5S$ Molecular Weight: 625.61

Compound 32 was synthesized according to general procedure 1, yielding the final product 32 as an orange solid. $\delta_H$ (400 MHz, d-MeOD) 1.27-1.43 (m, 5H, CH$_2$), 1.71-1.87 (m, 5H, CH$_2$), 2.41-2.51 (m, 1H, CH), 3.10 (s, 3H, CH$_3$), 4.01 (s, 2H, CH$_2$), 4.78 (s, 2H, CH$_2$), 6.98-7.01 (m, 2H, CH), 7.10 (d, J=7.2 Hz, 2H, CH), 7.15-7.23 (m, 2H, CH), 7.72-7.81 (m, 2H, CH); $\delta_C$ (100 MHz, d-MeOD) 25.7, 26.4, 34.12, 34.8, 44.1, 51.4, 52.4, 126.5, 128.1, 128.3, 133.5, 136.7, 136.8, 147.7, 154.2, 165.4, 166.6; HRMS (ES+) Calcd for [C$_{29}$H$_{28}$F$_5$N$_3$O$_5$S+H] 626.6147 found 626.1742; HPLC (I) t$_R$=22.843 min (97.9%), (II) t$_R$=44.120 min (97.2%).

EXAMPLE 60

Compound 33

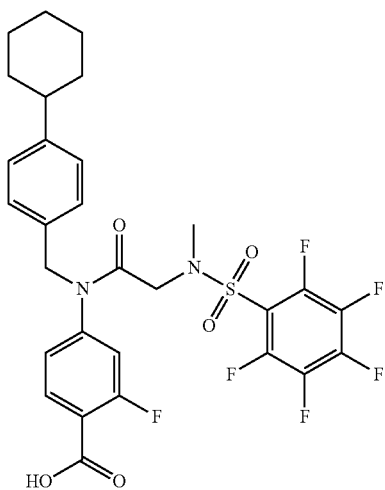 [SMILES: CN(CC(=O)N(Cc1ccc(C2CCCCC2)cc1)c1ccc(C(=O)O)c(F)c1)S(=O)(=O)c1c(F)c(F)c(F)c(F)c1F]

4-(N-(4-cyclohexylbenzyl)-2-(2,3,4,5,6-pentafluoro-N-methylphenylsulfonamido)acetamido)-2-fluorobenzoic acid Chemical Formula: $C_{29}H_{26}F_6N_2O_5S$ Molecular Weight: 628.58

Compound 33 was synthesized according to general procedure 1, yielding the final product 33 as a white solid. $\delta_H$ (400 MHz, d-CDCl$_3$) 1.26-1.48 (m, 5H, CH$_2$), 1.70-1.91 (m, 5H, CH$_2$), 2.41-2.54 (m, 1H, CH), 3.10 (s, 3H, CH$_3$), 4.03 (s, 2H, CH$_2$), 4.77 (s, 2H, CH$_2$), 6.84-6.96 (m, 2H, CH), 6.99 (d, J=7.7 Hz, 2H, CH), 7.13 (d, J=7.7 Hz, 2H, CH), 8.03 (t, J=7.9 Hz, 1H, CH), 9.42 (brs, 1H, OH); $\delta_C$ (100 MHz, d-CDCl$_3$) 26.0, 26.8, 34.3, 35.9, 44.2, 52.3, 53.2, 127.3, 128.3, 132.7, 134.2, 148.2, 161.4, 164.0, 165.9, 167.8, 177.5; HRMS (ES+) Calcd for [$C_{29}H_{26}F_5N_2O_5S$+H] 629.5905 found 629.629.1545; HPLC (I) $t_R$=25.136 min (97.8%), (II) $t_R$=43.841 min (97.8%).

EXAMPLE 61

Compound 34

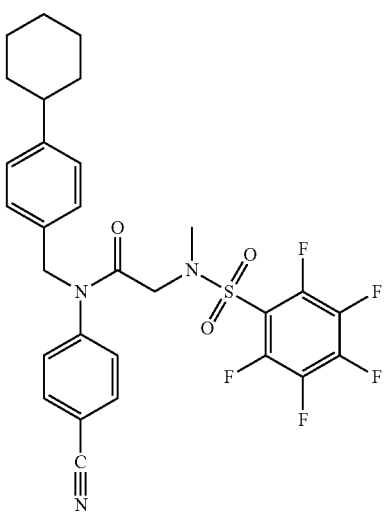 [SMILES: CN(CC(=O)N(Cc1ccc(C2CCCCC2)cc1)c1ccc(C#N)cc1)S(=O)(=O)c1c(F)c(F)c(F)c(F)c1F]

N-(4-cyanophenyl)-N-(4-cyclohexylbenzyl)-2-(2,3,4,5,6-pentafluoro-N-methylphenylsulfonamido)acetamide Chemical Formula: $C_{29}H_{26}F_5N_3O_3S$ Molecular Weight: 591.5921

Compound 34 was synthesized according to general procedure h, yielding the final product 34 as a white solid (84%). $\delta_H$ (400 MHz, d-CDCl$_3$) 1.28-1.45 (m, 5H, CH$_2$), 1.69-1.89 (m, 5H, CH$_2$), 2.40-2.53 (m, 1H, CH), 3.10 (s, 3H, CH$_3$), 3.93 (s, 2H, CH$_2$), 4.76 (s, 2H, CH$_2$), 6.97 (d, J=7.4 Hz, 2H, CH), 7.10-7.18 (m, 4H, CH), 7.65 (d, J=7.7 Hz, 2H, CH); $\delta_C$ (100 MHz, d-CDCl$_3$) 26.0, 26.7, 34.3, 35.7, 44.0, 52.0, 52.9, 61.8, 112.2, 117.6, 127.1, 128.3, 129.1, 132.9, 133.7, 147.9, 165.8; HRMS (ES+) Calcd for [$C_{29}H_{26}F_5N_3O_3S$+H] 592.6000 found 592.1707; HPLC (I) $t_R$=29.752 min (100.0%), (II) $t_R$=47.312 min (99.78%).

EXAMPLE 62

Compound 35

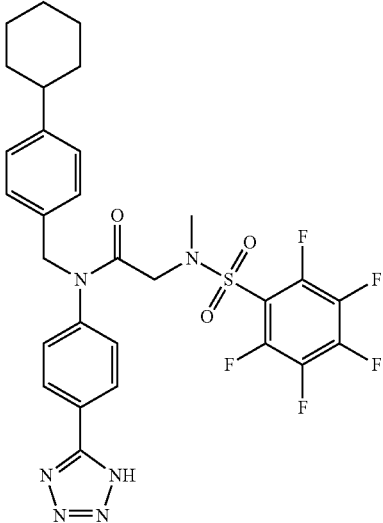 [SMILES: CN(CC(=O)N(Cc1ccc(C2CCCCC2)cc1)c1ccc(-c2nnn[nH]2)cc1)S(=O)(=O)c1c(F)c(F)c(F)c(F)c1F]

N-(4-(1H-tetrazol-5-yl)phenyl)-N-(4-cyclohexylbenzyl)-2-(2,3,4,5,6-pentafluoro-N-methylphenylsulfonamido)acetamide Chemical Formula: $C_{29}H_{27}F_5N_6O_3S$ Molecular Weight: 634.6201

Compound 35 was synthesized according to general procedure h, yielding the final product 35 as a white powder (82%). $\delta_H$ (400 MHz, d-CDCl$_3$) 1.25-1.41 (m, 5H, CH$_2$), 1.64-1.84 (m, 5H, CH$_2$), 2.38-2.51 (m, 1H, CH), 3.10 (s, 3H, CH$_3$), 3.96 (s, 2H, CH$_2$), 4.75 (s, 2H, CH$_2$), 6.97 (d, J=7.4 Hz, 2H, CH), 7.05-7.18 (m, 4H, CH), 8.03-8.10 (m, 2H, CH); $\delta_C$ (100 MHz, d-CDCl$_3$) 26.1, 26.7, 34.3, 35.9, 44.1, 52.3, 53.4, 115.4, 127.1, 128.5, 129.1, 132.9, 142.3, 147.9, 157.1, 166.6; HRMS (ES+) Calcd for [C$_{29}$H$_{27}$N$_6$O$_3$S+H] 635.6280 found 635.1858; HPLC (I) t$_R$=24.461 min (99.7%), (II) t$_R$=43.295 min (99.3%).

EXAMPLE 63

Compound 36

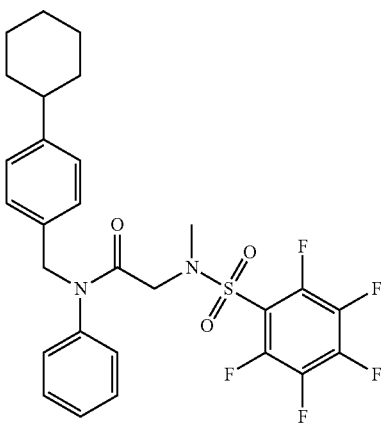 [SMILES: CN(CC(=O)N(Cc1ccc(C2CCCCC2)cc1)c1ccccc1)S(=O)(=O)c1c(F)c(F)c(F)c(F)c1F]

N-(4-cyclohexylbenzyl)-2-(2,3,4,5,6-pentafluoro-N-methylphenylsulfonamido)-N-phenylacetamide Chemical Formula: $C_{28}H_{27}F_5N_2O_3S$ Molecular Weight: 566.5826

Compound 36 was synthesized according to general procedure h, yielding the final product 36 as a while solid. ($\delta_H$ (400 MHz, d-CDCl$_3$) 1.28-1.45 (m, 5H, CH$_2$), 1.71-1.93 (m, 5H, CH$_2$), 2.42-2.53 (m, 1H, CH), 3.10 (s, 3H, CH$_3$), 3.95 (s, 2H, CH$_2$), 4.72 (s, 2H, CH$_2$), 6.96-7.03 (m, 4H, CH), 7.11 (d, J=7.9 Hz, 2H, CH), 7.34-7.41 (m, 3H, CH); $\delta_C$ (100 MHz, d-CDCl$_3$) 26.1, 26.8, 34.4, 35.8, 44.2, 52.3, 53.2, 126.9, 128.2, 128.5, 128.8, 130.1, 133.6, 140.2, 147.6, 166.2; HRMS (ES+) Calcd for [C$_{28}$H$_{27}$F$_5$N$_2$O$_3$S+H] 567.5905 found 567.1752; HPLC (I) t$_R$=22.657 min (99.6%), (II) t$_R$=49.267 min (98.9%).

EXAMPLE 64

Compound 37

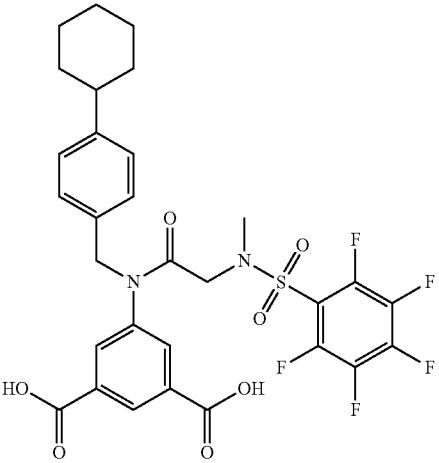 [SMILES: CN(CC(=O)N(Cc1ccc(C2CCCCC2)cc1)c1cc(C(=O)O)cc(C(=O)O)c1)S(=O)(=O)c1c(F)c(F)c(F)c(F)c1F]

5-(N-(4-cyclohexylbenzyl)-2-(2,3,4,5,6-pentafluoro-N-methylphenylsulfonamido)acetamido)isophthalic acid Chemical Formula: $C_{30}H_{27}F_5N_2O_7S$ Molecular Weight: 654.6016

Compound 37 was synthesized according to general procedure 1, yielding the final product 37 as a white solid. $\delta_H$ (400 MHz, d-(CD$_3$)$_2$SO) 1.21-1.42 (m, 5H, CH$_2$), 1.64-1.79 (m, 5H, CH$_2$), 2.40-2.51 (m, 1H, CH), 3.01 (s, 3H, CH$_3$), 3.97 (s, 2H, CH$_2$), 4.77 (s, 2H, CH$_2$), 7.01 (d, J=7.4 Hz, 2H, CH), 7.12 (d, J=7.4 Hz, 2H, CH), 7.84-7.89 (m, 2H, CH), 8.41 (s, 1H, CH); $\delta_C$ (100 MHz, d-(CD$_3$)$_2$SO) 25.8, 26.8, 34.2, 35.8, 43.7, 52.5, 53.1, 127.2, 128.5, 130.1, 133.3, 133.5, 134.1, 140.4, 141.1, 147.1, 166.1, 166.4; HRMS (ES+) Calcd for [C$_{30}$H$_{27}$F$_5$N$_2$O$_7$S+H] 655.6095 found 655.1537; HPLC (I) t$_R$=18.18 min (93.4%), (II) t$_R$=35.28 min (94.5%).

EXAMPLE 65

Compound 38

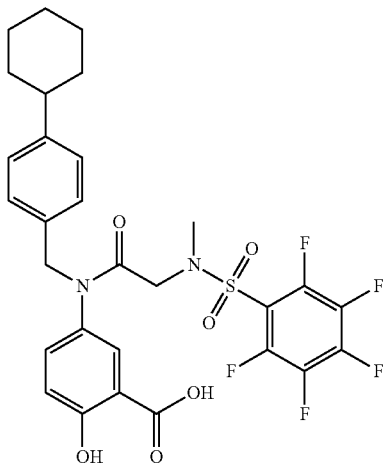 [SMILES: CN(CC(=O)N(Cc1ccc(C2CCCCC2)cc1)c1ccc(O)c(C(=O)O)c1)S(=O)(=O)c1c(F)c(F)c(F)c(F)c1F]

5-(N-(4-cyclohexylbenzyl)-2-(2,3,4,5,6-pentafluoro-N-methylphenylsulfonamido)acetamido)-2-hydroxybenzoic acid Chemical Formula: $C_{29}H_{27}F_5N_2O_6S$ Molecular Weight: 626.5915

Compound 38 was synthesized according to general procedure 1, yielding the final product 38 as a colorless oil. $\delta_H$ (400 MHz, d-$(CD_3)_2SO$) 1.26-1.44 (m, 5H, $CH_2$), 1.71-1.87 (m, 5H, $CH_2$), 2.42-2.50 (m, 1H, CH), 3.10 (s, 3H, $CH_3$), 3.94 (s, 2H, $CH_2$), 4.68 (s, 2H, $CH_2$), 7.01 (d, J=7.4 Hz, 2H, CH), 7.12 (d, J=7.4 Hz, 2H, CH), 7.84-7.89 (m, 2H, CH), 8.41 (s, 1H, CH), 10.94 (brs, 1H, OH); $\delta_C$ (100 MHz, d-$CDCl_3$) 25.8, 26.8, 34.2, 35.8, 43.7, 52.5, 53.1, 127.2, 128.5, 130.1, 133.3, 133.5, 134.1, 140.4, 141.1, 147.1, 166.1, 166.4; HRMS (ES+) Calcd for $[C_{29}H_{27}F_5N_2O_6S+H]$ 627.5994 found 627.1588; HPLC (I) $t_R$=26.235 min (99.4%), (II) $t_R$=44.654 min (96.4%).

EXAMPLE 66

Compound 39

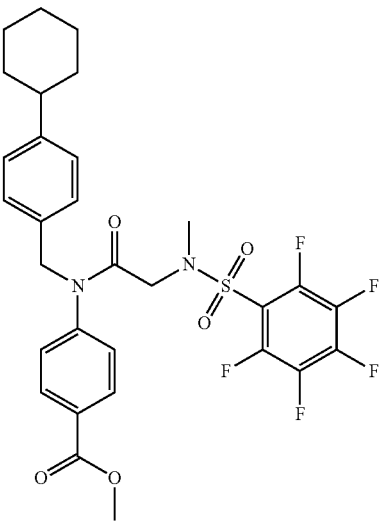 [SMILES: COC(=O)c1ccc(N(Cc2ccc(C3CCCCC3)cc2)C(=O)CN(C)S(=O)(=O)c2c(F)c(F)c(F)c(F)c2F)cc1]

methyl 4-(N-(4-cyclohexylbenzyl)-2-(2,3,4,5,6-pentafluoro-N-methylphenylsulfonamido)acetamido)benzoate Chemical Formula: $C_{30}H_{29}F_5N_2O_5S$ Molecular Weight: 624.6187

Compound 39 was synthesized according to general procedure h, yielding the final product 39 as a white solid (74%). $\delta_H$ (400 MHz, d-$CDCl_3$) 1.26-1.49 (m, 5H, $CH_2$), 1.66-1.93 (m, 5H, $CH_2$), 2.37-2.54 (m, 1H, CH), 3.07 (s, 3H, $CH_3$), 3.90 (s, 3H, $CH_3$), 3.94 (s, 2H, $CH_2$), 4.73 (s, 2H, $CH_2$), 6.95 (d, J=7.4 Hz, 2H, CH), 7.01-7.14 (m, 4H, CH), 8.02 (d, J=8.3 Hz, 2H, CH); $\delta_C$ (100 MHz, d-$CDCl_3$) 25.1, 26.7, 34.2, 35.8, 44.0, 48.5, 51.8, 53.5, 126.8, 128.1, 128.4, 131.2, 133.2, 147.6, 152.4, 165.1, 166.3, 165.8; HRMS (ES+) Calcd for $[C_{30}H_{29}F_5N_2O_5S+H]$ 625.6266 found 625.1784; HPLC (I) $t_R$=32.188 min (99.6%), (II) $t_R$=49.208 min (99.6%).

EXAMPLE 67

Compound 40

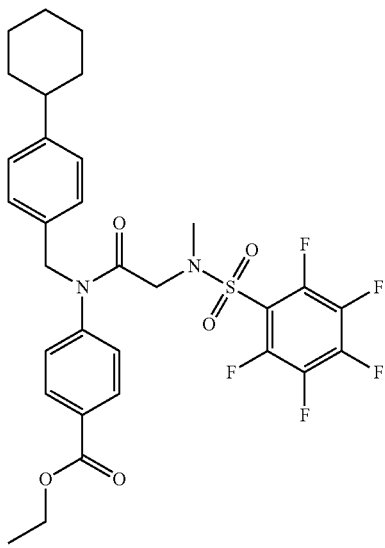 [SMILES: CCOC(=O)c1ccc(N(Cc2ccc(C3CCCCC3)cc2)C(=O)CN(C)S(=O)(=O)c2c(F)c(F)c(F)c(F)c2F)cc1]

ethyl 4-(N-(4-cyclohexylbenzyl)-2-(2,3,4,5,6-pentafluoro-N-methylphenylsulfonamido)acetamido)benzoate Chemical Formula: $C_{31}H_{31}F_5N_2O_5S$ Molecular Weight: 638.6453

Compound 40 was synthesized according to general procedure h, yielding the final product 40 as a yellow oil. $\delta_H$ (400 MHz, d-CDCl$_3$) 1.32-1.46 (m, 8H, CH$_2$ and CH$_3$), 1.70-1.86 (m, 5H, CH$_2$), 2.42-2.52 (m, 1H, CH), 3.10 (s, 3H, CH$_3$), 3.94 (s, 2H, CH$_2$), 4.39 (q, J=7.2 Hz, 2H, CH$_2$), 4.73 (s, 2H, CH$_2$), 6.96 (d, J=7.9 Hz, 2H, CH), 7.1 (d, J=8.3 Hz, 2H, CH), 7.10 (d, J=7.9 Hz, 2H, CH), 8.10 (d, J=8.3 Hz, 2H, CH); $\delta_C$ (100 MHz, d-CDCl$_3$) 14.1, 26.0, 26.7, 34.2, 35.8, 44.0, 52.2, 53.0, 61.3, 126.9, 128.2, 128.4, 131.3, 133.1, 147.8, 152.6, 165.3, 165.7, 165.8; HRMS (ES+) Calcd for [C$_{31}$H$_{31}$F$_5$N$_2$O$_5$S+H] 639.6532 found 639.1956; HPLC (I) t$_R$=33.512 min (100.0%), (II) t$_R$=50.144 min (100.0%).

EXAMPLE 68

Compound 41

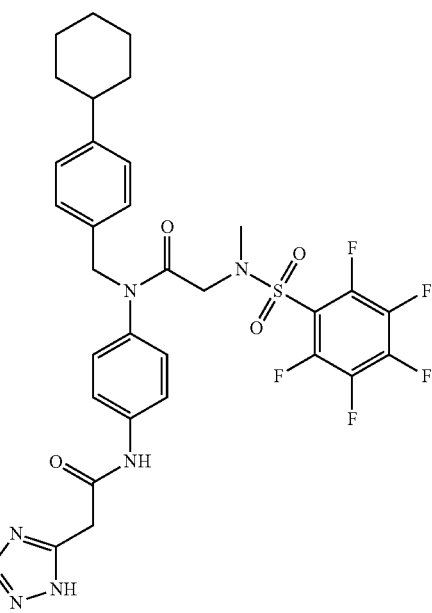

N-(4-(2-(1H-tetrazol-5-yl)acetamido)phenyl)-N-(4-cyclohexylbenzyl)-2-(2,3,4,5,6-pentafluoro-N-methylphenylsulfonamido)acetamide Chemical Formula: $C_{31}H_{30}F_5N_7O_4S$ Molecular Weight: 691.6714

Compound 41 was synthesized according to general procedure h, yielding the final product 41 as a yellow oil. $\delta_H$ (400 MHz, d-(CD$_3$)$_2$SO) 1.22-1.44 (m, 5H, CH$_2$), 1.64-1.82 (m, 5H, CH$_2$), 2.41-2.50 (m, 1H, CH), 3.01 (s, 3H, CH$_3$), 3.98 (s, 2H, CH$_2$), 4.10 (s, 2H, CH$_2$), 4.69 (s, 2H, CH$_2$), 7.00 (d, J=7.9 Hz, 2H, CH), 7.05-7.18 (m, 4H, CH), 7.60 (d, J=8.6 Hz, 2H, CH); $\delta_C$ (100 MHz, d-CDCl$_3$) 20.7, 26.7, 31.6, 34.2, 36.7, 44.1, 52.1, 53.1, 97.8, 121.4, 126.9, 128.4, 128.7, 133.3, 137.8, 147.6, 163.1, 166.2, 176.9; HRMS (ES+) Calcd for [C$_{31}$H$_{30}$F$_5$N$_7$O$_4$S+H] 692.6794 found 692.2072; HPLC (I) t$_R$=21.636 min (97.6%), (II) t$_R$=9.452 min (99.12%).

EXAMPLE 69

Compound 42

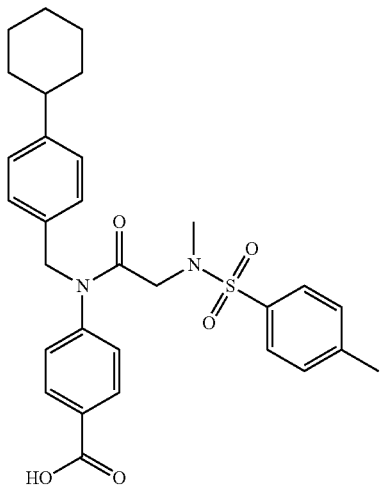 [SMILES: Cc1ccc(S(=O)(=O)N(C)CC(=O)N(Cc2ccc(C3CCCCC3)cc2)c2ccc(C(=O)O)cc2)cc1]

4-(N-(4-cyclohexylbenzyl)-2-(N,4-dimethylphenylsulfonamido)acetamido)benzoic acid Chemical Formula: $C_{30}H_{34}N_2O_5S$ Molecular Weight: 534.6664

Compound 42 was synthesized according to general procedure 1, yielding the final product 43 as a white solid. $\delta_H$ (400 MHz, d-(CDCl$_3$) 1.25-1.41 (m, 5H, CH$_2$), 1.71-1.89 (m, 5H, CH$_2$), 2.41 (s, 3H, CH$_3$), 2.44-2.51 (m, 1H, CH), 2.86 (s, 3H, CH$_3$), 3.77 (s, 2H, CH$_2$), 4.83 (s, 2H, CH$_2$), 7.04 (d, J=7.4 Hz, 2H, CH), 7.10-7.16 (m, 4H, CH), 7.27 (d, J=8.1 Hz, 2H, CH), 7.63 (d, J=8.2 Hz, 2H, CH), 8.10 (d, J=8.2 Hz, 2H, CH); $\delta_C$ (100 MHz, d-CDCl$_3$) 21.4, 25.9, 26.8, 29.5, 34.3, 35.8, 44.1, 53.1, 126.8, 127.4, 129.3, 129.6, 131.6, 133.5, 135.2, 137.5, 143.3, 145.1, 146.5, 147.1, 166.7, 169.4; HRMS (ES+) Calcd for [C$_{30}$H$_{34}$N$_2$O$_5$S+H] 535.6743 found 535.2259; HPLC (I) t$_R$=20.701 min (100.0%), (II) t$_R$=40.495 min (100.0%).

EXAMPLE 70

Compound 43

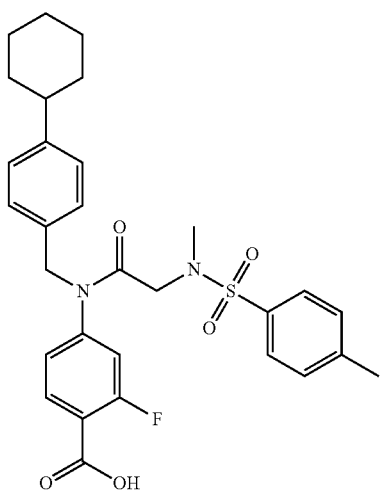 [SMILES: Cc1ccc(S(=O)(=O)N(C)CC(=O)N(Cc2ccc(C3CCCCC3)cc2)c2ccc(C(=O)O)c(F)c2)cc1]

4-(N-(4-cyclohexylbenzyl)-2-(N,4-dimethylphenylsulfonamido)acetamido)-2-fluorobenzoic acid Chemical Formula: $C_{30}H_{33}FN_2O_5S$ Molecular Weight: 552.6568

Compound 43 was synthesized according to general procedure 1, yielding the final product 44 as a yellow oil. $\delta_H$ (400 MHz, d-(CDCl$_3$) 1.26-1.44 (m, 5H, CH$_2$), 1.70-1.89 (m, 5H, CH$_2$), 2.41 (s, 3H, CH$_3$), 2.42-2.54 (m, 1H, CH), 2.85 (s, 3H, CH$_3$), 3.81 (s, 2H, CH$_2$), 4.84 (s, 2H, CH$_2$), 6.85-6.98 (m, 2H, CH), 7.05 (d, J=7.7 Hz, 2H, CH), 7.12 (d, J=7.7 Hz, 2H, CH), 7.3 (d, J=8.1 Hz, 2H, CH), 7.63 (d, J=7.9 Hz, 2H, CH), 7.96-8.03 (m, 1H, CH); $\delta_C$ (100 MHz, d-CDCl$_3$) 21.4, 25.8, 26.7, 34.3, 35.7, 44.1, 51.8, 53.1, 127.1, 127.5, 129.5, 132.7, 133.1, 134.2, 134.9, 136.8, 137.1, 148.2, 161.4, 164.0, 165.9, 167.8. HRMS (ES+) Calcd for [C$_{30}$H$_{33}$FN$_2$O$_5$S+H] 553.6648 found 553.2158; HPLC (I) t$_R$=20.972 min (97.1%), (II) t$_R$=40.669 min (94.40%).

EXAMPLE 71

Compound 44

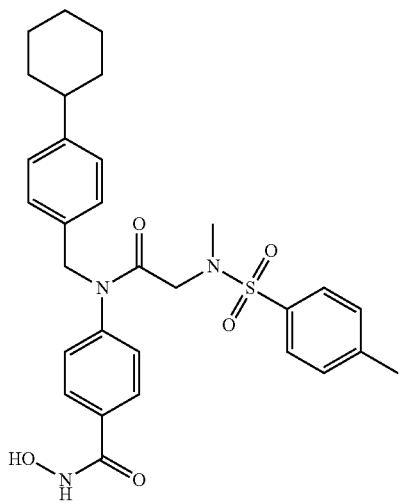 [SMILES: Cc1ccc(S(=O)(=O)N(C)CC(=O)N(Cc2ccc(C3CCCCC3)cc2)c2ccc(C(=O)NO)cc2)cc1]

4-(N-(4-cyclohexylbenzyl)-2-(N,4-dimethylphenylsulfonamido)acetamido)-N-hydroxybenzamide Chemical Formula: $C_{30}H_{35}N_3O_5S$ Molecular Weight: 549.68

Compound 44 was synthesized according to general procedure 1, yielding the final product 45 as a yellow oil. $\delta_H$ (400 MHz, d-CDCl$_3$) 1.26-1.46 (m, 5H, CH$_2$), 1.70-1.87 (m, 5H, CH$_2$), 2.39 (s, 3H, CH$_3$), 2.42-2.50 (m, 1H, CH), 2.81 (s, 3H, CH$_3$), 3.63 (s, 1H, NH), 3.70 (brs, 1H, OH), 3.89 (s, 2H, CH$_2$), 4.85 (s, 2H, CH$_2$), 7.03-7.14 (m, 4H, CH), 7.18-7.24 (m, 2H, CH), 7.31 (d, J=7.5 Hz, 2H, CH), 7.53 (d, J=7.5 Hz, 2H, CH), 7.75 (d, J=7.0 Hz, 2H, CH); $\delta_C$ (100 MHz, d-CDCl$_3$) 21.4, 25.9, 26.7, 29.6, 34.3, 35.8, 44.1, 51.4, 53.1, 119.8, 126.9, 127.4, 128.1, 129.2, 132.5, 134.3, 135.3, 143.2, 147.3, 163.1, 167.6; HRMS (ES+) Calcd for [C$_{30}$H$_{35}$N$_3$O$_5$S+H] 550.6889 found 550.2370; HPLC (I) $t_R$=14.977 min (96.5%), (II) $t_R$=37.687 min (97.2%).

EXAMPLE 72

Compound 45

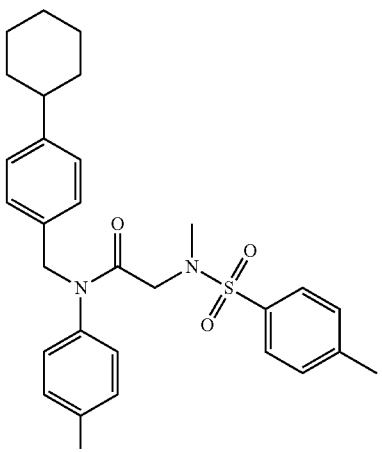

N-(4-cyclohexylbenzyl)-2-(N,4-dimethylphenylsulfonamido)-N-(4-hydroxyphenyl)acetamide Chemical Formula: $C_{29}H_{34}N_2O_4S$ Molecular Weight: 506.6563

Compound 45 was synthesized according to general procedure 1, yielding the final product 46 as a yellow oil. $\delta_H$ (400 MHz, d-CDCl$_3$) 1.28-1.44 (m, 5H, CH$_2$), 1.71-1.89 (m, 5H, CH$_2$), 2.39 (s, 3H, CH$_3$), 2.42-2.50 (m, 1H, CH), 2.86 (s, 3H, CH$_3$), 3.74 (s, 2H, CH$_2$), 4.73 (s, 2H, CH$_2$), 6.36 (brs, 1H, OH), 6.76-6.83 (m, 4H, CH), 7.04 (d, J=8.1 Hz, 2H, CH), 7.1 (d, J=7.9 Hz, 2H, CH), 7.25 (d, J=7.4 Hz, 2H, CH), 7.64 (d, J=8.1 Hz, 2H, CH); $\delta_C$ (100 MHz, d-CDCl$_3$) 21.4, 25.8, 26.5, 34.3, 35.8, 44.1, 51.4, 53.1, 116.3, 126.6, 127.4, 128.7, 129.3, 132.7, 134.0, 135.3, 143.2, 147.3, 156.1, 167.6; HRMS (ES+) Calcd for [C$_{29}$H$_{34}$N$_2$O$_4$S+H] 507.6642 found 507.2312; HPLC (I) $t_R$=21.567 min (100.0%), (II) $t_R$=41.184 min (100.0%).

EXAMPLE 73

Compound 46

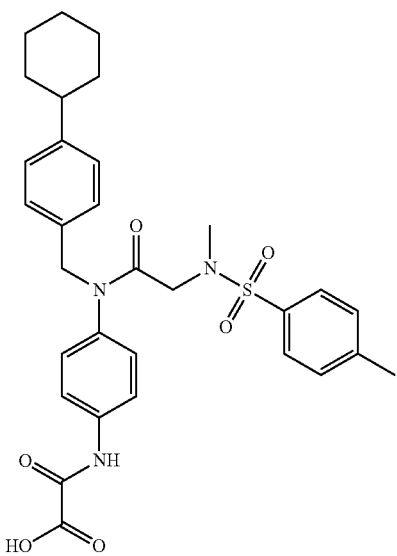 [SMILES: Cc1ccc(S(=O)(=O)N(C)CC(=O)N(Cc2ccc(C3CCCCC3)cc2)c2ccc(NC(=O)C(=O)O)cc2)cc1]

2-((4-(N-(4-cyclohexylbenzyl)-2-(N,4-dimethylphenylsulfonamido)acetamido)phenyl)amino)-2-oxoacetic acid Chemical Formula: $C_{31}H_{35}N_3O_6S$ Molecular Weight: 577.6911

Compound 46 was synthesized according to general procedure g, yielding the final product 47 as a white solid. $\delta_H$ (400 MHz, d-CDCl$_3$) 1.24-1.41 (m, 5H, CH$_2$), 1.71-1.86 (m, 5H, CH$_2$), 2.45 (s, 3H, CH$_3$), 2.41-2.53 (m, 1H, CH), 2.87 (s, 3H, CH$_3$), 3.71 (s, 2H, CH$_2$), 4.77 (s, 2H, CH$_2$), 6.98-7.01 (m, 4H, CH), 7.12 (d, J=7.8 Hz, 2H, CH), 7.31 (d, J=7.3 Hz, 2H, CH), 7.53-7.59 (m, 4H, CH); $\delta_C$ (100 MHz, d-CDCl$_3$) 25.9, 26.2, 34.1, 35.3, 44.2, 51.6, 53.4, 63.6, 121.1, 126.5, 128.2, 129.1, 129.7, 133.1, 135.5, 136.8, 137.4, 143.1, 147.2, 154.4, 161.2, 165.9, 167.1; HRMS (ES+) Calcd for [$C_{31}H_{35}N_3O_6S$+H] 578.6990 found 578.2319; HPLC (I) $t_R$=19.967 min (100.0%), (II) $t_R$=39.811 min (97.9%).

EXAMPLE 74

Compound 47

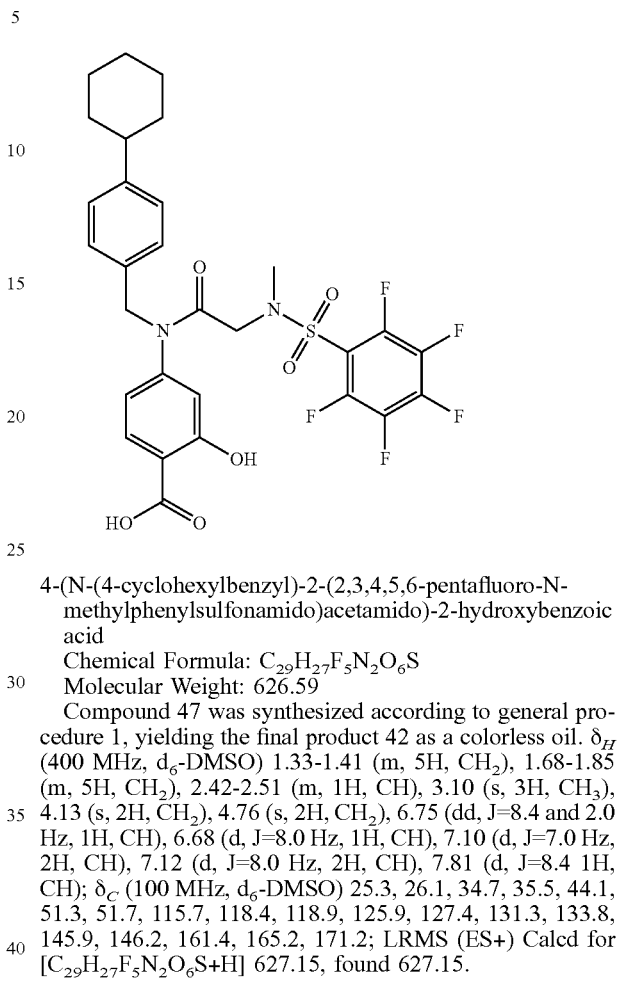

4-(N-(4-cyclohexylbenzyl)-2-(2,3,4,5,6-pentafluoro-N-methylphenylsulfonamido)acetamido)-2-hydroxybenzoic acid Chemical Formula: $C_{29}H_{27}F_5N_2O_6S$ Molecular Weight: 626.59

Compound 47 was synthesized according to general procedure 1, yielding the final product 42 as a colorless oil. $\delta_H$ (400 MHz, d$_6$-DMSO) 1.33-1.41 (m, 5H, CH$_2$), 1.68-1.85 (m, 5H, CH$_2$), 2.42-2.51 (m, 1H, CH), 3.10 (s, 3H, CH$_3$), 4.13 (s, 2H, CH$_2$), 4.76 (s, 2H, CH$_2$), 6.75 (dd, J=8.4 and 2.0 Hz, 1H, CH), 6.68 (d, J=8.0 Hz, 1H, CH), 7.10 (d, J=7.0 Hz, 2H, CH), 7.12 (d, J=8.0 Hz, 2H, CH), 7.81 (d, J=8.4 1H, CH); $\delta_C$ (100 MHz, d$_6$-DMSO) 25.3, 26.1, 34.7, 35.5, 44.1, 51.3, 51.7, 115.7, 118.4, 118.9, 125.9, 127.4, 131.3, 133.8, 145.9, 146.2, 161.4, 165.2, 171.2; LRMS (ES+) Calcd for [$C_{29}H_{27}F_5N_2O_6S$+H] 627.15, found 627.15.

EXAMPLE 75

Compound 48

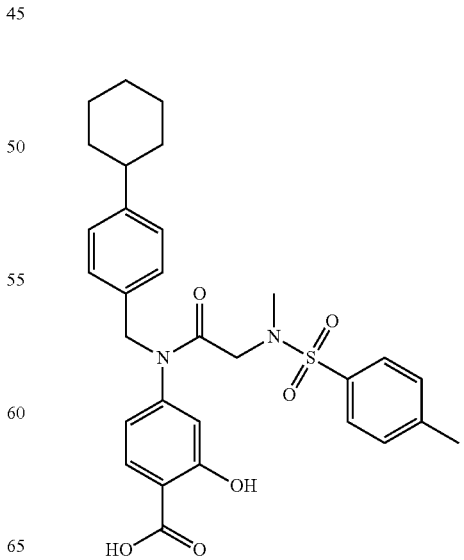

4-(N-(4-cyclohexylbenzyl)-2-(N,4-dimethylphenylsulfonamido)acetamido)-2-hydroxybenzoic acid Chemical Formula: $C_{30}H_2O_6S$ Molecular Weight: 550.67

Compound 48 was synthesized according to general procedure 1, yielding the final product 48 as a white solid. $\delta_H$ (400 MHz, d-CDCl$_3$) 1.26-1.45 (m, 5H, CH$_2$), 1.71-1.89 (m, 5H, CH$_2$), 2.42 (s, 3H, CH$_3$), 2.43-2.51 (m, 1H, CH), 2.88 (s, 3H, CH$_3$), 3.86 (s, 2H, CH$_2$), 4.81 (s, 2H, CH$_2$), 6.61 (d, J=8.3 Hz, 1H, CH), 6.68-6.72 (m, 1H, CH), 7.10 (d, J=8.1 Hz, 2H, CH), 7.12 (d, J=8.1 Hz, 2H, CH), 7.27 (d, J=8.4, 1H, CH), 7.66 (d, J=8.1 Hz, 2H, CH), 7.87 (d, J=8.1 Hz, 2H, CH); $\delta_C$ (100 MHz, d$_6$-CDCl$_3$) 21.3, 25.3, 26.5, 34.1, 36.2, 42.1, 43.4, 51.3, 52.0, 112.8, 116.3, 118.8, 126.8, 127.1, 127.6, 131.0, 134.3, 141.2, 146.7, 147.1, 161.8, 167.0, 171.5; LRMS (ES+) Calcd for [C$_{29}$H$_{27}$F$_5$N$_2$O$_6$S+H] 627.1582, found 627.1551; HRMS (ES+) Calcd for [C$_{30}$H$_{34}$N$_2$O$_6$S+H] 551.2223 found 551.2210; HPLC (I) $t_R$=24.351 min (98.1%), (II) $t_R$=52.80 min (98.2%).

EXAMPLE 76

Kinase and GPCR Screenings

Test compound was evaluated at a single dose of 5 μM in duplicate mode. Control compound was tested in a 10-dose IC$_{50}$ with 3-fold serial dilution starting at 20 μM. Reactions were carried out at 10 μM ATP.

Figure 5:
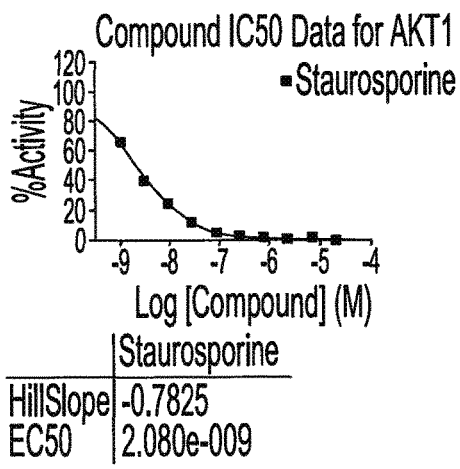
FIG. 5 illustrates the $IC_{50}$ determination of control (Staurosporine) against the selected kinases.
Figure 5:
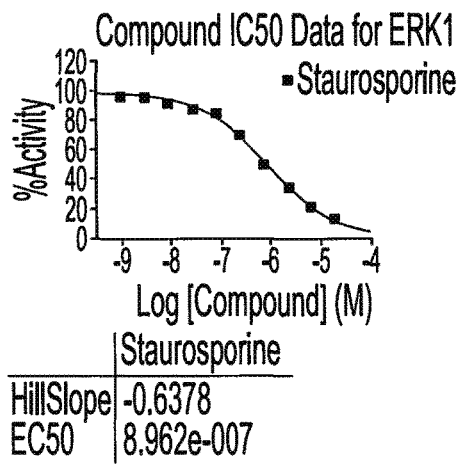
Figure 5:
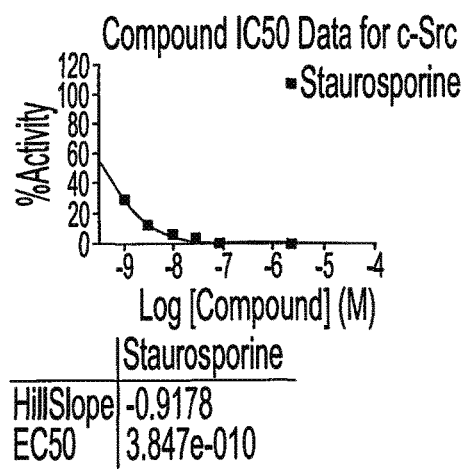
Figure 5:
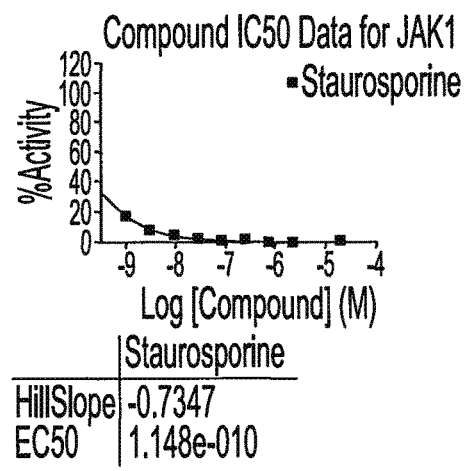
Figure 5:
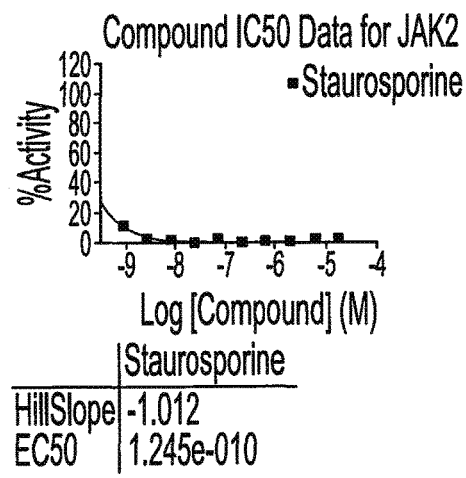

Preliminary screen against AKT, c-Src, ERK1, JaK1 and JaK2 was performed at Reaction Biology Corporation (www.reactionbiology.com, Malvern, Pa.) using the "HotSpot" assay platform. Specific kinase/substrate pairs along with their required cofactors were prepared in reaction buffer; 20 mM Hepes pH 7.5, 10 mM MgCl$_2$, 1 mM EGTA, 0.02% Brij35, 0.02 mg/ml BSA, 0.1 mM Na$_3$VO$_4$, 2 mM DTT, 1% DMSO. The screen was completed in duplicate at a single concentration of 5 μM. The reaction well with the subject compound was treated with a mixture of ATP (Sigma, St. Louis Mo.) and $^{33}$P ATP (Perkin Elmer, Waltham Mass.) to a final concentration of 10 μM. Control compound (Staurosporine) was tested in a 10-dose IC$_{50}$ with 3-fold serial dilution starting at 20 μM. Reaction wells were kept at room temperature for 120 minutes, followed by spotting each of the reactions onto P81 ion exchange filter paper (Whatman Inc., Piscataway, N.J.). Any unbound phosphate was removed through extensive washing of filters using 0.75% phosphoric acid. Background was subtracted using control reactions and the kinase activity data was expressed as the percent remaining kinase activity in test samples compared to vehicle (dimethyl sulfoxide) reactions. All IC$_{50}$ values (table 3) and curve fitting were produced using Prism (GraphPad Software) (FIG. 5).

Second screen against 101 selected kinases including ABL1(E255K)-phosphorylated, ABL1(T315I)-phosphorylated, ABL1-nonphosphorylated, ABL1-phosphorylated, ACVR1B, ADCK3, AKT1, AKT2, ALK, AURKA, AURKB, AXL, BMPR2, BRAF, BRAF(V600E), BTK, CDK11, CDK2, CDK3, CDK7, CDK9, CHEK1, CSF1R, CSNK1D, CSNK1G2, DCAMKL1, DYRK1B, EGFR, EGFR(L858R), EPHA2, ERBB2, ERBB4, ERK1, FAK, FER, FES, FGFR2, FGFR3, FGR, FLT3, FYN, GSK3B, IGF1R, IKK-alpha, IKK-beta, INSR, JAK2(JH1 domain-catalytic), JAK3 (JH1 domain-catalytic), JNK1, JNK2, JNK3, MAPKAPK2, MARK3, MEK1, MEK2, MET, MKNK1, MKNK2, MLK1, p38-alpha, p38-Beta, PAK1, PAK2, PAK4, PCTK1, PDGFRA, PDGFRB, PDPK1, PIK3C2B, PIK3CA, PIK3CG, PIM1, PIM2, PIM3, PKAC-alpha, PLK1, PLK3, PLK4, PRKCE, RAF1, RET, RIOK2, ROCK2, RSK2(Kin.DOM.1-N-TERMINAL), SNARK, SRC, SRPK3, TGFBR1, TIE2, TRKA, TSSK1B, TYK2 (JH1 domain-catalytic), ULK2, VEGFR2, YANK3, ZAP70, KIT(D816V), KIT(V559D, T670I), LKB1, MAP3K4, and KIT_was performed. The test compound was evaluated at a single dose of 500 nM. Kinase-tagged T7 phage strains were grown in parallel in 24-well blocks in an E. coli host derived from the BL21 strain. E. coli were grown to the log-phase and were then infected with T7 phage from a frozen stock (multiplicity of infection=0.4) and incubated at 32° C. with shaking until lysis (90-150 minutes). Lysates were centrifuged (6,000×g) and filtered (0.2 μm) to remove any cell debris. The remaining kinases were produced in HEK-293 cells and were then tagged with DNA for easy quantitative PCR (qPCR) detection. Magnetic beads coated with Streptavidin were treated with biotinylated small molecule ligands for 30 minutes at room temperature to generate the affinity resins for needed kinase assays. The liganded beads were blocked with excess biotin and washed with blocking buffer (SeaBlock (Pierce), 1% BSA, 0.05% Tween 20, 1 mM DTT) in order to remove unbound ligand and to also reduce non-specific phage binding. Binding reactions were assembled by combining kinases, liganded affinity beads, and 31 in 1× binding buffer (20% SeaBlock, 0.17×PBS, 0.05% Tween 20, 6 mM DTT). Compound 31 was prepared as 40× stocks in 100% DMSO and was directly diluted into the assay. All reactions were performed in polypropylene 384-well plates in a final volume of 40 μL. The assay plates were shook at room temperature for 1 hour and the affinity beads were washed with wash buffer (1×PBS, 0.05% Tween 20). Following the wash, beads were re-suspended in elution buffer (1×PBS, 0.05% Tween 20, 0.5 μM non-biotinylated affinity ligand) and incubated at room temperature with shaking for 30 minutes. Kinase concentration in eluates was measured by qPCR (FIG. 6).

TABLE 3

| | | | SH-05-19 | | SH-04-54 | | SH-05-07 | | IC50 (M) |
|---|---|---|---|---|---|---|---|---|---|
| Kinases | Cpd. dose (uM) | DMSO | Data 1 | Data 2 | Data 1 | Data 2 | Data 1 | Data 2 | Staurosporine |
| AKT1 | 5 | 98.87 | 90.56 | 87.91 | 92.08 | 97.52 | 94.62 | 92.09 | 2.08E−09 |
| ERK1 | 5 | 98.72 | 119.01 | 126.49 | 110.67 | 105.13 | 109.56 | 106.21 | 8.96E−07 |
| c-Src | 5 | 98.34 | 41.63 | 39.16 | 50.83 | 46.67 | 58.27 | 54.21 | <1.00E−9 |
| JAK1 | 5 | 101.87 | 98.34 | 97.79 | 100.56 | 97.78 | 100.60 | 97.99 | <1.00E−9 |
| JAK2 | 5 | 106.37 | 46.12 | 47.70 | 62.01 | 59.06 | 67.07 | 61.26 | <1.00E−9 |

% Enzyme activity of the compounds relative to DMSO (control)

Cytotoxicity Studies

BTSC spheres were dissociated to single cells with the enzyme Accumax (Innovative Technologies), seeded at 1500 cells/96-well and treated with drug or vehicle (DMSO) one day after plating. Cytotoxicity studies were repeated independently at Sickkids Hospital using BTSC lines 25M, 67EF, 73EF, 84EF and 127EF. BTSC spheres were dissociated to single cells as above and plated in 96 well plates in triplicate at 3000 cells/96-well. In both sets of experiments drugs were used as serial dilutions within the range of 5 μM to 100 nM in the first set and 25 μM to 10 nM. Cell viability following drug treatment was assessed three days later using the ALAMARBLUE™ assay (Invitrogen) according to the manufacturer's instructions. All culture experiments were performed in triplicate with a minimum of three wells per condition. Table 4 below illustrates a screen of the library against a number of BTSCs using ALAMARBLUE™ assay.

TABLE 5

| Compound | $IC_{50}$ (nM) in BTSC 30M |
|---|---|
| 1 | 1.32 ± 0.04 |
| 22 | 0.526 ± 0.013 |
| 31 | 0.4325 ± 0.022 |
| 32 | 1.136 ± 0.009 |
| 33 | 0.7236 ± 0.013 |

Western Blotting

BTSC spheres were lysed in modified RIPA buffer supplemented with Complete Mini protease (Roche) and Halt phosphatase (Thermo Scientific) inhibitor cocktails. For protein analysis following drug treatment, BTSC spheres were dissociated to single cells and $1\times10^6$ cells were treated with drug or vehicle (DMSO) for 2, 24 or 72 hours. 15 μg of protein were loaded on 7.5% or 10% SDS-PAGE gels and

TABLE 4 screen of the library against a number of BTSCs using ALAMARBLUE ™ assay

| | Cell line | | | | | | | |
|---|---|---|---|---|---|---|---|---|
| | 30M | | 68EF | | 73M | | 147EF | |
| Drugs | IC50 (μm) | IC50 Std. Error | IC50 (μm) | IC50 Std. Error | IC50 (μm) | IC50 Std. Error | IC50 (μm) | IC50 Std. Error |
| 8 | 0.5219 | +/−0.014 | 0.5896 | +/−0.020 | 1.103 | +/−0.012 | 0.6689 | +/−0.015 |
| 9 | no effect | — | no effect | — | no effect | — | no effect | — |
| 10 | 1.3261 | +/−008 | 1.723 | +/−0.013 | 1.806 | +/−0.019 | 1.456 | +/−0.013 |
| 11 | no effect | — | no effect | — | no effect | — | no effect | — |
| 12 | no effect | — | — | — | no effect | — | — | — |
| 13 | no effect | — | — | — | no effect | — | — | — |
| 14 | 0.7175 | +/−0.013 | 0.8064 | +/−0.011 | 1.809 | +/−0.006 | — | — |
| 15 | 0.6073 | +/−0.007 | — | — | — | — | — | — |
| 16 | 0.9503 | +/−0.016 | 0.839 | +/−0.009 | 2.036 | +/−0.007 | — | — |
| 17 | 0.6936 | +/−0.014 | 0.6312 | +/−0.006 | 1.24 | +/−0.008 | — | — |
| 18 | no effect | — | 4.832E-13 | +/−5.6 | no effect | — | 3.585 | +/−0.0095 |
| 20 | 0.6638 | +/−0.012 | no effect | — | 1.824 | +/−0.009 | — | — |
| 21 | — | — | — | — | no effect | — | — | — |
| 22 | 0.526 | +/−0.013 | 0.8909 | +/−0.012 | 1.45 | +/−0.016 | 0.7755 | +/−0.010 |
| 23 | no effect | — | no effect | — | no effect | — | no effect | — |
| 26 | 1.948 | +/−0.046 | — | — | 4.336 | +/−0.004 | — | — |
| 27 | no effect | — | no effect | — | — | — | — | — |
| 28 | no effect | — | 3.784E-07 | +/−1.31 | no effect | — | no effect | — |
| 29 | 0.9409 | −/+0.005 | 1.091 | +/−0.013 | — | — | — | — |
| 30 | 0.7759 | +/−0.016 | — | — | 2.841 | +/−0.013 | — | — |
| 31 | 0.4325 | +/−0.022 | 0.5315 | +/−0.070 | 1.031 | +/−0.031 | 0.3146 | +/−0.027 |
| 32 | 1.136 | +/−0.009 | ~1.006 | +/−0.010 | 1.52 | +/−3.4 | 0.5883 | +/−0.013 |
| 33 | 0.7236 | +/−0.013 | 1.46 | +/−0.027 | 1.227 | +/−0.008 | 0.9347 | +/−0.013 |
| 34 | 2.227 | +/−0.030 | — | — | no effect | — | — | — |
| 35 | no effect | — | no effect | — | 2.766 | +/−0.009 | — | — |
| 36 | — | — | — | — | no effect | — | — | — |
| 37 | no effect | — | — | — | no effect | — | — | — |
| 38 | 2.072 | +/−0.006 | 3.046 | +/−0.042 | 2.553 | +/−0.030 | — | — |
| 39 | 1.094 | +/−0.005 | 0.6073 | +/−0.007 | 3.315 | +/−0.017 | — | — |
| 40 | — | — | — | — | no effect | — | — | — |
| 41 | — | — | — | — | 3.497 | +/−0.027 | — | — |
| 42 | no effect | — | — | — | no effect | — | — | — |
| 43 | no effect | — | no effect | — | no effect | — | no effect | — |
| 44 | no effect | — | 1.74 | +/−0.035 | no effect | — | 2.453 | +/−0.017 |
| 45 | no effect | — | no effect | — | no effect | — | no effect | — |
| 46 | no effect | — | — | — | no effect | — | no effect | — |

When $IC_{50}$ was evaluated in tests conducted side-by-side with compound 1 of the prior art and compounds 22 and 31-33, the results are conclusive. The compounds of the present invention have a better $IC_{50}$ than compound 1 (see Table 5 below)

transblotted to nitrocellulose membranes. Blots were stained with the following antibodies: phospho-STAT3 Y705 (1:1000, Cell Signalling Technology), phospho-STAT3 S727 (1:1000, Cell Signalling Technology), STAT3 (1:1000, Santa Cruz Biotechnology), Bcl-xL (1:1000, Cell Signalling Technology), cyclin D1 (1:1000, Cell Signalling Technology) PARP (1:1000, Cell Signalling Technology) and Actin (1:2500, Santa Cruz Biotechnology). HRP conjugated secondary antibodies, goat anti-rabbit (Cell Signalling Technology) were used at 1:2000 and donkey anti-mouse, donkey anti-goat, and goat anti-rabbit, (Calbiochem) were used at 1:6000. Bands were visualized with the ECL Plus Western Blotting Detection System and Hyperfilm (Amersham).

Brain Tumor Sphere Culture

GBM BTSCs were cultured from a series of tumor specimens obtained following informed consent from adult GBM patients during their operative procedure as previously described (Kelly et al, Stem Cells 2009) and approved by the University of Calgary Ethics Review Board. Briefly, BTSC cultures were initiated in serum-free defined culture medium (SFM) and gave rise to nonadherent spheres after 7 to 21 days in culture. Primary tumor spheres were expanded for several passages and then cryopreserved in 10% DMSO (Sigma Aldrich) in serum-free defined medium until use in experiments. Human fetal neural stem cells were also cultured as previously described and induced to differentiate into astrocytes by addition of 10% fetal bovine serum and removal of EGF, FGF-2 and heparan sulfate.

Fluorescence Polarization Assay

STAT3, STAT5 and STAT1: The fluorescence polarization studies were performed on an Infinite M1000 (Tecan, Crailsheim, Germany) machine using black 384-round bottom well plates (Corning). The buffer used contained 50 mM NaCl, 10 mM Hepes, pH 7.5, 1 mM EDTA and 2 mM dithiothreitol and a final concentration of 5% DMSO.

Figure 7:
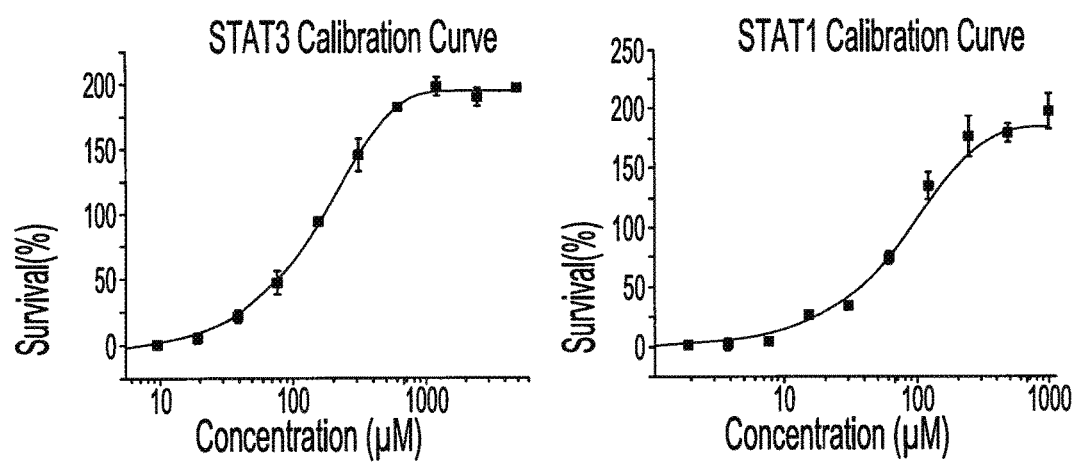
FIG. 7 is a calibration curve performed using 10 nM Fam-pYLPQTV and dilutions of STAT3 and STAT1 protein (5.0 µL to 2.4 nM) at a final DMSO concentration of 10%.

Test compounds were dissolved in DMSO and diluted using a dilution medium consisting of 50 mM NaCl, 10 mM Hepes, pH 7.5, 1 mM EDTA, and 2 mM dithiothreitol. Fluorescently-labelled pYLPQTV peptide (FAM-pYLPQTV) was kept at a final concentration of 10 nM in the buffered solution. Non-labelled pYLPQTV peptide was dissolved in DMSO and diluted using the dilution medium for use as a positive control. A calibration curve was performed using 10 nM Fam-pYLPQTV and dilutions of STAT3 and STAT1 protein (5.0 µL to 2.4 nM) at a final DMSO concentration of 10% (FIG. 7).

Figure 8:
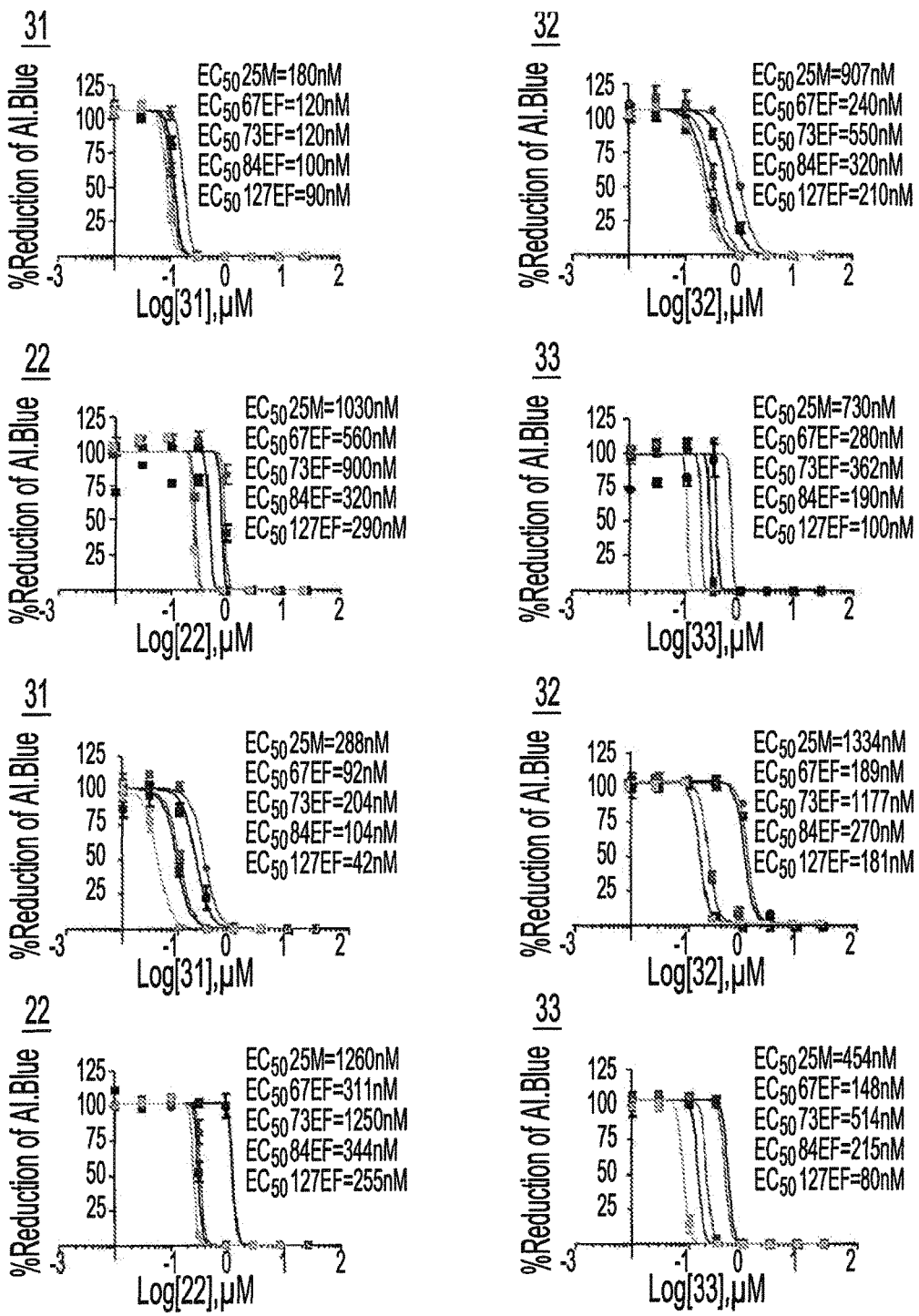
FIG. 8 illustrates the screening of compounds 22, 31, 32, and 33 against a number of BTSCs, where each compound was screened twice at various concentrations'

The midpoint of the saturation curve was used to determine the STAT3 concentration required for the competitive fluorescent polarization assay. 7.5 µL of FAM-pYLPQTV peptides was added to the already plated 15 µL of a 750 nM STAT3 protein solution in 384-flat well plates. 7.5 µL of inhibitory molecules (and positive control) solution were individually added to the plate. The final inhibitory concentrations were 100 µL, 50 µL, 25 µL, 12.5 µL, 6.3 µL, or 3.1 µL. The 10% DMSO buffer solution was incubated for 15-30 minutes before signal measurements by the Infinite M1000. Results for compounds 22, 31, 32, and 33 are illustrated in FIG. 8.

Surface Plasmon Resonance (SPR) studies

Interactions of His-tagged STAT3 with small molecules were investigated using SPR spectroscopy. The binding experiments were carried out on a ProteOn XPR36 (Bio-Rad) biosensor at 25° C. using the HTE sensor chip (Bio-Rad, Ontario, Canada). The flow cells of the sensor chip were loaded with a nickel solution at 30 µL/min for 120 s to saturate the Tris-NTA surface with Ni(II) ions. Purified His-tagged STAT3 and STAT5 (SignalChem, British Columbia, Canada) in PBST buffer (PBS with 0.005% (v/v) Tween-20 and 0.001% DMSO pH 7.4) was injected in the first and second channels of the chip respectively in the vertical direction at a flow rate of 25 µg/µL for 300 s, which attained, on average, ~8000 resonance unit (RU). After a wash with PBST buffer, inhibitors binding to the immobilized proteins were monitored by injecting a range of concentrations along with a blank at a flow rate of 100 µL/min for 200 s for each of these small molecules. When the injection of the small molecule inhibitor was completed, running buffer was allowed to flow over the immobilized substrates for the non-specifically bound inhibitors to dissociate for 600 s. Following dissociation of the inhibitors, the chip surface was regenerated with an injection of 1 M NaCl at a flow rate of 100 µL/ml for 18 s. Interspot channel reference was used for non-specific binding corrections and the blank channel used with each analyte injection served as a double reference to correct for possible baseline drift. Data were analyzed using ProteOn Manager Software version 3.1. The Langmuir 1:1 binding model was used to determine the $K_D$ values.

Control experiments were conducted to validate protocol.

STAT5 peptide sequence binding to His-Tagged-STAT5 using the protocol above:

$K_{D(STAT3)} = 14.9$ µM $K_{D(STAT5)} = 262$ nM

STAT3 peptide sequence binding to His-Tagged-STAT3 using the protocol above:

$K_{D(STAT3)} = 135$ nM $K_{D(STAT5)} =$ No binding

Comparison Data to WP1066 and Cucurbitacin

Since these inhibitors are designed with the aim to target STAT3, they are most potent in cell lines which are highly reliant on the STAT3 protein. BTSCs are amongst the most deadly STAT3 dependent cancer cell lines identified to date and it is thus why these cell lines display such sensitivity to our STAT3 inhibitors. Nevertheless, as expected, these compounds could also be used to treat other cancers. The rationale is that since the compounds described herein can effectively kill the very resistant and highly deadly BTSCs which are almost irresponsive to most chemotherapy agents, they can be applied against a variety of other cancer cells as well.

In addition to brain cancer, in order to evaluate the potential of the compounds of the present invention for treating other forms of cancer, the $IC_{50}$ for compounds 22, 31, 32, 23, et 33 (also referred to in the table as SH-04-08, SH-04-54, SH-05-07, SH-05-19, AND SH-05-23, respectively) was determined against other STAT3 dependent cancers such as Breast cancer cells (MDA-MB-468), Prostate (PPC1 or DU145) and leukemia cancer cells (AML-2) in parallel with BTSC 30M. The results are reported in Table 6 below.

TABLE 6

| Code | BTSC 30M | Breast Cancer (MDA-MB-468) | Prostate (DU145) | AML-2 |
|---|---|---|---|---|
| SH-04-08 | 900 nM | <1 uM | 12.0 uM | <1 uM |
| SH-04-54 | 500 nM | <1 uM | 11.3 uM | <1 uM |
| SH-05-07 | 971 nM | <1 uM | 15.9 uM | <1 uM |
| SH-05-19 | 505 nM | <1 uM | 9.8 uM | <1 uM |
| SH-05-23 | 689 nM | <1 uM | 14.2 uM | <1 uM |

Pancreatic Cancer

Low passage patient-derived pancreatic cancer line (Panc10.05) was plated in 96-well plates (3×10³ per well) and allowed to attach overnight. STAT3 inhibitors 31, 41, 42 and 38 were added at indicated concentrations. Cell survival was measured 72 h after drug addition with the MTS assay. The results are reported in FIG. 9.

Figure 9:
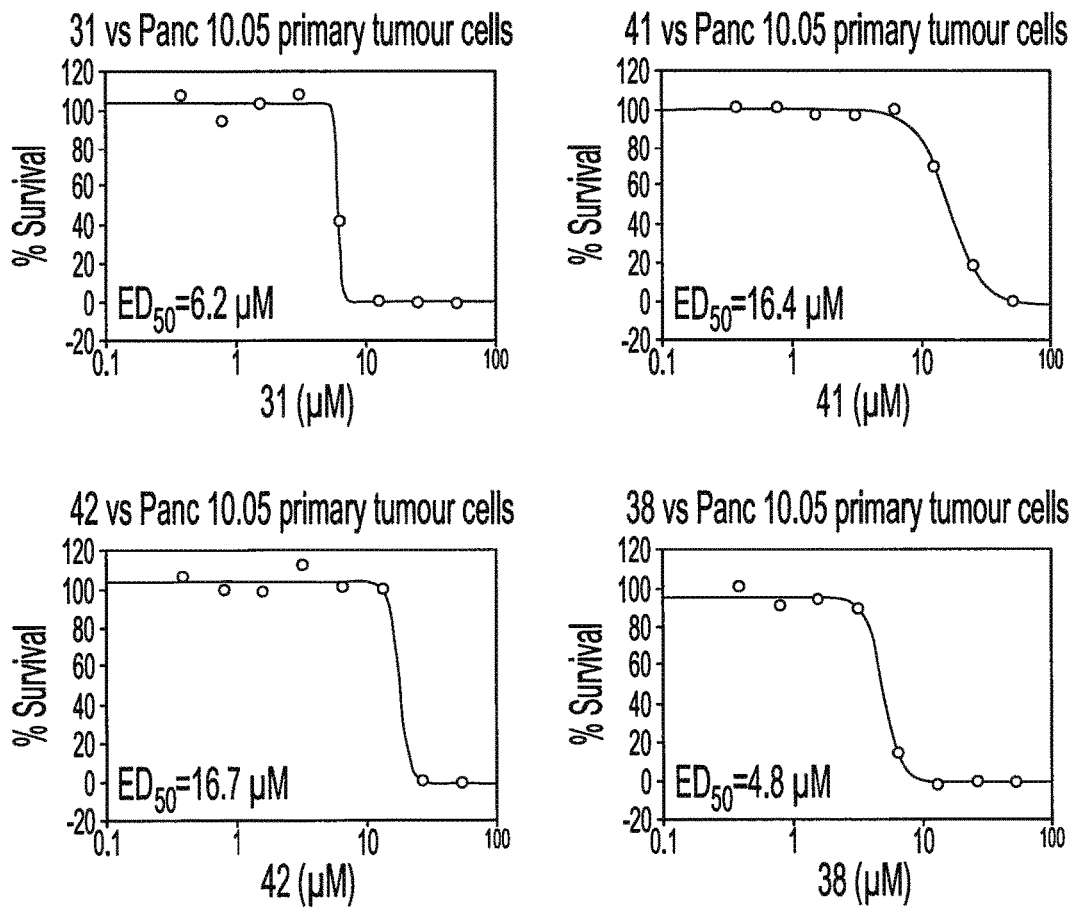
FIG. 9 illustrates the survival of pancreatic 10.05 patient cells treated with STAT3 inhibitors.

FIG. 9 illustrates the potent biological effects in a patient-derived pancreatic cancer cell line of the STAT3 inhibitors tested. $ED_{50}$ ($IC_{50}$) values calculated for compounds 31, 41, 42, and 38 are respectively of 6.2, 16.4, 16.7, and 4.8 µM.

Western Blot Analysis of pSTAT3 Inhibition

Low passage patient-derived pancreatic cancer lines (Pa03C and Panc10.05) were plated in 6-well plates ($2 \times 10^5$ and $8 \times 10^4$, respectively) and allowed to attach overnight. STAT3 inhibitors were added for 1 hr prior to IL-6 stimulation (50 ng/mL, 15 min). STAT3 inhibitors were present during IL-6 stimulation. Cells were harvested and lysed for Western blotting. phospho-Specific STAT3 antibody (Y705) was used to look at STAT3 phosphorylation and total STAT3 antibody was used to normalize activation of STAT3. Antibodies were from Cell Signaling and used at a 1:1000 dilution.

Figure 10:
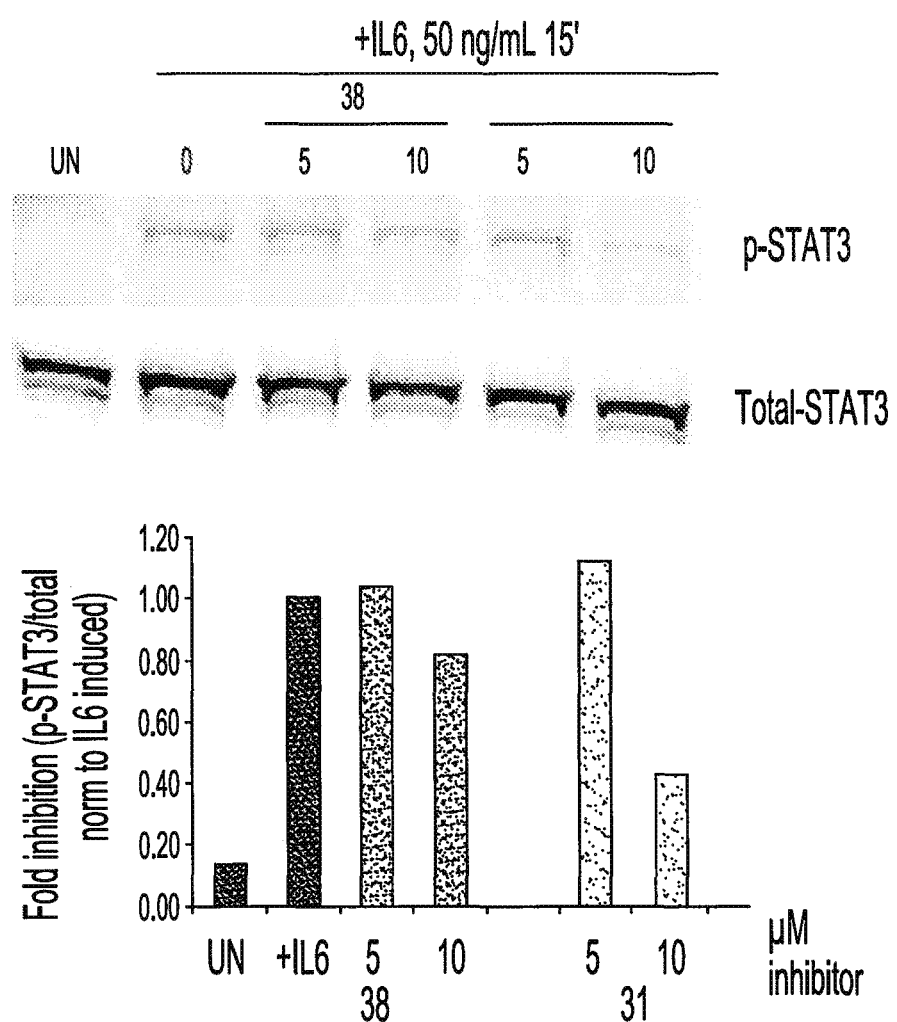
FIG. 10 illustrates the effect of Pa03C low passage patient cells pretreated with STAT3 inhibitor 1 hr and then stimulated with IL6 cytokine for 15 min.

As can be seen in FIG. 10, compound 31 potently inhibits de novo phosphorylation of STAT3 protein in pancreatic cancer cells.

Figure 11:
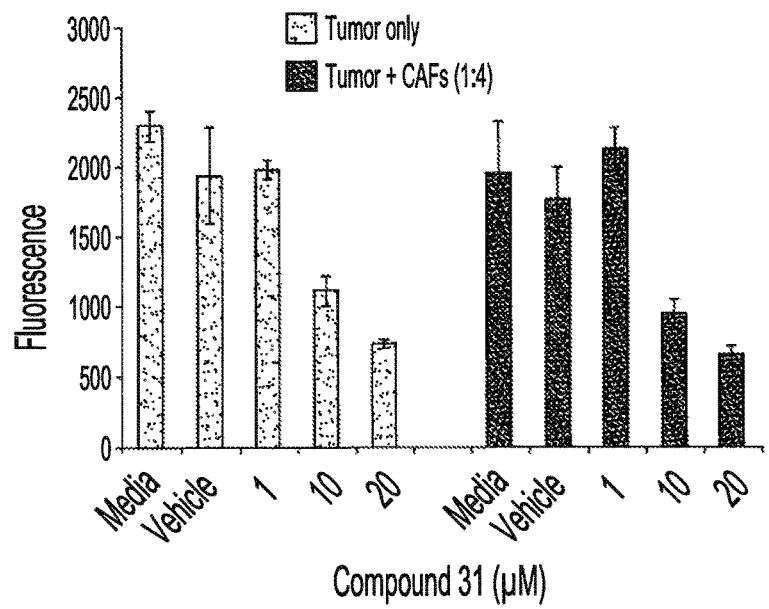
FIG. 11 illustrates the effects of STAT3 inhibitor 31 on low passage patient-derived pancreatic cancer line (Pa03C) plated in a 96-well plate coated with 1% Noble Agar in media containing 3% Matrigel, with and without cancer-associated fibroblasts.

As can be seen on FIG. 11, compound 31 effectively kills tumor cells grown in 3D cultures in the presence and absence of cancer-associated fibroblasts (CAFs). FIG. 11 illustrates the effects of STAT3 inhibitor 31 on low passage patient-derived pancreatic cancer line (Pa03C) plated in a 96-well plate coated with 1% Noble Agar in media containing 3% Matrigel, with and without cancer-associated fibroblasts. The ratio of the tumor to CAFs is 1:4. Tumor spheres begin to form around Day 3, and STAT3 inhibitor 31 added at Day 4 and 8. Cytotoxicity is assessed by fluorescence using Alamar Blue assay on Day 11.

Multiple Myeloma

MTT Cytotoxicity

For assessing MM cell viability, HMCL cells were seeded in 96-well plates in triplicate at a density of 20,000 cells/well and incubated with increasing concentrations of 16i and 21h or DMSO control and cell viability assessed by MTT (3-(4,5-dimethylthiazol)-2,5-diphenyl tetrazolium) colorimetric analysis. Results are reported at FIG. 12.

Figure 12:
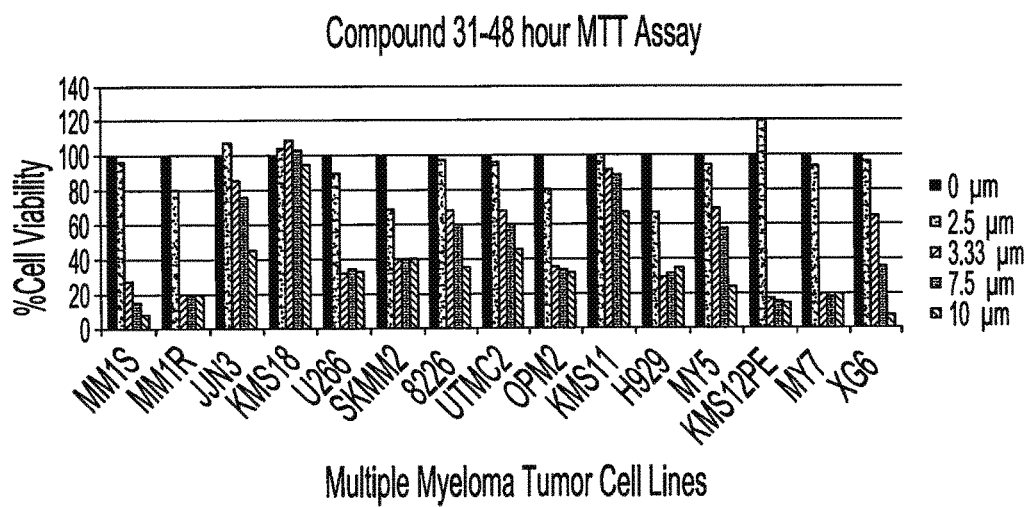
FIG. 12 illustrates compound 31 potently reducing cell viability in 12 of 15 different multiple myeloma tumor cell lines as assessed by MTT assay with calculated $ED_{50}$'s ranging from between 2-6 µM.

FIG. 12 illustrates compound 31 potently reducing cell viability in 12 of 15 different multiple myeloma tumor cell lines as assessed by MTT assay with calculated $ED_{50}$'s ranging from between 2-6 µM.

Brain Cancer

For Western blotting, BTSC spheres were dissociated with Accumax (eBioscience) and plated at $10^6$ cells/1.5 mL of media. Cells were treated with vehicle (DMSO) or drug and pelleted at select time points. For protein extraction, BTICs were lysed in modified RIPA buffer (50 mM Tris, 150 mM NaCl, 0.1% SDS, 0.5% Na Deoxycholate, 1% NP-40) supplemented with Complete Mini protease (Roche) and Halt phosphatase (Thermo Scientific) inhibitor cocktails. Protein concentrations were quantified using the BioRad protein assay; 11-15 µg of protein were loaded on 7.5% or 12% sodium dodecyl sulfate polyacrylamide gel electrophoresis (SDS PAGE) gels and transblotted to nitrocellulose membranes. Blots were stained with primary antibodies followed by horseradish peroxidase (HRP)-conjugated secondary antibodies. Primary antibodies included JAK2, p-JAK2, EGFR, pEGFR (Y1068), p-STAT3 Y705, p-STAT3 S727, cyclin D1, p-Akt S473, Akt, p-Erk1/2 T202/Y204, p-S6 S235/236, PARP, β-tubulin, PDGRβ, pPDGFRβ Y1009 (Cell Signaling Technology), Erk1/2 (Millipore), STAT3 and Actin (Santa Cruz Biotechnology), Secondary antibodies included donkey anti-mouse, donkey anti-goat and goat anti-rabbit (Calbiochem). Bands were visualized with the SuperSignal West Pico chemiluminescent substrate (Thermo Scientific) and Hyperfilm (Amersham).

For in vivo on-target Assessment, BTIC spheres from BT73 were enzymatically dissociated (Accumax, eBioscience) to single cell suspensions. Cells were washed in PBS and re-suspended at $10^5$ cells per 3 µL media for orthotopic xenografts. Six non-obese diabetic severe combined immunodeficiency (NOD SCID) mice were each xenografted with $10^5$ BT73 cells stereotactically implanted into the right striatum. Seven days following implants, mice were randomized into vehicle and drug cohorts and injected i.p., four days on, three days off, for a total of 10 doses. Drug-treated mice received a 10 mg/kg dose of compound 31 re-suspended in 100 µL 50% polyethylene glycol 300 (PEG 300, Sigma-Aldrich) in water. Vehicle-treated mice received an equal volume of 50% PEG 300 in water. Mice were euthanized with a lethal dose of sodium pentobarbitol, followed by transcardiac perfusion of 4% paraformaldehyde (PFA) two hours following injection of the last drug dose. Brains were removed, fixed in 4% PFA and cryosectioned at 12 µm for assessment by histology and immunohistochemistry. Hematoxylin and eosin (H&E) staining was performed according to standard protocols. Immunohistochemistry was performed by incubating with primary antibodies overnight at 4° C. followed by the Vectastain Elite mouse IgG or rabbit IgG kits (Vector Laboratories) and detection with DAB substrate and hematoxylin counterstaining (Sigma-Aldrich) according to the manufacturer's instructions. Primary antibodies included—STAT3 S727 (Cell Signaling Technology) and Ki67 (Novocastra). Secondary antibodies included biotin conjugated goat anti-rabbit (Jackson Immunoresearch).) Xenograft tumor cells undergoing apoptosis were also detected with the ApopTag Plus Peroxidase In Situ Apoptosis Detection Kit (Chemicon International, Inc., Temecula, Calif.) according to the manufacturer's instructions (TUNEL assay). Histology and immunohistochemistry and TUNEL assay images were acquired using the Olympus Slide Scanner and OlyVia software at the University of Calgary Regenerational Unit in Neurobiology Microscopy facility.

Figure 13:
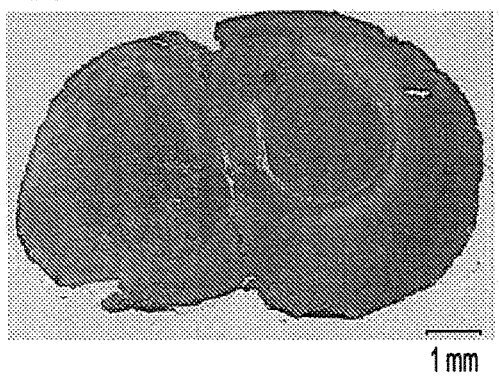
FIG. 13 illustrates the hematoxylin/eosin staining-hypercellular tumour dense areas staining (white) with hematoxylin in BT73 cells (A) without and (B) with inhibitor 31.
Figure 13:
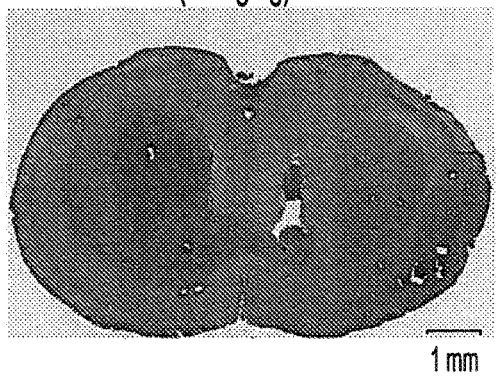

The results of the hematoxylin/eosin staining are reported in FIG. 13 illustrating sections of NOD-SCID mouse brains showing tumours from BT73 cells in control mice and in mice treated with inhibitor 31. Treatment with compound 31 resulted in significant decrease in tumour cells.

Figure 14:
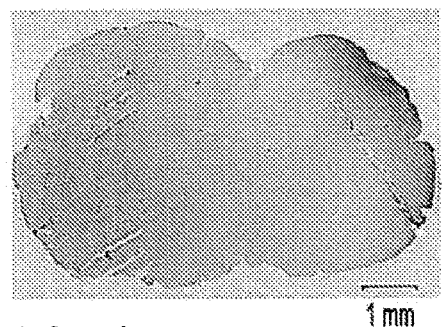
FIG. 14 illustrates the effect of compound 31 for decreasing pSTAT expression in mice orthotopically xenografted with BT73 brain cancer cells.
Figure 14:
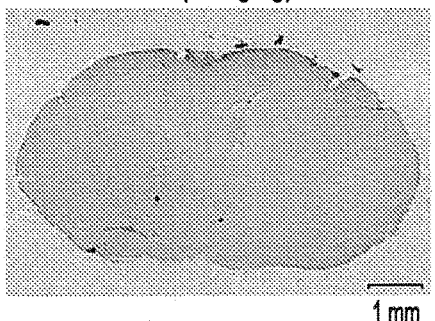
Figure 14:
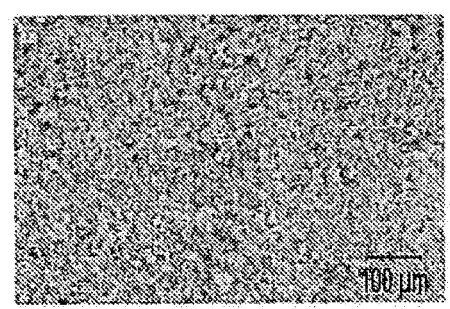
Figure 14:
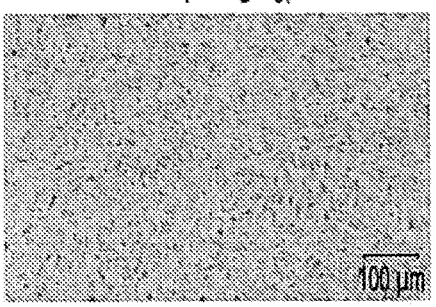

FIG. 14 illustrates the effect of compound 31 for decreasing pSTAT expression in mice orthotopically xenografted with BT73 brain cancer cells. As can be seen from FIG. 14, compound 31 displays on target effectiveness at reducing activated phospho-STAT as demonstrated by reduced immunohistochemical staining in treated tumours. (A) vehicle treated and (B) inhibitor 31 treated brains. Bottom panels are higher magnification of tumour regions in top panels.

Figure 15:
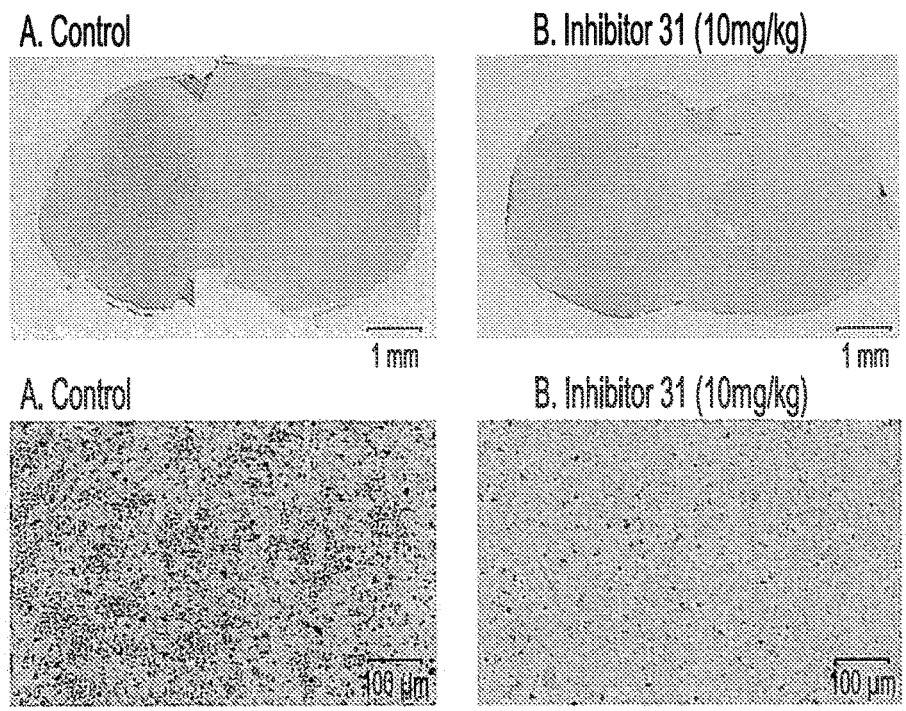
FIG. 15 illustrates the effect of compound 31 for reducing proliferation in BT73 brain tumours.

FIG. 15 illustrates the effect of compound 31 for reducing proliferation in BT73 brain tumours. Decreased expression of proliferation marker Ki67 is observed in mice treated with inhibitor 31 (A) vehicle treated and (B) inhibitor 31 treated brains. Bottom panels are higher magnification of tumour regions in top panels.

Figure 16:
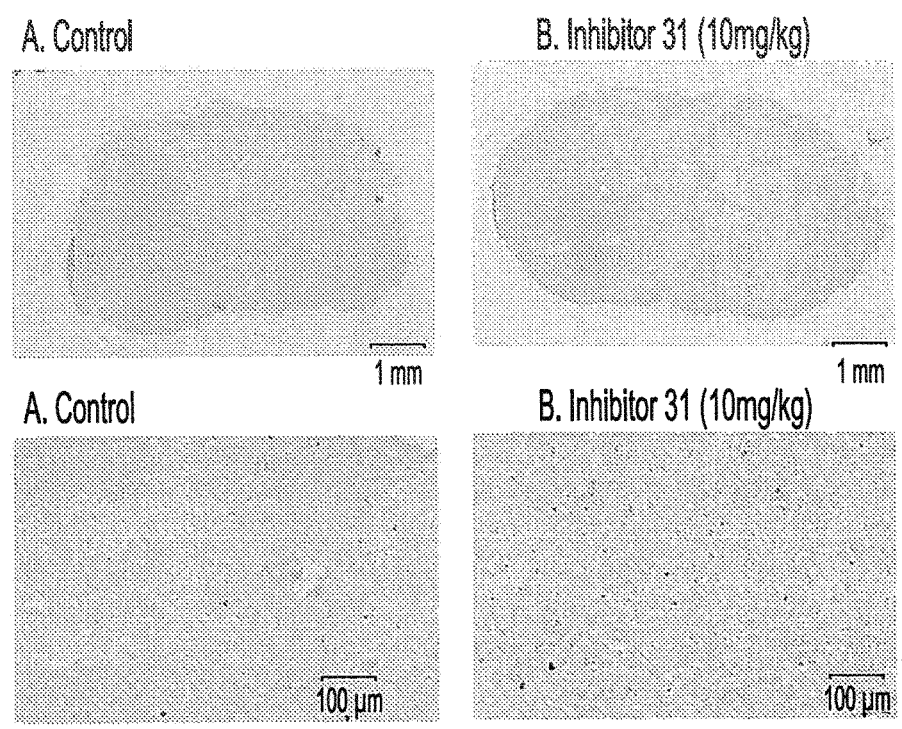
FIG. 16 illustrates an increased apoptosis (TUNEL staining) in mice treated with compound 31'

FIG. 16 illustrates an increased apoptosis (TUNEL staining) in mice treated with compound 31. Increased TUNEL staining demonstrating apoptic cell death is observed in the tumours of mice treated with compound 31. Panel (A) is vehicle treated and panel (B) is compound 31 treated brains. Bottom panels are higher magnification of tumour regions in top panels.

It has been shown herein that compound 31 is effective at reducing activated phospho-STAT3 in tumours generated by orthotopically xenografted human brain tumour stem cells in the brains of NOD-SCID mice, accompanied by a decrease in proliferation and increased cell death. The other compounds of the present invention are anticipated to have the same properties. In fact, other tests as reported hereinbefore have shown that compound 31 behave like other compounds tested. Here, in this experiment on brain cancer, compound 31 was used to demonstrate the general behavior of the compounds of the present invention.

Blood Brain Barrier Permeability

Compounds 31 and 32 were given to three mice at 10 mg/kg BID via IP for five days and blood was collected at two time points (30 min. and 300 min.) for all mice. Plasma was separated from blood by centrifugation and stored at −20° C. until analysis. Brain was also collected from one mouse at each dose. Concentrations of compounds were determined using LC-MS.

Figure 17:
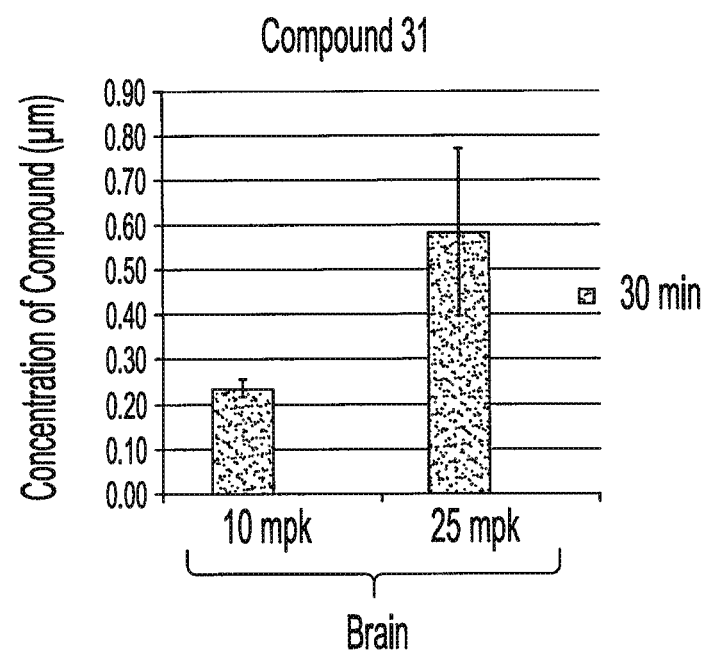
FIG. 17 illustrates that concentration of compound 31 was found to be present in the brain with different dosing (10 mg/kg and 25 mg/kg) as assessed by LCMS.

As can be seen on FIG. 17, compound 31 was found to be present in the brain with different dosing (10 mg/kg and 25 mg/kg) as assessed by LCMS. Compound 31 accumulates up to 0.7 µM concentrations in the brain in mice models.

Figure 18:
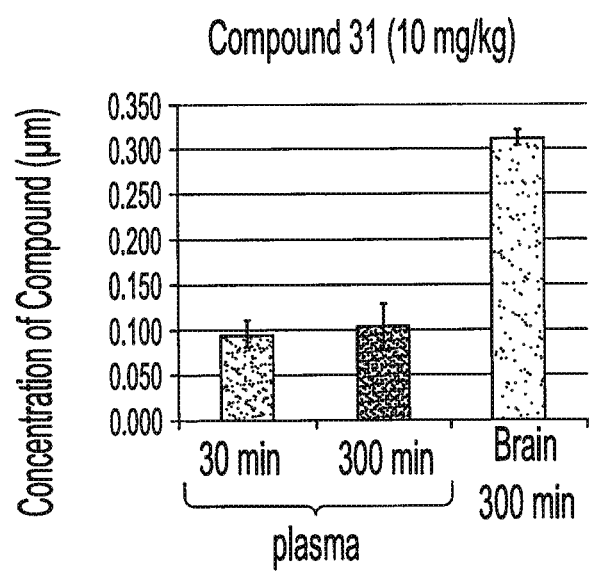
FIG. 18 illustrates the concentration of compound 31 found in the brain as assessed by LCMS.

As can be seen from FIG. 18, compound 31 accumulates up to 300 nM concentrations in the brain in mice models at 10 mg/kg dosing.

Figure 19:
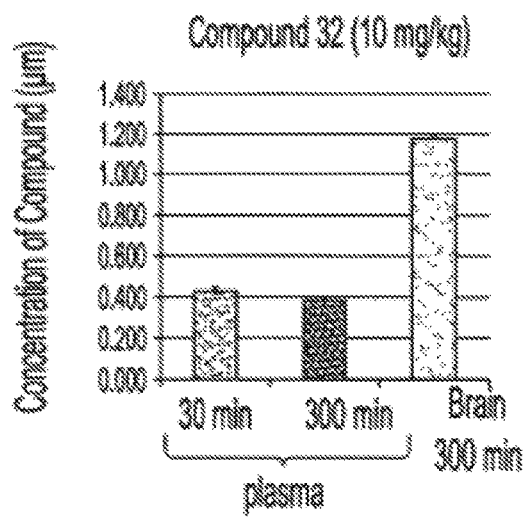
FIG. 19 illustrates the concentration of compound 32 found in the brain as assessed by LCMS.

As can by seen from FIG. 19, compound 32 accumulates up to ~1.2 µM concentrations in the brain in mice models at 10 mg/kg dosing.

Plasma concentration of compound 31 increased dose dependently from 0.24 µM to 0.58 µM for 10 and 25 mg/kg, respectively. However, no compound was detected after 5 hr at both doses indicating a fast clearance. Plasma concentration did not change significantly between 30 min. and 300 min for both compounds 31 and 32. For compound 31, about 0.3 µM compound was seen in the brain of 10 mg/kg dosed mouse. The brain concentration of compound 32 was at ~1.2 µM for 10 mg/kg dosed mouse. The above is a clear indication that the compounds of the present invention can cross the blood brai barrier.

Breast Cancer

Inhibition of cell proliferation in ErbB2 mammary breast tumour cell lines (NIC)

Compounds were assessed for inhibition of cell proliferation in ErbB2 mammary breast tumour cell lines (NIC) containing the activated form of ErbB2 using a CyQuant Assay. Compound 31 was directly compared to BP-1-102 over a range of concentrations.

Protocol of CyQuant Proliferation Assay

Three individual Mouse Mammary Tumour Virus ErbB2 mammary tumour cell lines (NIC) were resuspended in 10% FBS plus single quots DMEM media to a final concentration of 40,000 cells per 1 mL. Cells were plated at a concentration of 4,000 cells in 100 µL of media per well on 96 well NUNC plates and incubated for 24 h hours at 37° C. plus 5% $CO_2$. After 24 hours the media was aspirated and replaced with either normal media, media+DMSO (1:1000) or media containing the appropriate concentration of drug (BP1-102 5 µM, 10 µM or 20 µM or compound 31, also referred to herein as SH-04-54 5 µM, 10 µM or 20 µM). Each condition was repeated in quadruplicate. At predetermined time points; at treatment, 24 h, 48 h and 72 h post treatment, the media was removed from the cells and the plates were stored at −80° C. wrapped in tin foil. When needed, all the plates were thawed to room temperature. Invitrogen's CyQuant Cell Proliferation Assay kit was used to measure DNA content. Following their directions, the cell lysis buffer was diluted 1:20 with water and then the CyQuant GR solution 1:400 in the lysis buffer. 200 µL of the Cyquant solution was added to each well and the plate protected from light. The plates were then incubated for 2-5 minutes protected from light, then read on a fluorescence microplate reader with filters for 480 nm excitation and 520 nm emission maxima. Quadruplicates were averaged and the error bars represent the S.E.M. In some cases the absorbance was normalized to the DMSO control.

Figure 20:
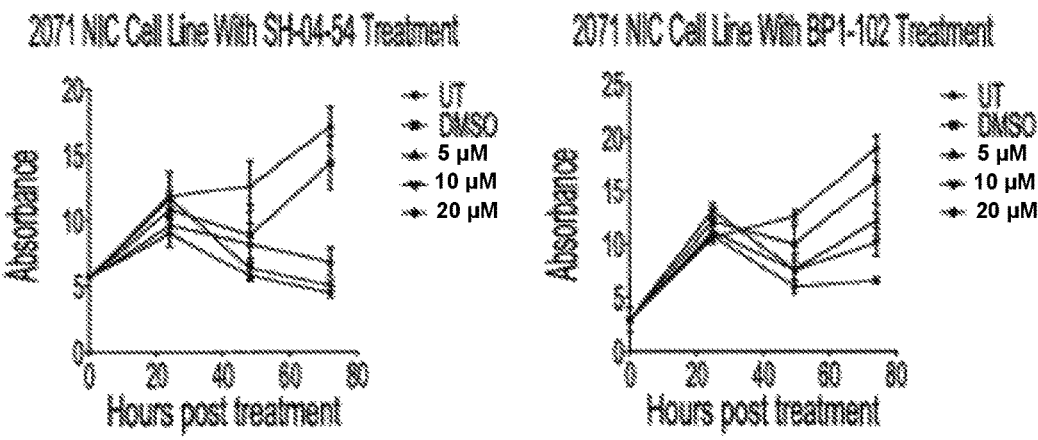
FIG. 20 illustrates the fluorescence of 2071 NIC Cell Line treated with compound 31 (SH-04-54) or with BP1-102.

In FIG. 20, cells were plated at 4,000 cells per well in a 96 well plate, incubated for 24 hours then treated with 31 at 5 µM, 10 µM and 20 µM for 24, 48 and 72 hours. Plates were stored at −80° C. Plates were thawed and treated with Invitrogen's Cyquant Cell Proliferation Assay which measures DNA content. Fluorescence was measured using a fluorescence microplate reader with filters at 480 nm and 520 nm. Each data point was done in quadruplicate and error bars represent S.E.M.

Figure 21:
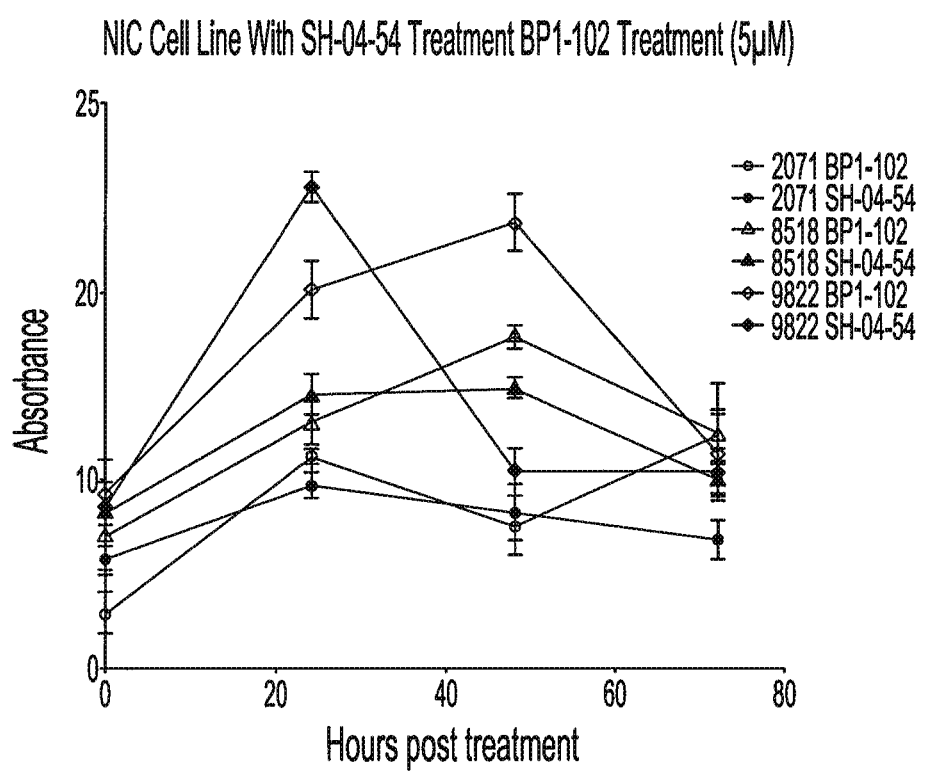
FIG. 21 illustrates the fluorescence of various NIC Cell Line treated with compound 31 (SH-04-54) or with BP1-102.

In FIG. 21, cells were plated at 4,000 cells per well in a 96 well plate, incubated for 24 hours then treated with BP1-102 or compound 31 at 5 µM for 24, 48 and 72 hours. Plates were stored at −80° C. Plates were thawed and treated with Invitrogen's Cyquant Cell Proliferation Assay which measures DNA content. Fluorescence was measured using a fluorescence microplate reader with filters at 480 nm and 520 nm. Each data point was done in quadruplicate and error bars represent S.E.M.

As can be appreciated, compound 31 is potent at 5 µM in MMTV ErbB2 mammary tumour cell lines (NIC), completely inhibiting cell proliferation in 2071 NIC cells. In comparison with BP1-102, compound 31 was shown to be more potent over three different breast cancer NIC cell lines, 2071, 8518 and 9822.

While the disclosure has been described in connection with specific embodiments thereof, it is understood that it is capable of further modifications and that this application is intended to cover any variation, use, or adaptation of the disclosure following, in general, the principles of the disclosure and including such departures from the present disclosure that come within known, or customary practice within the art to which the disclosure pertains and as may be applied to the essential features hereinbefore set forth, and as follows in the scope of the appended claims.

The invention claimed is:
1. A compound of formula I:

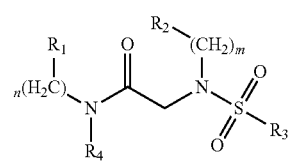

or a pharmaceutically acceptable salt, solvate or prodrug thereof,
wherein each of m and n are independently an integer from 0-3;
wherein $R^1$ is selected from $A^1$, $A^2$, -($A^1$)-($A^2$), -($A^2$)-($A^3$), -($A^3$)-($A^2$), -($A^3$)-($A^4$), -($A^5$)-($A^1$)-($A^7$), -($A^5$)-($A^2$)-($A^8$), -($A^5$)-($A^3$)-($A^7$), and -($A^5$)-($A^6$)-L-($A^7$);
wherein $A^1$ is $C_{3-6}$ cycloalkyl, and substituted with 0-3 groups selected from halo, hydroxyl, amino, nitro, cyano, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)-alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy, (C<sub>1-6</sub>)-alkyl-(C<sub>1-6</sub>)-alkylthio, (C<sub>1-6</sub>)-alkyl-(C<sub>1-6</sub>)-haloalkylthio, (C<sub>1-6</sub>)-alkyl-(C<sub>1-6</sub>)-polyhaloalkylthio, $CO_2H$, $(C=O)R^5$, $(C=O)OR^5$, and $(C=O)NHR^5$;

wherein $A^2$ is $C_{3-6}$ cycloalkyl or heterocycloalkyl, substituted with 0-3 groups selected from halo, hydroxyl, amino, nitro, cyano, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)-alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy (C<sub>1-6</sub>)-alkyl-(C<sub>1-6</sub>)-alkylthio, (C<sub>1-6</sub>)-alkyl-(C<sub>1-6</sub>)-haloalkylthio, (C<sub>1-6</sub>)-alkyl-(C<sub>1-6</sub>)-polyhaloalkylthio, $CO_2H$, $(C=O)R^6$, $(C=O)OR^6$, and $(C=O)NHR^6$;

wherein $A^3$ is aryl, and substituted with 0-3 groups selected from halo, hydroxyl, amino, nitro, cyano, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)- alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy, (C<sub>1-6</sub>)-alkyl-(C<sub>1-6</sub>)-alkylthio, (C<sub>1-6</sub>)-alkyl-(C<sub>1-6</sub>)- haloalkylthio, (C<sub>1-6</sub>)-alkyl-(C<sub>1-6</sub>)-polyhaloalkylthio, $CO_2H$, $(C=O)R^7$, $(C=O)OR^7$, and $(C=O)NHR^7$;

wherein $A^4$ is aryl, and substituted with 1-3 groups selected from halo, hydroxyl, amino, nitro, cyano, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)-alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy, (C<sub>1-6</sub>)-alkyl-(C<sub>1-6</sub>)-alkylthio, (C<sub>1-6</sub>)-alkyl-(C<sub>1-6</sub>)-haloalkylthio, (C<sub>1-6</sub>)-alkyl-(C<sub>1-6</sub>)-polyhaloalkylthio, $CO_2H$, $(C=O)R^8$, $(C=O)OR^8$, and $(C=O)NHR^8$;

wherein $A^5$ is selected from $C_{3-6}$ cycloalkyl, $C_{3-6}$ heterocycloalkyl, and aryl, and substituted with 0-3 groups selected from halo, hydroxyl, amino, nitro, cyano, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)-alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy, (C<sub>1-6</sub>)-alkyl-(C<sub>1-6</sub>)-alkylthio, (C<sub>1-6</sub>)-alkyl-(C<sub>1-6</sub>)-haloalkylthio, (C<sub>1-6</sub>)-alkyl-(C<sub>1-6</sub>)-polyhaloalkylthio, $CO_2H$, $(C=O)R^9$, $(C=O)OR^9$, and $(C=O)NHR^9$;

wherein $A^6$ is selected from $C_{3-6}$ cycloalkyl, $C_{3-6}$ heterocycloalkyl, and aryl, and substituted with 0-3 groups selected from halo, hydroxyl, amino, nitro, cyano, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)-alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy, (C<sub>1-6</sub>)-alkyl-(C<sub>1-6</sub>)-alkylthio, (C<sub>1-6</sub>)-alkyl-(C<sub>1-6</sub>)-haloalkylthio, (C<sub>1-6</sub>)-alkyl-(C<sub>1-6</sub>)-polyhaloalkylthio, $CO_2H$, $(C=O)R^{10}$, $(C=O)OR^{10}$, and $(C=O)NHR^{10}$;

wherein $A^7$ is selected from $C_{3-6}$ cycloalkyl, $C_{3-6}$ heterocycloalkyl, and aryl, and substituted with 0-3 groups selected from halo, hydroxyl, amino, nitro, cyano, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)-alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy, (C<sub>1-6</sub>)-alkyl-(C<sub>1-6</sub>)-alkylthio, (C<sub>1-6</sub>)-alkyl-(C<sub>1-6</sub>)-haloalkylthio, (C<sub>1-6</sub>)-alkyl-(C<sub>1-6</sub>)-polyhaloalkylthio, $CO_2H$, $(C=O)R^{11}$, $(C=O)OR^{11}$, and $(C=O)NHR^{11}$;

wherein $A^8$ is selected from $C_{3-6}$ cycloalkyl, $C_{3-6}$ heterocycloalkyl, and aryl, and substituted with 0-3 groups selected from halo, hydroxyl, amino, nitro, C<sub>1-6</sub> haloalkyl, C<sub>1-6</sub> polyhaloalkyl, C<sub>1-6</sub> alkoxy, C<sub>1-6</sub> haloalkoxy, C<sub>1-6</sub> polyhaloalkoxy, C<sub>1-6</sub> alkylthio, C<sub>1-6</sub> haloalkylthio, C<sub>1-6</sub> polyhaloalkylthio, C<sub>1-6</sub> alkylamino, C<sub>1-6</sub> dialkylamino, (C<sub>1-6</sub>)-alkyl-(C<sub>1-6</sub>)-alkoxy, (C<sub>1-6</sub>)-alkyl-(C<sub>1-6</sub>)-haloalkoxy, (C<sub>1-6</sub>)-alkyl-(C<sub>1-6</sub>)-polyhaloalkoxy, (C<sub>1-6</sub>)-alkyl-(C<sub>1-6</sub>)-alkylthio, (C<sub>1-6</sub>)-alkyl-(C<sub>1-6</sub>)-haloalkylthio, (C<sub>1-6</sub>)-alkyl-(C<sub>1-6</sub>)-polyhaloalkylthio, $CO_2H$, $(C=O)R^{12}$, $(C=O)OR^{12}$, and $(C=O)NHR^{12}$;

wherein L is selected from —(C=O)— and —$SO_2$—;

wherein each of $R^5$, $R^6$, $R^7$, $R^8$, $R^9$, $R^{10}$, $R^{11}$, and $R^{12}$ is independently selected from hydrogen, C<sub>1-6</sub> alkyl, C<sub>1-6</sub> haloalkyl, and C<sub>1-6</sub> polyhaloalkyl; or a pharmaceutically acceptable salt, hydrate, solvate, or polymorph thereof, wherein $R^2$ is selected from the group consisting of:

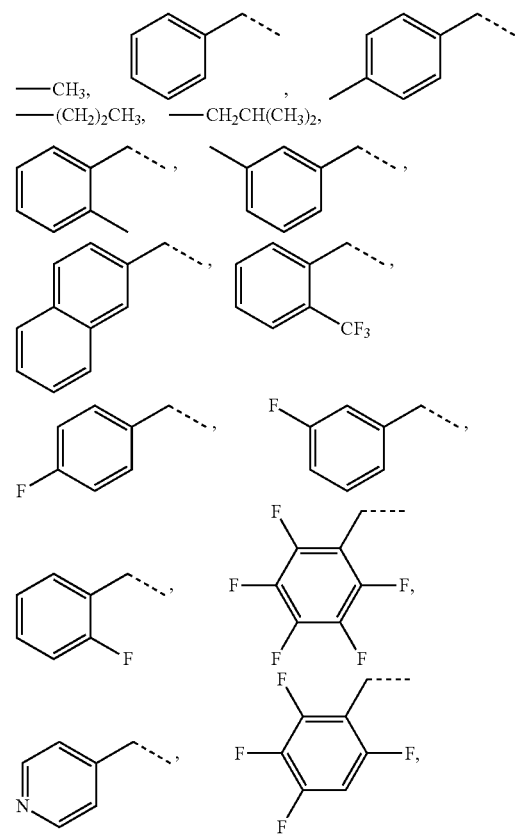

-continued
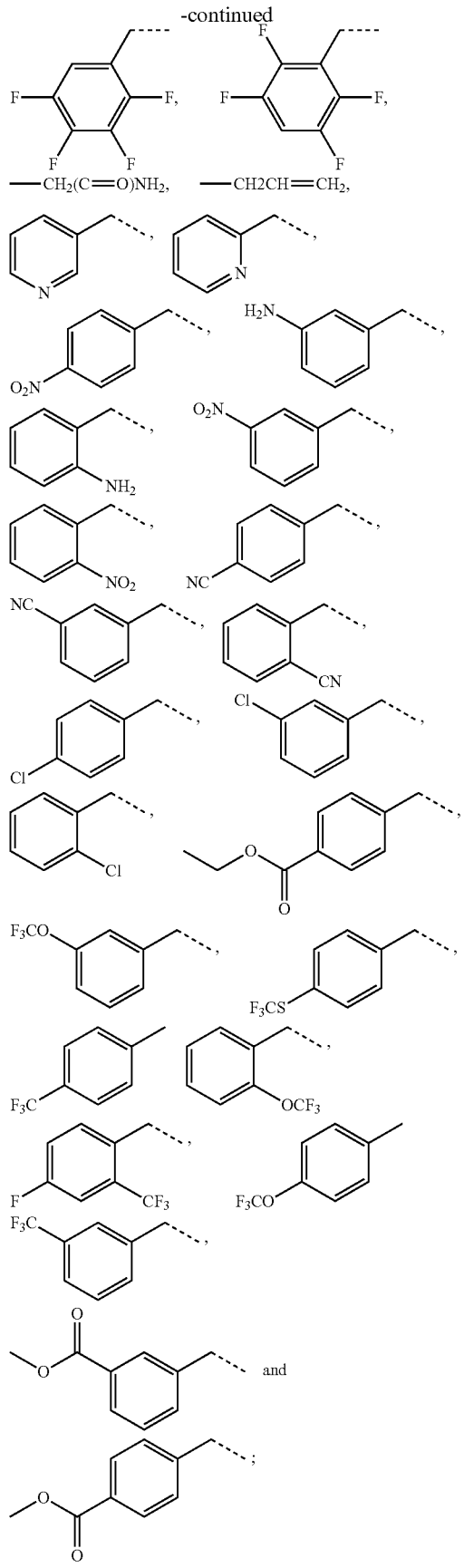
and
wherein $R_3$ is selected from the structure represented by formula:
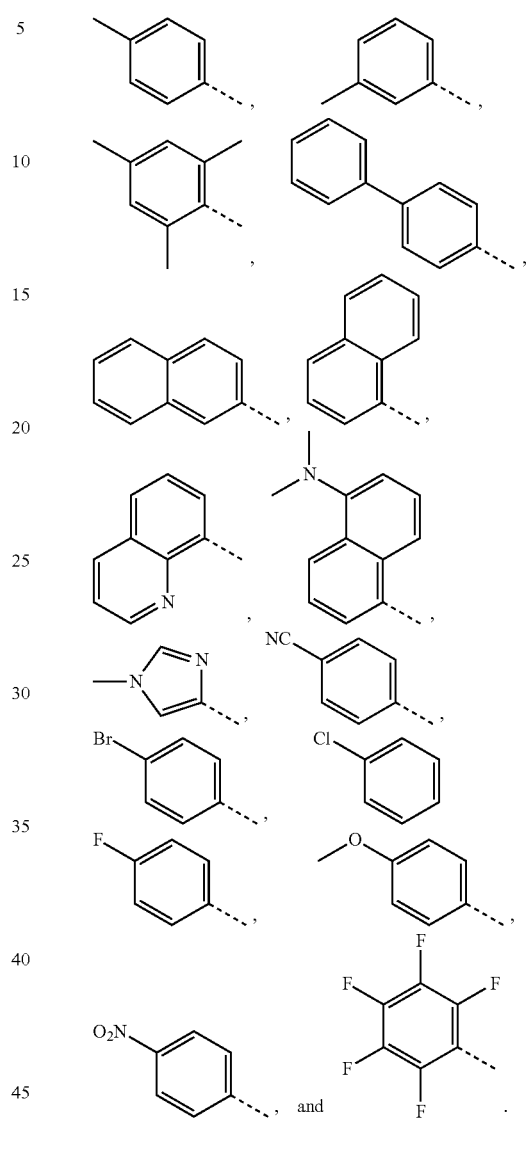
and
wherein $R^4$ is a structure represented by formula:
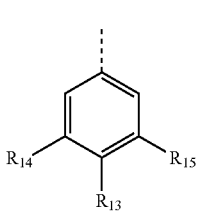
wherein $R^{13}$ is selected from the group consisting of —H, —OH, —COR$^{16}$, —CN, —CH$_2$PO(OH)$_2$, —CH$_2$P(O)$_3$(CH$_2$CH$_3$)$_2$, —NO$_2$, —NHR$^{17}$, and 1H-tetrazole;
$R^{16}$ is selected from the group consisting of: —OH, —O—C$_{(1-2)}$alkyl, —OCH$_2$OC(O)CH$_3$, and —OCH$_2$OC(O)t-Butyl;

$R^{17}$ is selected from the group consisting of: —H, —C(O)C(O)CH$_2$CH$_3$, —C(O)C(O)OH, and —C(O)CH$_2$-1H-tetrazole;

$R^{14}$ is —H or —COOH or when $R^{13}$ is —COR$^{16}$ and $R^{16}$ is OH, $R^{14}$ is —F, or —OC(O)CH$_3$; and $R^{15}$ is H, —OH, or —COOH or when $R^{13}$ is —COR$^{16}$ and $R^{16}$ is OH, $R^{15}$ is —F, or —OC(O)CH$_3$;

wherein $R^{13}$ is —H when $R^{15}$ is —OH or both $R^{14}$ and $R^{15}$ are —COOH, and $R^{14}$ and $R^{15}$ are —H when $R_3$ is

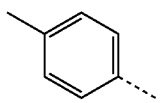

and $R^{13}$ is —OH.

2. The compound of claim 1, or a pharmaceutically acceptable salt, solvate or prodrug thereof, wherein m=0 and $R^2$ is —CH$_3$.

3. The compound of claim 1, or a pharmaceutically acceptable salt, solvate or prodrug thereof, wherein $R^1$ is -(A$^3$)-(A$^2$), A$^2$ and A$^3$ both having the definition as in claim 1.

4. The compound of claim 3, or a pharmaceutically acceptable salt, solvate or prodrug thereof, wherein n is 1, A$^2$ is cyclohexyl and A$^3$ is aryl.

5. The compound of claim 1, or a pharmaceutically acceptable salt, solvate or prodrug thereof, wherein $R^3$ is pentafluorobenzene.

6. A compound that is compound 22, or 33 from Table 1 having a structure below,

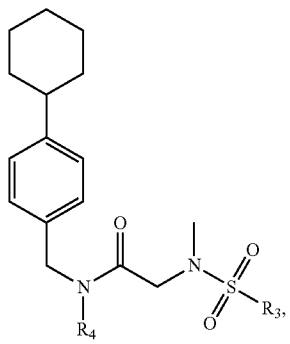

wherein R$_4$ is

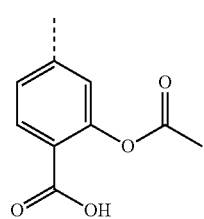

and R$_3$ is

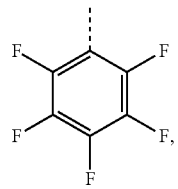

or
wherein R$_4$ is

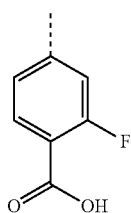

and R$_3$ is

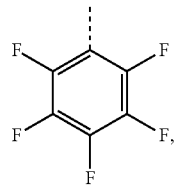

or a pharmaceutically acceptable salt, solvate or prodrug thereof.

7. A pharmaceutical composition comprising a compound as defined in claim 1 or a pharmaceutically acceptable salt, solvate or prodrug thereof, and an acceptable excipient.

8. A method for inhibiting STAT3 and or STAT5 activity, comprising administering a therapeutically effective amount of a compound as defined in claim 1 or a pharmaceutically acceptable salt, solvate or prodrug thereof, to a patient.

9. A method for reducing tumor growth with cancer cells harbouring activated STAT3 or STAT5, comprising administering a therapeutically effective amount of a compound as defined in claim 1, or a pharmaceutically acceptable salt, solvate or prodrug thereof to a patient.

10. The method of claim 9, where said cancer cells are from solid or hematological tumors.

11. The method of claim 10, wherein said cancer cells are from a cancer selected from the group consisting of breast cancer, brain cancer, liver cancer, prostate cancer, pancreatic cancer, blood cancer, skin cancer, head cancer, neck cancer, glioblastoma, multiple myeloma, acute myelogenic leukemia (AML) and acute lymphoblastic leukemia.

12. A method of using the pharmaceutical composition as defined in claim 7 for inhibiting STAT3 and/or STAT5 activity, the method comprising contacting a cell comprising STAT3 and/or STAT5 with the pharmaceutical composition.

13. The method of using the pharmaceutical compositions as defined in claim 12, for use in reducing tumor growth with cancer cells harbouring activated STAT3 or STAT5.

14. The method of using the pharmaceutical compositions as defined in claim 13, wherein said cancer cells are from solid or hematological tumors.

15. The method of using the pharmaceutical compositions as defined in claim 14, wherein said cancer cells are from a cancer selected from the group consisting of breast cancer, brain cancer, liver cancer, prostate cancer, pancreatic cancer, blood cancer, skin cancer, head cancer, neck cancer, glioblastoma, multiple myeloma, acute myelogenic leukemia (AML) and acute lymphoblastic leukemia.

* * * * *